United States Patent
Stallings et al.

(10) Patent No.: US 10,945,999 B2
(45) Date of Patent: Mar. 16, 2021

(54) RING-FUSED THIAZOLINO 2-PYRIDONES, METHODS FOR PREPARATION THEREOF AND THEIR USE IN THE TREATMENT AND/OR PREVENTION OF TUBERCULOSIS

(71) Applicants: QURETECH BIO AB, Umeå (SE); Washington University in Saint Louis, St. Louis, MO (US)

(72) Inventors: Christina L. Stallings, St. Louis, MO (US); Fredrik Almqvist, Umeå (SE); Kelly Flentie, Jamaica Plain, MA (US); James Arthur Dudley Good, Durham (GB); Fritiof Ponten, Askim (SE)

(73) Assignees: QURETECH BIO AB, Umea (SE); WASHINGTON UNIVERSITY IN SAINT LOUIS, Saint Louis, MO (US)

( * ) Notice: Subject to any disclaimer, the term of this patent is extended or adjusted under 35 U.S.C. 154(b) by 0 days.

(21) Appl. No.: 16/091,774

(22) PCT Filed: Apr. 7, 2017

(86) PCT No.: PCT/IB2017/051999
§ 371 (c)(1),
(2) Date: Oct. 5, 2018

(87) PCT Pub. No.: WO2017/175182
PCT Pub. Date: Oct. 12, 2017

(65) Prior Publication Data
US 2019/0091210 A1 Mar. 28, 2019

Related U.S. Application Data
(60) Provisional application No. 62/319,838, filed on Apr. 8, 2016.

(51) Int. Cl.
| | | |
|---|---|---|
| A61K 31/4365 | (2006.01) |
| A61K 45/06 | (2006.01) |
| A61P 31/06 | (2006.01) |
| A61K 31/4409 | (2006.01) |
| A61K 31/47 | (2006.01) |
| A61K 31/69 | (2006.01) |

(52) U.S. Cl.
CPC ...... *A61K 31/4365* (2013.01); *A61K 31/4409* (2013.01); *A61K 31/47* (2013.01); *A61K 31/69* (2013.01); *A61K 45/06* (2013.01); *A61P 31/06* (2018.01)

(58) Field of Classification Search
CPC .................................................. A61K 31/4365
USPC ........................................................ 514/301
See application file for complete search history.

(56) References Cited

U.S. PATENT DOCUMENTS 7,915,417 B2   3/2011   Hultgren et al.

FOREIGN PATENT DOCUMENTS

| CA | 2691379 A1 | 12/2008 |
| EA | 18104 B1 | 5/2013 |
| WO | WO 2005102330 A2 | 11/2005 |
| WO | WO-2014/185853 | 11/2014 |
| WO | WO-2015/011163 | 1/2015 |
| WO | WO-2016/075296 | 5/2016 |

OTHER PUBLICATIONS

Alteri et al., PNAS (2007), vol. 104(12), pp. 5145-5150.*
King, Med. Chem., Principle and Practice (1994), pp. 206-208.*
Åberg, V. et al., C-Terminal Properties are Important for Ring-Fused 2-Pyridones that Interfere with Chaperone Function in Uropathogenic *E. coli*. Org Biomol Chem. 2005; 3:3886-92.
Åberg, V. et al., Microwave-Assisted Decarboxylation of Bicyclic 2-Pyridone Scaffolds and Identification of Aβ-Peptide Aggregation Inhibitors. Org Biomol Chem. 2005; 3(15):2817-23.
Chorell, E. et al., Diverse Functionalization of Thiazolo Ring-Fused 2-Pyridones. J Org Chem. 2007; 72(13):4917-24.
Emtenäs, H. et al., Design and Parallel Solid-Phase Synthesis of Ring-Fused 2-Pyridinones That Target Pilus Biogenesis in Pathogenic Bacteria. J Comb Chem. 2002; 4(6):630-9.
Pemberton, N. et al., Functionalization of Bicyclic 2-Pyridones Targeting Pilus Biogenesis in Uropathogenic *Escherichia coli*. Tetrahedron Lett. 2007; 48(26):4543-6.
Åberg, V. et al., Carboxylic Acid Isoteres Improve the Activity of Ring-Fused 2-Pyridones that Inhibit Pilus Biogenesis in *E. coli*. Bioorg Med Chem Lett. 2008; 18(12):3536-40.
Bengtsson et al., Design, Synthesis and Evaluation of Triazole Functionalized Ring-Fused 2-Pyridones as Antibacterial Agents. Eur J Med Chem. 2012; 54:637-46.

(Continued)

*Primary Examiner* — Taofiq A Solola
(74) *Attorney, Agent, or Firm* — Ballard Spahr LLP

(57) ABSTRACT

The present disclosure provides a combination comprising:
(i) a drug against tuberculosis,
or a pharmaceutically acceptable salt thereof, and
(ii) a compound of Formula II,

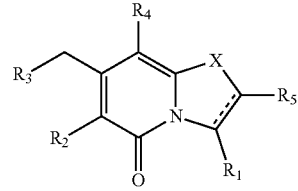

Formula II or a pharmaceutically acceptable combination thereof.

The combination may be used in the treatment and/or prevention of tuberculosis.

20 Claims, 8 Drawing Sheets

(56) References Cited

OTHER PUBLICATIONS

Bengtsson, D., Synthesis of Substituted Ring-Fused 2-Pyridones and Applications in Chemical Biology. Doctoral Thesis. Dept. Chem., Umeå University, Umeå, Sweden 2013 (96 pages).

Chorell, E. et al., Design and Synthesis of C-2 Substituted Thiazolo and Dihydrathiazolo Ring-Fused 2-Pyridones: Pillcides with Increased Antivirulence Activity. J Med Chem. 2010; 53(15):5690-5.

Chorell, E. et al., Mapping Pilicide Anti-Virulence Effect in *Escherichia coli*, a Comprehensive Structure-Activity Study. Bioorg Med Chem. 2012; 20(9):3128-42 (39 pages).

Good, J.A.D. et al., Attenuating *Listeria monocytogenes* Virulence by Targeting the regulatory Protein PrfA. Cell Chem Biol. 2016; 23(3):404-14 (26 pages).

Good, J.A.D. et al., Thiazolino 2-Pyridone Amide Inhibitors of PC *Chlamydia trachomatis* Infectivity. J Med Chem. 2016; 59(5):2094-108.

International Search Report and Written Opinion dated Jun. 30, 2017 by the International Searching Authority for Patent Application No. PCT/IB2017/051999, which was filed Apr. 7, 2017 and published as WO 2017/175182 dated Oct. 12, 2017 (Inventor—Stallings et al.; Applicant—Quretech Bio AB) (11 pages).

\* cited by examiner

Rifampicin

Pyrazinamide

Ethambutol

Bedaquiline

Ethionamide

Delamanide

Pretomanid

Formula IIIa

Formula IIIb

Formula IVa1

Formula IVa2

Formula IVa3

Formula IVa4

Formula Va1

Formula Va2

Formula Va3

Formula Va4

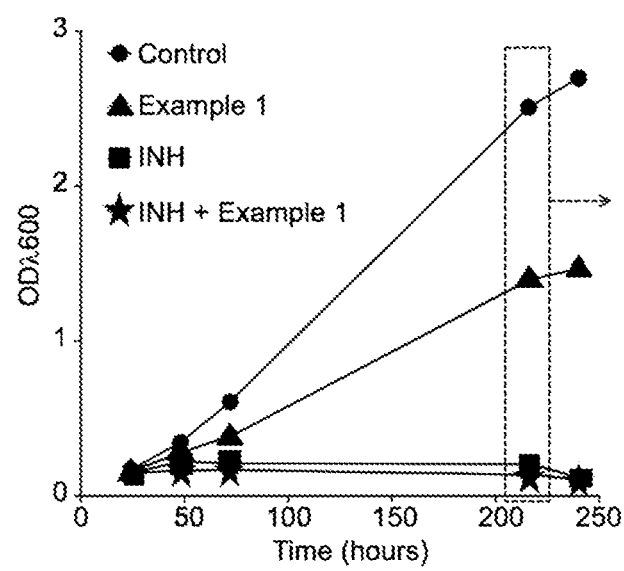
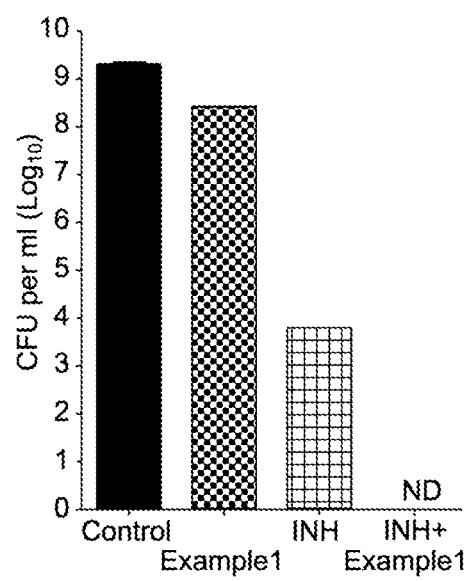
Figure 8a
Figure 8b
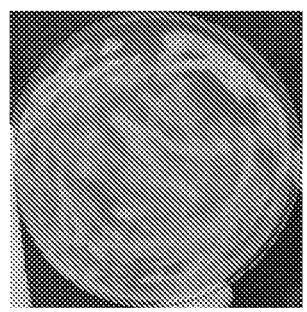
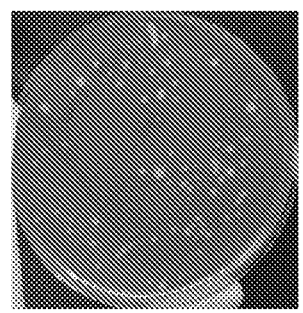
Figure 8c
Figure 8d
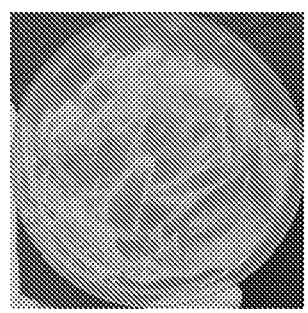
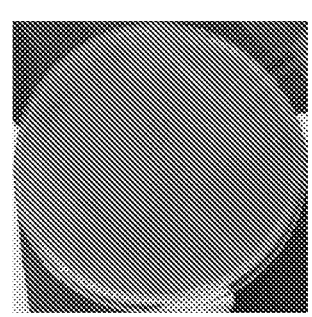
Figure 8e
Figure 8f

RING-FUSED THIAZOLINO 2-PYRIDONES, METHODS FOR PREPARATION THEREOF AND THEIR USE IN THE TREATMENT AND/OR PREVENTION OF TUBERCULOSIS

CROSS-REFERENCE TO RELATED APPLICATIONS

This application is a U.S. National Phase Application of International Application No. PCT/IB2017/051999, filed Apr. 7, 2017, which claims priority to U.S. Provisional Application No. 62/319,838, filed Apr. 8, 2016, each of which are hereby incorporated by reference in their entirety.

TECHNICAL FIELD

The present disclosure relates to ring-fused thiazolino 2-pyridones, to processes for preparing such compounds, to their use in treating and/or preventing tuberculosis infections, to methods for their therapeutic use and to a pharmaceutical composition containing any such compounds. In particular, the present disclosure relates to said ring-fused thiazolino 2-pyridones in combination with a drug against tuberculosis, to the use of such a combination in treating and/or preventing tuberculosis infections, to methods for its therapeutic use and to a pharmaceutical composition containing any such combinations.

BACKGROUND

Tuberculosis (TB) infects at least 30% of the world's population. Every year there are about 9 million newly infected patients, and about 1.5 million deaths. A major roadblock in treating tuberculosis (TB) is the recalcitrance of *Mycobacterium tuberculosis* (Mtb) to currently available antibiotics, which necessitates lengthy treatment regimens that do not always eradicate the tuberculosis bacteria.

The main cause of TB is *Mycobacterium tuberculosis* (Mtb). However, there are also other tuberculosis causing mycobacteria such as *M. bovis, M. africanum, M. canetti,* and *M. microti*.

Patients suffering from tuberculosis may have active tuberculosis or latent tuberculosis. Active tuberculosis means that tuberculosis bacteria are reproducing and spreading in the body, causing tissue damage. A patient infected with active tuberculosis feels sick. Common symptoms are cough that does not go away, coughing blood and weight loss. Further, a patient suffering from active tuberculosis is infectious, i.e. can spread tuberculosis to other people. The tuberculosis is spread through the air when the patient talks, coughs, sneezes etc.

Latent tuberculosis, which may also be denominated dormant, chronic or persistent tuberculosis, means that tuberculosis bacteria do not multiply to detectable levels in the body. Commonly, a person infected with latent tuberculosis has no symptoms and is not infectious. The dormant phase can last for a very long time, even during the whole life time of the infected person. However, the tuberculosis infection may be reactivated into active tuberculosis. In particular, this may happen in patients having an immune system deficiency or taking immunosuppressive agents.

Exposure to tuberculosis can be detected through a tuberculin skin test or blood test. There is currently no diagnostic test that can distinguish between patients that have been exposed and cleared an infection versus someone who is latently infected. Active pulmonary tuberculosis is detected through sputum smears or culturing of sputum.

Current treatment and prophylactics of drug susceptible tuberculosis are based on combination therapies including isoniazid (isonicotinylhydrazide, INH). In the standard clinical practice, isoniazid is used in combination with rifampicin (RIF), ethambutol (EMB) and pyrazinamide (PZA) in a 6 month regimen to treat drug-susceptible active Mtb infection. The long duration of antibiotic therapy has serious side effects, and eradication of tuberculosis bacteria is often incomplete. Further, this long-term antibiotic therapy has resulted in the rise of drug resistant tuberculosis, such as multidrug resistant tuberculosis, which constitutes 3.5% of new tuberculosis cases and 20% of previously treated cases. In addition, people infected with latent Mtb are prophylactically treated with 9 months of INH or 12 weeks of INH and rifapentine to prevent reactivation of the bacteria.

Mtb infecting a patient may be divided into so-called nonpersisters and persisters. While nonpersister bacteria may be eradicated with commonly used tuberculosis antibiotics, the persisters are tolerant of such antibiotics. The recalcitrance of Mtb persisters to therapy has led to an increase in drug resistance.

Thus, the frequent lack of complete tuberculosis eradication, drug resistance and/or the long treatment times are major challenges associated with current tuberculosis treatment.

PCT/EP2015/076578 discloses ring-fused thiazolino 2-pyridones, to processes for preparing such compounds, to their use in treating and/or preventing bacterial infections such as *Chlamydia*. It is mentioned that the ring-fused thiazolino 2-pyridones may be administered in combination with another therapeutic agent such as an antibiotic. It is not mentioned to use ring-fused thiazolino 2-pyridones for inhibition of biofilm formation or treating tuberculosis.

WO 2014/185853 discloses ring-fused 2-pyridones shown to reduce the infectivity of *Chlamydia*. Treatment of tuberculosis is not mentioned.

There is a need for alternative and/or improved treatments of tuberculosis. In particular, there is a need for treatment of tuberculosis that shortens the duration of the treatment, decreases the rates of drug resistance and/or allows for complete or nearly complete tuberculosis eradication.

It is an object of the present disclosure to provide compounds useful in the treatment and/or prevention of tuberculosis. Further, it is an object of the present disclosure to provide compounds that may be used in combination with current therapeutic agents such as isoniazid to improve treatment and/or prevention of tuberculosis.

SUMMARY

The present disclosure provides a combination comprising:
(i) a drug against tuberculosis,
or a pharmaceutically acceptable salt thereof; and
(ii) a compound of Formula II

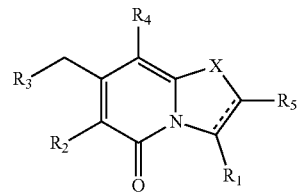

Formula II or a pharmaceutically acceptable salt thereof,
wherein
R₁ is selected from the group consisting of
a) C(O)OH,
b) tetrazolyl,
c) CH₂OH,
d) C(O)NRaRab,
e) C(O)NHSO₂R₇,
f) C(O)OR₈,
g) NH₂,
h) H,
i),

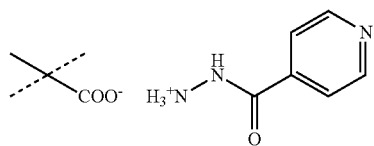

j)

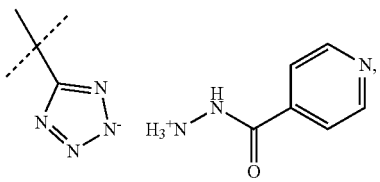

and
k)

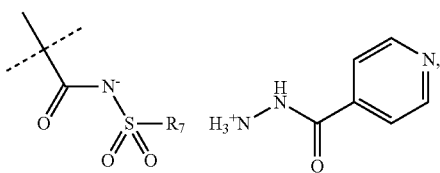

R₂ is selected from the group consisting of:
a) H,
b) Cl, F, Br or I,
c) CH₂OH,
d) C₁-C₄alkyl, and
e) NY₁Y₂,
R₃ is selected from the group consisting of
a) 1-naphtyl, 2-naphtyl or 1-naphtyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophene-2-yl,
f) H or C₁-C₄-alkyl,
g) 2-methyl-1-aza-2-bora-1H-naphth-5-yloxy,
h) 2-methyl-1-aza-2-bora-1H-naphth-5-yl,
i) 2-methyl-1-aza-2-bora-1H-naphth-8-yloxy, and
j) 2-methyl-1-aza-2-bora-1H-naphth-8-yl, R₄ is selected from the group consisting of
a) C₁-C₄alkyl substituted by 0, 1, 2, 3 or 4 fluoro;
b) C₃-C₆cycloalkyl,
c) C₁-C₄alkoxy substituted by 0, 1, 2, 3 or 4 fluoro,
d) C₃-C₆cycloalkoxy,
e) a 3-, 4-, 5- or 6-membered heterocycle,
f) N-methyl 3-indolyl, and
g) NR₉R₁₀,
R₅ is selected from the group consisting of
a) H,
b) phenyl substituted with 0, 1, 2 or 3 methyl group(s),
c) benzyl,
d) thienyl,
e) C₁-C₄alkoxy, and
f) a 3-, 4-, 5- or 6-membered heterocycle.

There is also provided a combination as described herein for use as a medicament in therapy.

Further, there is provided a combination as described herein for use in the treatment and/or prevention of tuberculosis.

Further, there is provided the use of a combination as described herein for the manufacture of a medicament for the treatment and/or prevention of tuberculosis.

There is also provided a method for treatment and/or prevention of tuberculosis comprising administering to a mammal, such as a human or an animal, in need thereof an effective amount of a combination as described herein.

The present disclosure also provides a compound of Formula II as described herein for use in the treatment and/or prevention of tuberculosis.

There is also provided a use of a compound of Formula II as described herein for the manufacture of a medicament for the treatment and/or prevention of tuberculosis.

There is also provided a method for treatment and/or prevention of tuberculosis comprising administering to a mammal, such as a human or an animal, in need thereof an effective amount of a compound of Formula II as described herein.

Moreover, there is provided a compound of Formula IIIa and/or IIIb:

Formula IIIa

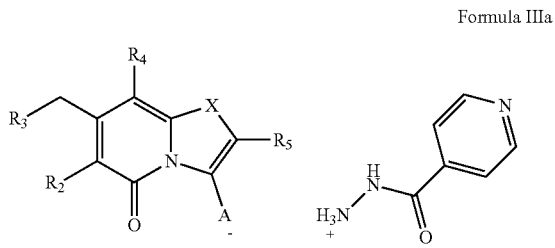

Formula IIIb

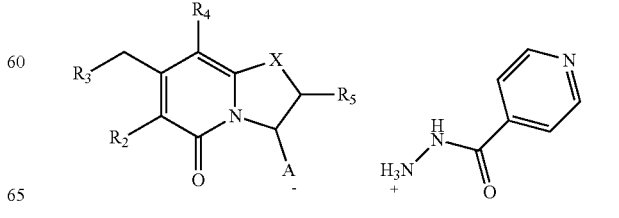

wherein A- is selected from:
COO⁻, or
C(O)N⁻SO₂R₇, and
wherein
$R_2$, $R_3$, $R_4$, $R_5$ and $R_7$ may be as described for Formula II, or a pharmaceutically acceptable salt thereof.

There is also provided a compound of compound of Formula IIIa and/or Formula IIIb for use as a medicament in therapy.

The present disclosure also provides a compound of Formula IV:

Formula IV or a pharmaceutically acceptable salt thereof. $R_2$, $R_3$, $R_4$, and $R_5$ may be as described for Formula II. There is also provided a compound of Formula IV as a medicament in therapy.

BRIEF DESCRIPTION OF THE DRAWINGS

FIG. 8a shows WT Mtb growth in planktonic, aerated cultures.

FIG. 8b shows WT Mtb plated for CFUs to determine live Mtb.

FIG. 8c shows a photograph of growth of plated WT Mtb on an agar plate when INH and the compound of Example 1 were absent.

FIG. 8d shows a photograph of growth of plated WT Mtb on an agar plate for INH.

FIG. 8e shows a photograph of growth of plated WT Mtb on an agar plate for the compound of Example 1.

FIG. 8f shows a photograph of growth of plated WT Mtb on an agar plate for a combination of INH and the compound of Example 1.

DETAILED DESCRIPTION

Figure 1:
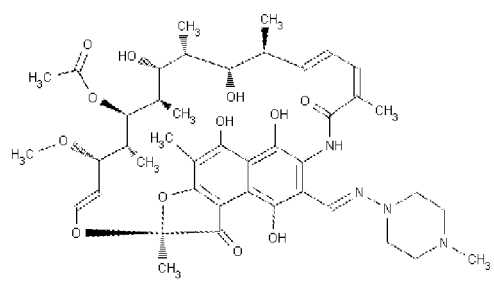
FIG. 1 shows the chemical structures of the drugs rifampicin (RIF), pyrazinamide (PZA) and ethambutol (EMB).
Figure 1:
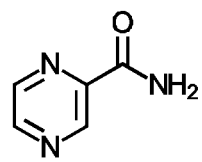
Figure 1:
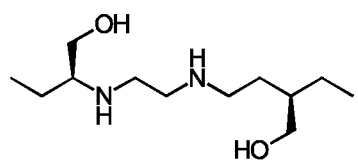

The present disclosure provides a combination comprising:
 (i) a drug against tuberculosis,
 or a pharmaceutically acceptable salt thereof; and
 (ii) a compound of Formula II Formula II or a pharmaceutically acceptable salt thereof,
wherein
$R_1$ is selected from the group consisting of
 a) C(O)OH,
 b) tetrazolyl,
 c) $CH_2OH$,
 d) $C(O)NR_{6a}R_{6b}$, e) C(O)NHSO$_2$R$_7$,
f) C(O)OR$_8$,
g) NH$_2$,
h) H,
i)

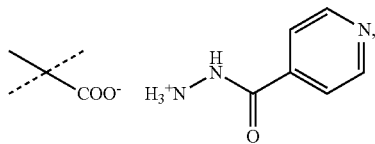

j)

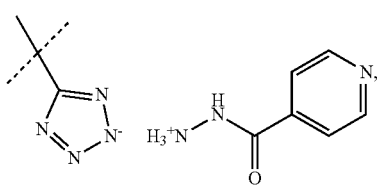

and
k)

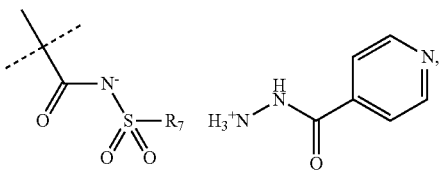

R$_2$ is selected from the group consisting of:
a) H,
b) Cl, F, Br or I,
c) CH$_2$OH,
d) C$_1$-C$_4$alkyl, and
e) NY$_1$Y$_2$,
R$_3$ is selected from the group consisting of
a) 1-naphtyl, 2-naphtyl or 1-naphtyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl,
d) 2-(3-methyl)phenylmethylene,
e) benzothiophene-2-yl,
f) H or C$_1$-C$_4$-alkyl,
i) 2-methyl-1-aza-2-bora-1H-naphth-5-yloxy, and
j) 2-methyl-1-aza-2-bora-1H-naphth-5-yl,
R$_4$ is selected from the group consisting of
a) C$_1$-C$_4$alkyl substituted by 0, 1, 2, 3 or 4 fluoro,
b) C$_3$-C$_6$cycloalkyl,
c) C$_1$-C$_4$alkoxy substituted by 0, 1, 2, 3 or 4 fluoro,
d) C$_3$-C$_6$cycloalkoxy,
e) a-3-, 4-, 5- or 6-membered heterocycle,
f) N-methyl 3-indolyl, and
h) NR$_9$R$_{10}$, R$_5$ is selected from the group consisting of
a) H,
b) phenyl substituted with 0, 1, 2 or 3 methyl group(s),
c) benzyl,
d) thienyl,
e) C$_1$-C$_4$alkoxy, and
f) a 3-, 4-, 5- or 6-membered heterocycle.
The following definitions shall apply throughout this document unless stated otherwise.
R$_{6a}$ is selected from the group consisting of H and C$_1$-C$_4$alkyl.
R$_{6b}$ is selected from the group consisting of H, C$_1$-C$_4$alkyl, C$_1$-C$_4$alkoxy and isonicotinoylamino.
R$_7$ is SO$_2$C$_1$-C$_4$alkyl or SO$_2$phenyl.
R$_8$ represents 2-{2-[1-(hydroxymethyl)propylamino]ethylamino}butyl).
R$_{9a}$ represents C$_1$-C$_4$alkyl,
R$_{9b}$ represents C$_1$-C$_4$alkyl,
R$_{10}$ represents C$_1$-C$_4$alkyl, or
R$_9$ and R$_{10}$ together form CH$_2$(CH$_2$)$_m$CH$_2$.
Y$_1$ and Y$_2$ each independently represents hydrogen, methyl, CH$_3$S(O)$_2$ or C(O)CH$_3$, or Y$_1$ and Y$_2$ together form CH$_2$CH$_2$CH$_2$CH$_2$ or CH$_2$CH$_2$CH$_2$CH$_2$CH$_2$.
X is S, SO or SO$_2$.
m is 1, 2 or 3.
The term "C$_1$-C$_4$alkyl" denotes a straight or branched, saturated or unsaturated alkyl group of one to four carbon atoms. Examples of "C$_1$-C$_4$alkyl" include, but are not limited to, methyl, ethyl, vinyl, allyl, n-propyl, isopropyl, n-butyl, sec-butyl.iso-butyl and tert-butyl.
The term "C$_1$-C$_4$alkoxy" denotes a C$_1$-C$_4$alkyl group as described herein which is linked to an oxygen atom. Examples of "C$_1$-C$_4$alkoxy" include, but are not limited to, methoxy, ethoxy, n-propoxy, iso-propoxy and butoxy.
The term "C$_3$-C$_6$cycloalkyl" denotes a saturated or unsaturated non-aromatic monocyclic ring composed of three, four, five or six carbon atoms. Examples of "C$_3$-C$_6$cycloalkyl" include, but are not limited to, cyclopropyl, cyclobutyl, cyclopentyl and cyclohexyl.
The term "C$_3$-C$_6$cycloalkoxy" denotes a saturated or unsaturated non-aromatic monocyclic ring composed of three, four, five or six carbon atoms which is linked to an oxygen atom. Examples of "C$_3$-C$_6$cycloalkoxy" include, but are not limited to, cyclopropyloxy, cyclopropxymethylene, cyclobutyloxy, cyclobutyloxymethylene, cyclopentyloxy, cyclopentyloxymethylene, cyclohexyloxyand cyclohexyloxymethylene.
The term "3-membered heterocycle" denotes a 3-membered saturated or unsaturated heterocycle. Examples of a 3-membered saturated heterocycle include, but are not limited to, aziridine, oxirane and thiirane. Examples of 3-membered unsaturated heterocycles include, but are not limited to, azirine, oxirene and thiirene.
The term "4-membered heterocycle" denotes a 4-membered saturated or unsaturated heterocycle. Examples of a 4-membered heterocycle include, but are not limited to, azetidine, oxethane and thietane.
The term "5-membered heterocycle" denotes a 5-membered saturated or unsaturated heterocycle. Examples of a 5-membered heterocycles include, but are not limited to pyrrolidine, tetrahydrofurane, thiolane, pyrrole, furane, thiophene, imidazolidine, pyrazolidine, pxazolidine, isoxazolidine, thiazolidine, isothiazolidine, dioxolane, dithiolane, imidazole, pyrazole, oxazole, isoxazole, thiazole, and isothiazole
The term "6-membered heterocycle" denotes a 6-membered saturated or unsaturated heterocycle. Examples of a 6-membered heterocycles include, but are not limited to piperidine, pyridine, piperazine, morpholine, and thiomorpholine.

The drug against tuberculosis is to be understood as a drug that counteracts tuberculosis bacteria. The drug against tuberculosis may reduce, substantially eliminate or eradicate tuberculosis bacteria. The drug against tuberculosis may also be denominated an anti-tuberculosis drug or a drug to treat tuberculosis.

Examples of drugs against tuberculosis that may be used in combination with the compounds of Formula II as described herein include first line anti-tuberculous drugs, second line anti-tuberculous drugs and/or third line anti-tuberculous drugs. First line anti-tuberculous drugs may be at least one of the following: isoniazid, ethambuthol, pyrazinamide, rifampicin, streptomycin. For instance, the drug against tuberculosis may be at least one of the following: isoniazid, ethambuthol, pyrazinamide, rifampicin. In an example, the drug against tuberculosis may be isoniazid optionally in combination with at least one of ethambuthol, pyrazinamide, rifampicin.

Second line anti-tuberculosis drugs may be at least one of the following:
  aminoglycosides, such as amikacin or kanamycin,
  polypeptides such as capreomycin, viomycin, enviomycin,
  fluoroquinolones such as ciprofloxacin (CIP), levofloxacin, moxifloxacin (MXF);
  thioamides such as ethionamide, prothionamide,
  cycloserine,
  terizidone.

Third line anti-tuberculosis drugs may be at least one of the following:
  rifabutin,
  macrolides such as chlaritromycin (CLLR),
  linezolid (LZD),
  thioridazine;
  arginine,
  vitamin D,
  bedaquiline,
  pretomanid,
  delamanid.

Examples of drugs against tuberculosis that may be used in combination with the compounds of Formula II as described herein include isoniazid, pyrazinamide, pretomanid, delamanid, bedaquiline, streptomycin, levofloxacin, moxifloxacin and ofloxacin, cycloserine, terizidone, thionamide, protionamide and-4-aminosalicylic acid. For instance, the drug against tuberculosis may be isoniazid and/or 4-aminosalicylic acid. In a further example, the drug against tuberculosis may be isoniazide and/or bedaquiline, optionally in combination with at least one of ethambutol, pyrazinamide, rifampicin.

In addition or as an alternative to the compounds of Formula II described herein, the compounds described in WO 2014/185853 and/or PCT/EP2015/076578 are provided and incorporated by reference. These compounds may be used in combination with the drug against tuberculosis described herein and/or in the treatment and/or prevention of tuberculosis.

In this document, isonicotinylhydrazide has the chemical structure shown below. Isonicotinylhydrazide is also denominated isoniazid (INH). In this document, the terms isonicotinylhydrazide, isoniazid and INH are used interchangeably.

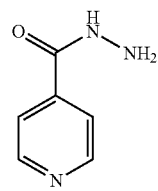

Isonicotinylhydrazide

Figure 2:
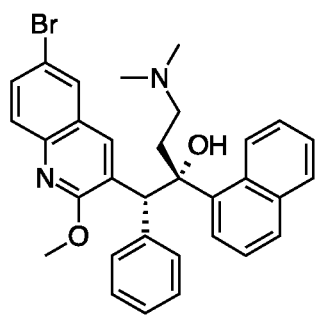
FIG. 2 shows the chemical structures of the drugs bedaquiline, ethionamide, delamanide and pretomanid.
Figure 2:
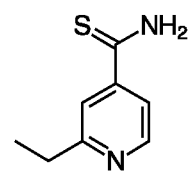
Figure 2:
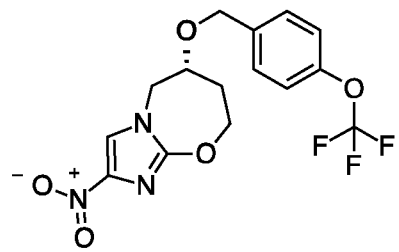
Figure 2:
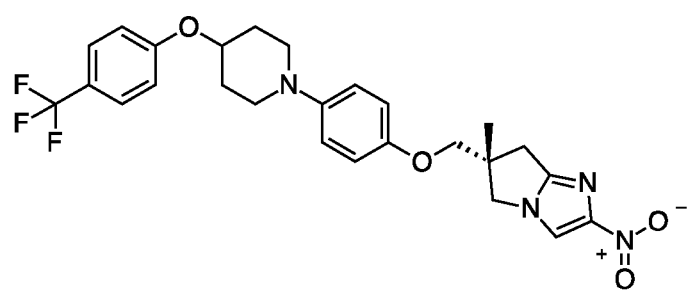
Figure 3:
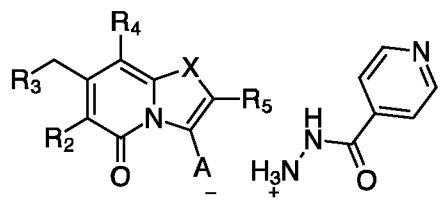
FIG. 3 shows compounds of Formula IIIa and Formula IIIb.
Figure 3:
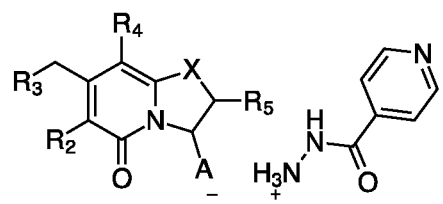
Figure 4:
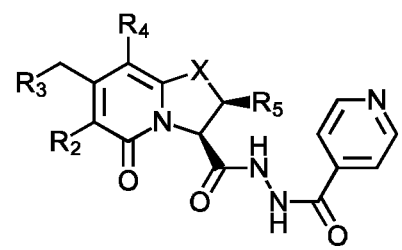
FIG. 4 shows compounds of Formula IVa1, IVa2, IVa3 and IVa4.
Figure 4:
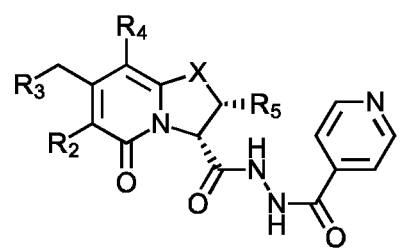
Figure 4:
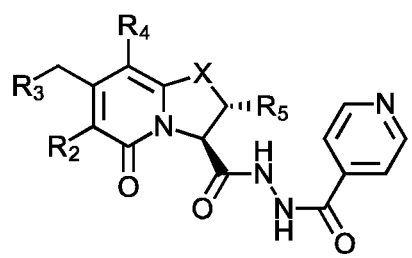
Figure 4:
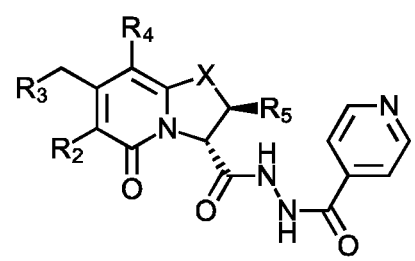
Figure 5A:
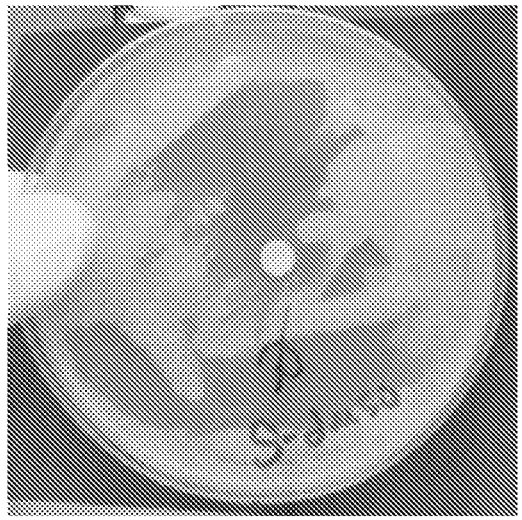
FIG. 5a shows an agar plate containing 0.05% DMSO and inoculated with $1.959 \times 10^8$ CFU of Mycobacterium tuberculosis and a disk spotted with 5 l of water placed onto the plate at the time of inoculation. Photo was taken after 4 weeks of incubation at 37° C. in 5% $CO_2$.
Figure 5B:
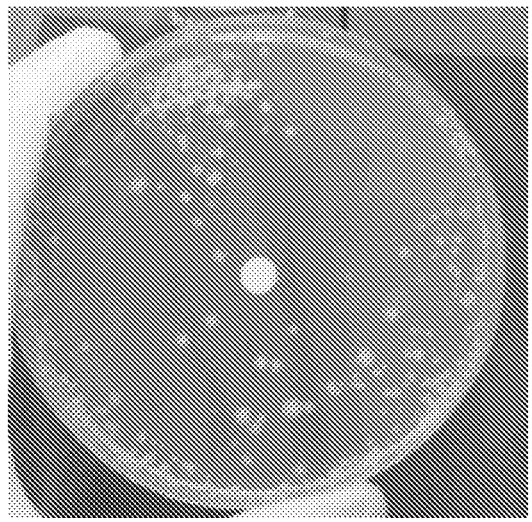
FIG. 5b shows an agar plate containing 0.05% DMSO and inoculated with $1.959 \times 10^8$ CFU of Mycobacterium tuberculosis and a disk spotted with 5 μl of 0.5 mg/ml INH placed onto the plate at the time of inoculation. Photo was taken after 4 weeks of incubation at 37° C. in 5% $CO_2$.
Figure 5C:
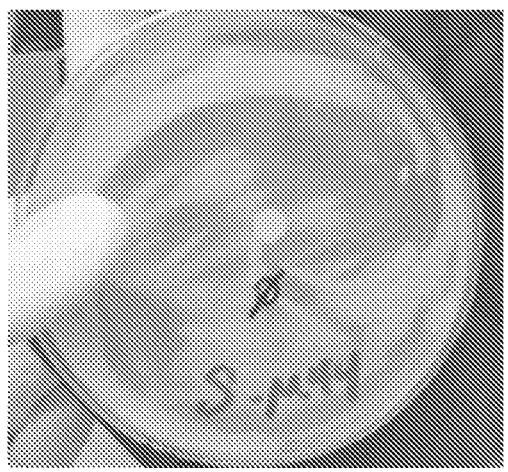
FIG. 5c shows an agar plate containing a DMSO solution of 25 μM (3R)-7-Cyclopropyl-6-[(1-naphthyl)methyl]-4-oxo-1-thia-3a-aza-3-indancarboxylic acid and inoculated with $1.959 \times 10^8$ CFU of Mycobacterium tuberculosis and a disk spotted with 5 l of water placed onto the plate at the time of inoculation. Photo was taken after 4 weeks of incubation at 37° C. in 5% $CO_2$.
Figure 5D:
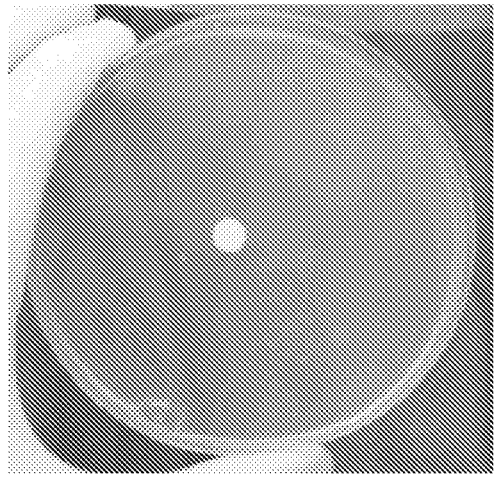
FIG. 5d shows an agar plate containing a DMSO solution of 25 μM (3R)-7-Cyclopropyl-6-[(1-naphthyl)methyl]-4-oxo-1-thia-3a-aza-3-indancarboxylic acid and inoculated with $1.959 \times 10^8$ CFU of Mycobacterium tuberculosis and a disk spotted with 5 l of 0.5 mg/ml INH placed onto the plate at the time of inoculation. Photo was taken after 4 weeks of incubation at 37° C. in 5% $CO_2$.
Figure 6:
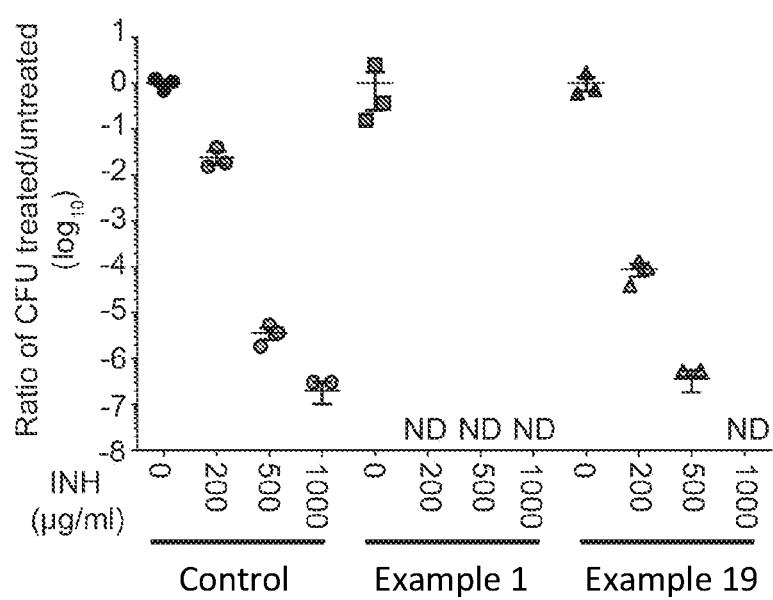
FIG. 6 shows the ratio of colony forming units of treated/untreated tuberculosis bacteria upon addition of isoniazid, a combination of isoniazid and the compound of Example 1 described herein and a combination of isoniazid and the compound of Example 19 as described herein, respectively.
Figure 7:
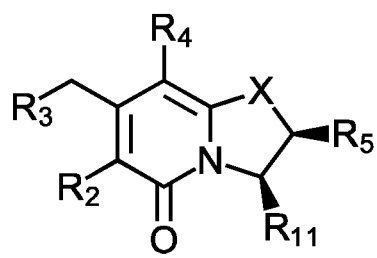
FIG. 7 shows compounds of Formula Va1, Formula Va2, Formula Va3 and Formula Va4.
Figure 7:
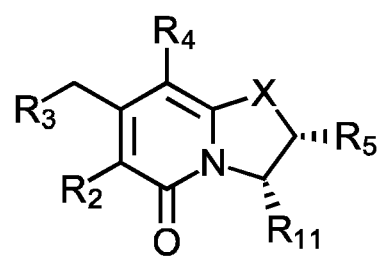
Figure 7:
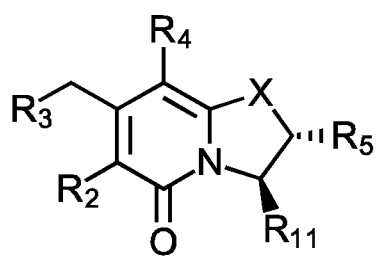
Figure 7:
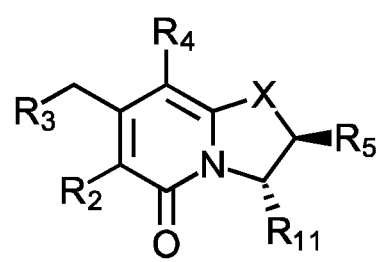

In this document, the drugs rifampicin (RIF), pyrazinamide (PZA) and/or ethambutol (EMB) are understood to have the chemical structures depicted in FIG. 1. Further, bedaquiline, ethionamide, delamanide and pretomanid are understood to have the chemical structures depicted in FIG. 2.

Surprisingly, the inventors of the present disclosure have found that the compounds of Formula II described herein are useful in the treatment and/or prevention of tuberculosis.

The compounds of Formula II may be used separately or in combination with a drug against tuberculosis such as INH.

In an example, there is provided a combination as described herein wherein the drug against tuberculosis is isoniazid.

In a further example, there is provided a combination comprising:
(i) a compound of Formula I

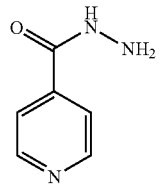

Formula I i.e. isonicotinylhydrazide,
or a pharmaceutically acceptable salt thereof, and
(ii) a compound of Formula II

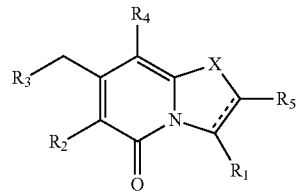

Formula II or a pharmaceutically acceptable salt thereof,
wherein
$R_1$ is selected from the group consisting of
a) C(O)OH,
b) tetrazolyl,
c) $CH_2OH$,
d) $C(O)NR_{6a}R_{6b}$,
e) $C(O)NHSO_2R_7$,
f) $C(O)OR_8$, g) NH$_2$,
h) H,
i)

[chemical structure]

j)

[chemical structure]

and
k)

[chemical structure]

R$_2$ is selected from the group consisting of
a) H,
b) Cl, F, Br or I, and
c) CH$_2$OH, R$_3$ is selected from the group consisting of
a) 1-naphtyl, 2-naphtyl or 1-naphtyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophene-2-yl,
f) H or C$_1$-C$_4$-alkyl,
i) 2-methyl-1-aza-2-bora-1H-naphth-5-yloxy, and
j) 2-methyl-1-aza-2-bora-1H-naphth-5-yl, R$_4$ is selected from the group consisting of
a) C$_1$-C$_4$alkyl substituted by 0, 1, 2, 3 or 4 fluoro;
b) C$_3$-C$_6$cycloalkyl,
c) C$_1$-C$_4$alkoxy substituted by 0, 1, 2, 3 or 4 fluoro,
d) C$_3$-C$_6$cycloalkoxy,
e) 2-thienyl,
f) N-methyl 3-indolyl, and
h) NR$_9$R$_{10}$, R$_5$ is selected from the group consisting of
a) H,
b) phenyl substituted with 0, 1, 2 or 3 methyl group(s),
c) benzyl,
d) thienyl,
e) C$_1$-C$_4$alkoxy, and
f) 1-triazolyl.

Further values of wherein R$_1$, R$_2$, R$_3$, R$_4$, R$_5$, m and X will now follow. It will be appreciated that these values may be applied to any compound of Formula II of the present disclosure.

R$_1$ may be C(O)OH or tetrazolyl. For instance, R$_1$ may be C(O)OH.

R$_2$ may be H.

R$_3$ may be selected from the group consisting of
a) 1-naphtyl, 2-naphtyl or 1-naphtyloxy, each independently substituted with 0, 1, 2 or 3 substituents selected from the group consisting of methyl, fluoro, chloro, cyano and methoxy, and
b) phenyl substituted with 0, 1, 2 or 3 substituents independently selected from the group consisting of methyl, fluoro, chloro, cyano and trifluoromethyl.

Further, R$_3$ may be selected from selected from the group consisting of:
1-naphtyl, 2-naphtyl, 4-methyl-1-naphtyl, 4-fluoro-1-naphtyl, 4-bromo-1-naphtyl, 4-methoxy-1-naphtyl, 2-methoxy-1-naphtyl, 2-methoxy-1-naphtyl, 1-naphtyloxy, 3-methylphenyl, 2,3-dimethylphenyl, 2-fluoro-5-methylphenyl, 2,3-dichlorophenyl, 2-(3-methyl)phenylmethylene; 2,3-xylylamine, 3-trifluoromethylphenyl and benzothiophene-2-yl.

In still a further example, R$_3$ may be selected from the group consisting of:
a) 1-naphtyl, 2-naphtyl or 1-naphtyloxy, each independently substituted with 0, 1, 2 or 3 substituents selected from the group consisting of methyl, fluoro, chloro, cyano and methoxy. For instance, R$_3$ may be 1-naphtyl.

R$_4$ may be C$_2$-C$_6$cycloalkyl. For instance, R$_4$ may be cyclopropyl.

R$_5$ may be H.

X may be S or SO. For instance, X may be S. In a further example, X may be SO. In still a further example, X may be SO$_2$.

The compound of Formula II may exist as Formula IIa or Formula IIb, wherein R$_1$, R$_2$, R$_3$, R$_4$, R$_5$ and X may have the values described herein.

Formula IIa

[chemical structure]

Formula IIb

[chemical structure]

Further, the compound of Formula IIa may exist as cis stereoisomers Formula IIa1 and Formula IIa2 or as trans stereosiomers of Formula IIa3 or Formula IIa4. R$_1$, R$_2$, R$_3$, R$_4$, R$_5$ and X may have values as described herein.

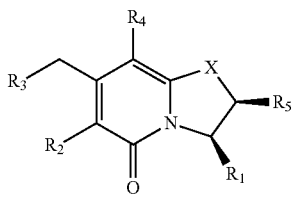

Formula IIa1

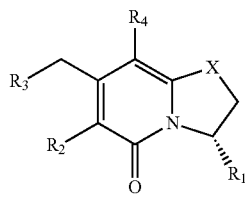

Formula IIa52

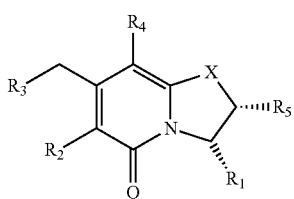

Formula IIa2

As described herein, X may be S, SO or $SO_2$ for the compounds of the present disclosure. Accordingly, when X is S the bicyclic ring structure contains a sulfide. When X is SO the bicyclic ring structure contains a sulphoxide. When X is $SO_2$ the bicyclic ring structure contains a sulphone.

By way of example, the compound of Formula IIa51 may exist as a compound of Formula IIa511, Formula IIa512 or Formula IIa513. $R_1$, $R_2$, $R_3$ and $R_4$, may have values as described herein. It will be appreciated that X is S in the compound of Formula IIa511, X is SO in the compound of Formula IIa512 and X is $SO_2$ in the compound of Formula IIa513. Further, albeit sulphoxides generally are depicted with a double bond between the sulfur atom and the oxygen atom such as in the compound of Formula IIa512 it is understood that the sulfur atom of the sulphoxide is a chiral center, and consequently may exhibit R or S stereochemistry at the sulphoxide chiral center.

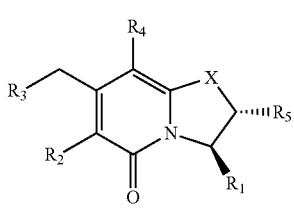

Formula IIa3

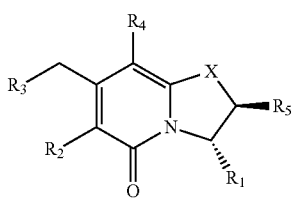

Formula IIa4

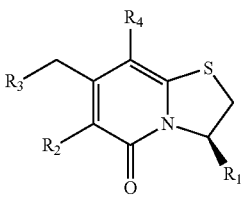

Formula IIa511

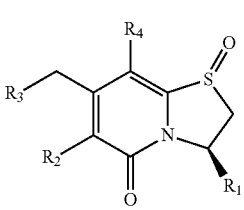

Formula IIa512

When $R_5$ is hydrogen the compound of Formula IIa may be depicted as a compound of Formula IIa5, Formula IIa51 or Formula IIa52. The compound of Formula IIa5 may be a racemate comprising the compounds of Formula IIa51 or Formula IIa52. For these compounds, $R_1$, $R_2$, $R_3$, $R_4$ and X may have values described herein.

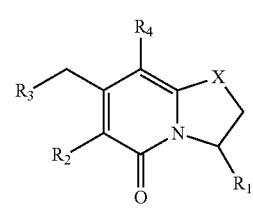

Formula IIa5

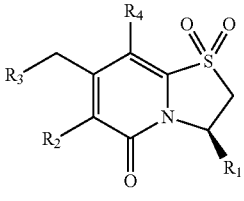

Formula IIa513

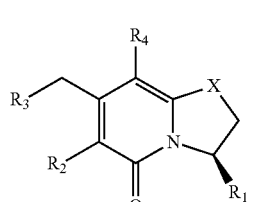

Formula IIa51

When $R_1$ is an acidic group AH such as C(O)OH, tetrazole or $C(O)NHSO_2R_7$ the compound of Formula II may form a salt with an antituberculosis drug such as isoniazide thereby providing a salt of Formula IIIa or Formula IIIb. For these compounds, $A^-$, $R_2$, $R_3$, $R_4$, $R_5$, $R_7$ and X may have values as described herein. It will be appreciated that the isoniazide of Formulas IIIa or Formula IIIb may be replaced with another drug against tuberculosis such as bedaquiline.

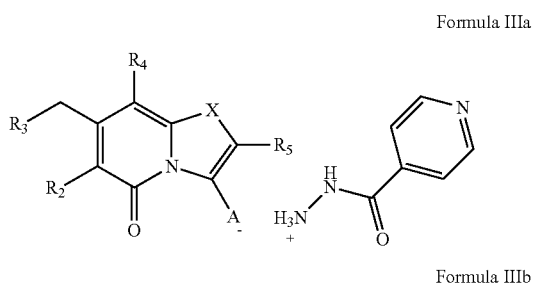

Formula IIIa

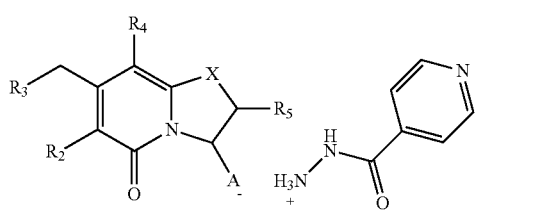

Formula IIIb

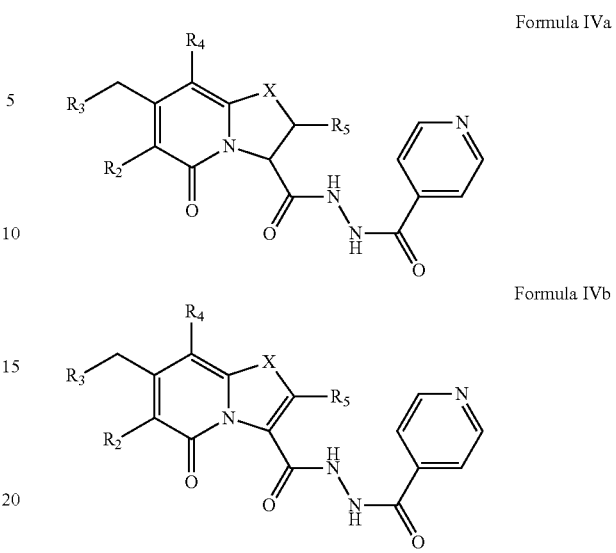

Formula IVa

Formula IVb

The present disclosure provides a salt of Formula IIIa and/or Formula IIIb. Further, it will be appreciated that the salt of Formula IIIb may exist as stereoisomers, and the present disclosure provides all such stereoisomers. The salt of Formula IIIa and/or Formula IIIb may be used in combination with a drug against tuberculosis such as isoniazid or bedaquiline. Alternatively, it may be used as such, optionally together with a pharmaceutical excipient diluent and/or carrier. For instance, the salt of Formula IIIa and/or Formula IIIb may be used in prevention of tuberculosis. In this document, the salts of Formula IIIa and/or Formula IIIb are also denominated compounds of Formula IIIa and/or Formula IIIb.

Further, the present disclosure provides a compound of Formula IV, or a pharmaceutically acceptable salt thereof. $R_2$, $R_3$, $R_4$, $R_5$ and X may have values as described herein. The compound of Formula IV may be provided by reacting isoniazide with a compound of Formula II, wherein $R_1$ is C(O)OH, of the present disclosure. In this reaction, $R_1$ may be transformed from C(O)OH into C(O)Cl prior to reaction with the compound of Formula IV. The compound of Formula IV may be provided in combination with isoniazid. Alternatively, it may be used as such in, optionally in combination with a pharmaceutical excipient, diluent and/or carrier.

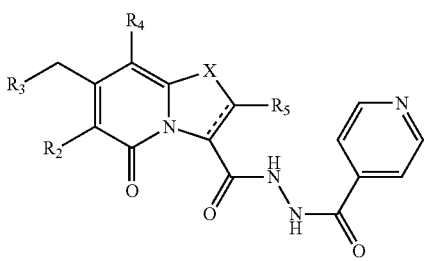

Formula IV

The compound of Formula IV may exist as a compound of Formula IVa or as a compound of Formula IVb. $R_2$, $R_3$, $R_4$, $R_5$ and X may have values as described herein. For instance, $R_5$ may be hydrogen and X may be S, SO or $SO_2$.

The compound of Formula IVa may exist as cis and trans stereoisomers. The present disclosure encompasses all these compounds which are denominated compounds of Formula IVa1, IVa2, IVa3 and IVa4, the chemical structures of which are shown in FIG. 5.

As an example of a compound of Formula IVa the present disclosure provides {7-Cyclopropyl-6-[(1-naphthyl)methyl]-4-oxo-1-thia-3a-aza-3-indanyl}(2-isonicotinoylhydrazino)formaldehyde.

Further, it will be appreciated that instead of the isoniazide moiety of Formula IV another drug against tuberculosis may be used.

The present disclosure further provides a combination comprising:

(i) a composition comprising or consisting of a drug against tuberculosis such as isonicotinylhydrazide or bedaquiline, or a pharmaceutically acceptable salt thereof, and (ii) a composition comprising or consisting of a compound of Formula II as described herein, or a pharmaceutically acceptable salt thereof.

Further, the combination described herein may be provided as a kit of parts. Thus, there is provided a kit of parts comprising:

(i) a composition comprising or consisting of a drug against tuberculosis such as isonicotinylhydrazide or bedaquiline, or a pharmaceutically acceptable salt thereof, and (ii) a composition comprising or consisting of a compound of Formula II as described herein, or a pharmaceutically acceptable salt thereof.

The combination described herein may be provided as a single composition comprising (i) a drug against tuberculosis such as isonicotinylhydrazide or bedaquiline, or a pharmaceutically acceptable salt thereof, and (ii) a compound of Formula II as described herein, or a pharmaceutically acceptable salt thereof.

For instance, the single composition may be provided as a tablet, lozenge or sirup.

The combination described herein such as the kit of parts may further comprise instructions for use. For instance, the instructions for use may be instructions for separate, sequential or simultaneous use of the (i) composition comprising or consisting of a drug against tuberculosis such as isonicotinylhydrazide, or a pharmaceutically acceptable salt thereof and the (ii) composition comprising or consisting of a compound of Formula II as described herein, or a pharmaceutically acceptable salt thereof.

The drug against tuberculosis described herein may be selected from at least one of the following: isoniazid, rifampicin, pyrazinamide, ethambutol, pretomanid, delamanid, bedaquiline, streptomycin, levofloxacin, moxifloxacin and ofloxacin, cycloserine, terizidone, thionamide, protionamide, clofazimine and-4-aminosalicylic acid. For instance, the drug against tuberculosis described herein may be selected from at least one of the following: isonicotinylhydrazide, bedaquiline, ethionamide, pretomanid, 4-aminosalisalicylic acid. In an example, the drug against tuberculosis may be isonicotinylhydrazide and/or bedaquiline, optionally in combination with at least one of ethambuthol, pyrazinamide, rifampicin. In a further example, the drug against tuberculosis may be as described elsewhere in this document. The combination of the present disclosure may further comprise a drug selected from the group consisting of rifampicin, pyrazinamide, ethambutol and 4-aminosalisalicylic acid. In particular, the combination of the present disclosure may further comprise a drug selected from the group consisting of rifampicin, pyrazinamide and ethambutol.

In an example, the drug against tuberculosis described herein may comprise or consist of isonicotinylhydrazide, rifampicin, pyrazinamide and ethambutol.

Further, in an example the drug against tuberculosis described herein does not solely consist of rifampicin, pyrazinamide or ethambutol. Thus, when rifampicin, pyrazinamide or ethambutol are used they may or should be used in combination with another drug against tuberculosis.

The combination described herein may comprise a compound of Formula II selected from at least one of:
(3R)-7-Cyclopropyl-6-[(1-naphthyl)methyl]-4-oxo-1-thia-3a-aza-3-indancarboxylic acid
(3R)-7-Cyclopropyl-4-oxo-6-{(7-thiabicyclo[4.3.0]nona-1,3,5,8-tetraen-8-yl)methyl}-1-thia-3a-aza-3-indancarboxylic acid
(3R)-7-Cyclopropyl-6-[(4-fluoro-1-naphthyl)methyl]-4-oxo-1-thia-3a-aza-3-indancarboxylic acid
(3R)-7-Cyclopropyl-6-[(4-methyl-1-naphthyl)methyl]-4-oxo-1-thia-3a-aza-3-indancarboxylic acid
(3S)-7-Cyclopropyl-6-[(1-naphthyl)methyl]-4-oxo-1-thia-3a-aza-3-indancarboxylic acid
5-Cyclopropyl-4-[(1-naphthyl)methyl]-2-oxo-8-(3-thienyl)-7-thia-1-azabicyclo[4.3.0]nona-3,5,8-triene-9-carboxylic acid
(3R)-7-Cyclopropyl-6-[(1-naphthyloxy)methyl]-4-oxo-1-thia-3a-aza-3-indancarboxylic acid
(3R)-7-Cyclopropyl-6-[(2-fluoro-5-methyl-phenyl)methyl]-4-oxo-1-thia-3a-aza-3-indancarboxylic acid
(3R)-7-Cyclopropyl-4-oxo-6-[(2,3-xylyl)methyl]-1-thia-3a-aza-3-indancarboxylic acid
(3R)-7-Methyl-6-[(1-naphthyl)methyl]-4-oxo-1-thia-3a-aza-3-indancarboxylic acid
(N-Methylmethoxyamino){(3R)-7-cyclopropyl-6-[(1-naphthyl)methyl]-4-oxo-1-thia-3a-aza-3-indanyl}formaldehyde
(3R)-7-Cyclopropyl-6-[(1-naphthyl)methyl]-3-(1H-1,2,3,4-tetrazol-5-yl)-1-thia-3a-aza-4-indanone
5-Cyclopropyl-4-[(1-naphthyl)methyl]-2-oxo-8-phenyl-7-thia-1-azabicyclo[4.3.0]nona-3,5,8-triene-9-carboxylic acid
5-Cyclopropyl-4-[(1-naphthyl)methyl]-2-oxo-8-(m-tolyl)-7-thia-1-azabicyclo[4.3.0]nona-3,5,8-triene-9-carboxylic acid
(3R)-7-Cyclopropyl-6-[(2-naphthyl)methyl]-4-oxo-1-thia-3a-aza-3-indancarboxylic acid
(3R)-7-Cyclopropyl-3-(hydroxymethyl)-6-[(1-naphthyl)methyl]-1-thia-3a-aza-4-indanone
(3R)-6-[(1-Naphthyl)methyl]-4-oxo-7-(2-thienyl)-1-thia-3a-aza-3-indancarboxylic acid
5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid
8-Benzyl-5-cyclopropyl-4-[(1-naphthyl)methyl]-2-oxo-7-thia-1-azabicyclo[4.3.0]nona-3,5,8-triene-9-carboxylic acid
(3R)-7-Cyclopropyl-6-[(2,3-dichlorophenyl)methyl]-4-oxo-1-thia-3a-aza-3-indancarboxylic acid
(3R)-7-Cyclopropyl-6-[(1-naphthyl)methyl]-4-oxo-1-thia-3a-aza-3-indancarboxamide
{(3R)-7-Cyclopropyl-6-[(1-naphthyl)methyl]-4-oxo-1-thia-3a-aza-3-indanyl}(phenylsulfonylamino)formaldehyde
(3R)-7-Isopropyl-6-[(1-naphthyl)methyl]-4-oxo-1-thia-3a-aza-3-indancarboxylic acid
(3R)-7-Cyclopropyl-6-methyl-4-oxo-1-thia-3a-aza-3-indancarboxylic acid
(3R)-6-[(p-Chlorophenyl)methyl]-7-cyclopropyl-4-oxo-1-thia-3a-aza-3-indancarboxylic acid
{(3R)-7-Cyclopropyl-6-[(1-naphthyl)methyl]-4-oxo-1-thia-3a-aza-3-indanyl}(methylsulfonylamino)formaldehyde
(3R)-7-Cyclopropyl-4-oxo-6-[(m-tolyl)methyl]-1-thia-3a-aza-3-indancarboxylic acid
(3R)-7-Isopropyl-4-oxo-6-[2-(m-tolyl)ethyl]-1-thia-3a-aza-3-indancarboxylic acid
7-(1-Methyl-1H-indol-3-yl)-6-[(1-naphthyloxy)methyl]-4-oxo-1-thia-3a-aza-3-indancarboxylic acid
(3R)-6-[(4-Bromo-1-naphthyl)methyl]-7-cyclopropyl-4-oxo-1-thia-3a-aza-3-indancarboxylic acid
7-Cyclopropyl-6-[(1-naphthyl)methyl]-1-thia-3a-aza-4-indanone
(3R)-7-Cyclopropyl-5-(hydroxymethyl)-6-[(1-naphthyl)methyl]-4-oxo-1-thia-3a-aza-3-indancarboxylic acid
(3S)-3-Amino-7-cyclopropyl-6-[(1-naphthyl)methyl]-1-thia-3a-aza-4-indanone
(2R,3R)-7-Cyclopropyl-6-[(1-naphthyl)methyl]-4-oxo-2-phenyl-1-thia-3a-aza-3-indancarboxylic acid
(2S,3R)-7-Cyclopropyl-2-methoxy-6-[(1-naphthyl)methyl]-4-oxo-1-thia-3a-aza-3-indancarboxylic acid
7-Cyclopropyl-4-oxo-6-{[m-(trifluoromethyl)phenyl]methyl}-1-thia-3a-aza-3-indancarboxylic acid
2-{2-[1-(Hydroxymethyl)propylamino]ethylamino}butyl 7-cyclopropyl-6-[(1-naphthyl)methyl]-4-oxo-1-thia-3a-aza-3-indancarboxylate
{7-Cyclopropyl-6-[(1-naphthyl)methyl]-4-oxo-1-thia-3a-aza-3-indanyl}(2-isonicotinoylhydrazino)formaldehyde
7-Cyclopropyl-6-[(4-methoxy-1-naphthyl)methyl]-4-oxo-1-thia-3a-aza-3-indancarboxylic acid
(3R)-7-(Dimethylamino)-6-[(1-naphthyl)methyl]-4-oxo-1-thia-3a-aza-3-indancarboxylic acid
(3R)-5-Bromo-7-cyclopropyl-6-[(1-naphthyl)methyl]-4-oxo-1-thia-3a-aza-3-indancarboxylic acid
7-Cyclopropyl-6-[(1-naphthyl)methyl]-1,1-dioxo-4-oxo-1-thia-3a-aza-3-indancarboxylic acid
(3R)-7-Cyclopropyl-4-oxo-6-[(2,3-xylidino)methyl]-1-thia-3a-aza-3-indancarboxylic acid
7-Cyclopropyl-6-[(1-naphthyl)methyl]-1-oxo-4-oxo-1-thia-3a-aza-3-indancarboxylic acid
(3R)-7-Ethoxy-6-[(1-naphthyl)methyl]-4-oxo-1-thia-3a-aza-3-indancarboxylic acid
(3R)-6-[(1-Naphthyl)methyl]-4-oxo-7-(trifluoromethyl)-1-thia-3a-aza-3-indancarboxylic acid (3R)-7-Isobutoxy-6-[(1-naphthyl)methyl]-4-oxo-1-thia-3a-aza-3-indancarboxylic acid (3R)-7-Cyclopropyl-6-[(2-methoxy-1-naphthyl)methyl]-4-oxo-1-thia-3a-aza-3-indancarboxylic acid (3R)-7-(Cyclopropylmethoxy)-6-[(1-naphthyl)methyl]-4-oxo-1-thia-3a-aza-3-indancarboxylic acid 7-Cyclopropyl-6-[(2-methyl-1-aza-2-bora-1H-naphth-5-yl)methyl]-4-oxo-1-thia-3a-aza-3-indancarboxylic acid 7-Cyclopropyl-6-[(2-methyl-1-aza-2-bora-1H-naphth-5-yloxy)methyl]-4-oxo-1-thia-3a-aza-3-indancarboxylic acid 7-Cyclopropyl-6-[(2-methyl-1-aza-2-bora-1H-naphth-8-yl)methyl]-4-oxo-1-thia-3a-aza-3-indancarboxylic acid 7-Cyclopropyl-6-[(2-methyl-1-aza-2-bora-1H-naphth-8-yloxy)methyl]-4-oxo-1-thia-3a-aza-3-indancarboxylic acid or a pharmaceutically acceptable salt of any of the foregoing compounds.

In a further example, the combination described herein may comprise a compound of Formula II selected from at least one of:

(3R)-7-Cyclopropyl-6-[(1-naphthyl)methyl]-4-oxo-1-thia-3a-aza-3-indancarboxylic acid (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid (3R)-7-Cyclopropyl-6-[(4-fluoro-1-naphthyl)methyl]-4-oxo-1-thia-3a-aza-3-indancarboxylic acid (3R)-7-Cyclopropyl-6-[(4-methyl-1-naphthyl)methyl]-4-oxo-1-thia-3a-aza-3-indancarboxylic acid (3S)-7-Cyclopropyl-6-[(1-naphthyl)methyl]-4-oxo-1-thia-3a-aza-3-indancarboxylic acid (3R)-7-Cyclopropyl-6-[(1-naphthyloxy)methyl]-4-oxo-1-thia-3a-aza-3-indancarboxylic acid (3R)-7-Cyclopropyl-6-[(2-fluoro-5-methyl-phenyl)methyl]-4-oxo-1-thia-3a-aza-3-indancarboxylic acid (3R)-7-Cyclopropyl-4-oxo-6-[(2,3-xylyl)methyl]-1-thia-3a-aza-3-indancarboxylic acid (3R)-7-Methyl-6-[(1-naphthyl)methyl]-4-oxo-1-thia-3a-aza-3-indancarboxylic acid (N-Methylmethoxyamino){(3R)-7-cyclopropyl-6-[(1-naphthyl)methyl]-4-oxo-1-thia-3a-aza-3-indanyl}formaldehyde (3R)-7-Cyclopropyl-6-[(1-naphthyl)methyl]-3-(1H-1,2,3,4-tetrazol-5-yl)-1-thia-3a-aza-4-indanone (3R)-7-Cyclopropyl-6-[(2-naphthyl)methyl]-4-oxo-1-thia-3a-aza-3-indancarboxylic acid (3R)-7-Cyclopropyl-3-(hydroxymethyl)-6-[(1-naphthyl)methyl]-1-thia-3a-aza-4-indanone (3R)-6-[(1-Naphthyl)methyl]-4-oxo-7-(2-thienyl)-1-thia-3a-aza-3-indancarboxylic acid (3R)-7-Cyclopropyl-6-[(2,3-dichlorophenyl)methyl]-4-oxo-1-thia-3a-aza-3-indancarboxylic acid (3R)-7-Cyclopropyl-6-[(1-naphthyl)methyl]-4-oxo-1-thia-3a-aza-3-indancarboxamide {(3R)-7-Cyclopropyl-6-[(1-naphthyl)methyl]-4-oxo-1-thia-3a-aza-3-indanyl}(phenylsulfonylamino)formaldehyde (3R)-7-Isopropyl-6-[(1-naphthyl)methyl]-4-oxo-1-thia-3a-aza-3-indancarboxylic acid (3R)-7-Cyclopropyl-6-methyl-4-oxo-1-thia-3a-aza-3-indancarboxylic acid (3R)-6-[(p-Chlorophenyl)methyl]-7-cyclopropyl-4-oxo-1-thia-3a-aza-3-indancarboxylic acid {(3R)-7-Cyclopropyl-6-[(1-naphthyl)methyl]-4-oxo-1-thia-3a-aza-3-indanyl}(methylsulfonylamino)formaldehyde (3R)-7-Cyclopropyl-4-oxo-6-[(m-tolyl)methyl]-1-thia-3a-aza-3-indancarboxylic acid (3R)-7-Isopropyl-4-oxo-6-[2-(m-tolyl)ethyl]-1-thia-3a-aza-3-indancarboxylic acid 7-(1-Methyl-1H-indol-3-yl)-6-[(1-naphthyloxy)methyl]-4-oxo-1-thia-3a-aza-3-indancarboxylic acid (3R)-6-[(4-Bromo-1-naphthyl)methyl]-7-cyclopropyl-4-oxo-1-thia-3a-aza-3-indancarboxylic acid 7-Cyclopropyl-6-[(1-naphthyl)methyl]-1-thia-3a-aza-4-indanone (3R)-7-Cyclopropyl-5-(hydroxymethyl)-6-[(1-naphthyl)methyl]-4-oxo-1-thia-3a-aza-3-indancarboxylic acid (3S)-3-Amino-7-cyclopropyl-6-[(1-naphthyl)methyl]-1-thia-3a-aza-4-indanone (2R,3R)-7-Cyclopropyl-6-[(1-naphthyl)methyl]-4-oxo-2-phenyl-1-thia-3a-aza-3-indancarboxylic acid (2S,3R)-7-Cyclopropyl-2-methoxy-6-[(1-naphthyl)methyl]-4-oxo-1-thia-3a-aza-3-indancarboxylic acid 7-Cyclopropyl-4-oxo-6-{[m-(trifluoromethyl)phenyl]methyl}-1-thia-3a-aza-3-indancarboxylic acid 2-{2-[1-(Hydroxymethyl)propylamino]ethylamino}butyl 7-cyclopropyl-6-[(1-naphthyl)methyl]-4-oxo-1-thia-3a-aza-3-indancarboxylate {7-Cyclopropyl-6-[(1-naphthyl)methyl]-4-oxo-1-thia-3a-aza-3-indanyl}(2-isonicotinoylhydrazino)formaldehyde 7-Cyclopropyl-6-[(4-methoxy-1-naphthyl)methyl]-4-oxo-1-thia-3a-aza-3-indancarboxylic acid (3R)-7-(Dimethylamino)-6-[(1-naphthyl)methyl]-4-oxo-1-thia-3a-aza-3-indancarboxylic acid (3R)-5-Bromo-7-cyclopropyl-6-[(1-naphthyl)methyl]-4-oxo-1-thia-3a-aza-3-indancarboxylic acid 7-Cyclopropyl-6-[(1-naphthyl)methyl]-1,1-dioxo-4-oxo-1-thia-3a-aza-3-indancarboxylic acid (3R)-7-Cyclopropyl-4-oxo-6-[(2,3-xylidino)methyl]-1-thia-3a-aza-3-indancarboxylic acid 7-Cyclopropyl-6-[(1-naphthyl)methyl]-1-oxo-4-oxo-1-thia-3a-aza-3-indancarboxylic acid (3R)-7-Ethoxy-6-[(1-naphthyl)methyl]-4-oxo-1-thia-3a-aza-3-indancarboxylic acid (3R)-6-[(1-Naphthyl)methyl]-4-oxo-7-(trifluoromethyl)-1-thia-3a-aza-3-indancarboxylic acid (3R)-7-Isobutoxy-6-[(1-naphthyl)methyl]-4-oxo-1-thia-3a-aza-3-indancarboxylic acid (3R)-7-Cyclopropyl-6-[(2-methoxy-1-naphthyl)methyl]-4-oxo-1-thia-3a-aza-3-indancarboxylic acid (3R)-7-(Cyclopropylmethoxy)-6-[(1-naphthyl)methyl]-4-oxo-1-thia-3a-aza-3-indancarboxylic acid 7-Cyclopropyl-6-[(2-methyl-1-aza-2-bora-1H-naphth-5-yl)methyl]-4-oxo-1-thia-3a-aza-3-indancarboxylic acid 7-Cyclopropyl-6-[(2-methyl-1-aza-2-bora-1H-naphth-5-yloxy)methyl]-4-oxo-1-thia-3a-aza-3-indancarboxylic acid 7-Cyclopropyl-6-[(2-methyl-1-aza-2-bora-1H-naphth-8-yl)methyl]-4-oxo-1-thia-3a-aza-3-indancarboxylic acid 7-Cyclopropyl-6-[(2-methyl-1-aza-2-bora-1H-naphth-8-yloxy)methyl]-4-oxo-1-thia-3a-aza-3-indancarboxylic acid or a pharmaceutically acceptable salt of any of the foregoing compounds.

In still a further example, the combination described herein may comprise a compound of Formula II selected from at least one of:

5-Cyclopropyl-4-[(1-naphthyl)methyl]-2-oxo-8-(3-thienyl)-7-thia-1-azabicyclo[4.3.0]nona-3,5,8-triene-9-carboxylic acid 5-Cyclopropyl-4-[(1-naphthyl)methyl]-2-oxo-8-phenyl-7-thia-1-azabicyclo[4.3.0]nona-3,5,8-triene-9-carboxylic acid 5-Cyclopropyl-4-[(1-naphthyl)methyl]-2-oxo-8-(m-tolyl)-7-thia-1-azabicyclo[4.3.0]nona-3,5,8-triene-9-carboxylic acid 5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid 8-Benzyl-5-cyclopropyl-4-[(1-naphthyl)methyl]-2-oxo-7-thia-1-azabicyclo[4.3.0]nona-3,5,8-triene-9-carboxylic acid or a pharmaceutically acceptable salt of any of the foregoing compounds.

In a further example, the combination described herein may comprise a compound of Formula II selected from at least one of:

(3R)-7-Cyclopropyl-6-[(1-naphthyl)methyl]-4-oxo-1-thia-3a-aza-3-indancarboxylic acid (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid (3R)-7-Cyclopropyl-6-[(4-fluoro-1-naphthyl)methyl]-4-oxo-1-thia-3a-aza-3-indancarboxylic acid (3R)-7-Cyclopropyl-6-[(4-methyl-1-naphthyl)methyl]-4-oxo-1-thia-3a-aza-3-indancarboxylic acid (3S)-7-Cyclopropyl-6-[(1-naphthyl)methyl]-4-oxo-1-thia-3a-aza-3-indancarboxylic acid 5-Cyclopropyl-4-[(1-naphthyl)methyl]-2-oxo-8-(3-thienyl)-7-thia-1-azabicyclo[4.3.0]nona-3,5,8-triene-9-carboxylic acid (3R)-7-Cyclopropyl-6-[(1-naphthyloxy)methyl]-4-oxo-1-thia-3a-aza-3-indancarboxylic acid (3R)-7-Cyclopropyl-6-[(2-fluoro-5-methyl-phenyl)methyl]-4-oxo-1-thia-3a-aza-3-indancarboxylic acid (3R)-7-Cyclopropyl-4-oxo-6-[(2,3-xylyl)methyl]-1-thia-3a-aza-3-indancarboxylic acid (3R)-7-Methyl-6-[(1-naphthyl)methyl]-4-oxo-1-thia-3a-aza-3-indancarboxylic acid (N-Methylmethoxyamino){(3R)-7-cyclopropyl-6-[(1-naphthyl)methyl]-4-oxo-1-thia-3a-aza-3-indanyl}formaldehyde (3R)-7-Cyclopropyl-6-[(1-naphthyl)methyl]-3-(1H-1,2,3,4-tetrazol-5-yl)-1-thia-3a-aza-4-indanone 5-Cyclopropyl-4-[(1-naphthyl)methyl]-2-oxo-8-phenyl-7-thia-1-azabicyclo[4.3.0]nona-3,5,8-triene-9-carboxylic acid 5-Cyclopropyl-4-[(1-naphthyl)methyl]-2-oxo-8-(m-tolyl)-7-thia-1-azabicyclo[4.3.0]nona-3,5,8-triene-9-carboxylic acid (3R)-7-Cyclopropyl-6-[(2-naphthyl)methyl]-4-oxo-1-thia-3a-aza-3-indancarboxylic acid (3R)-7-Cyclopropyl-3-(hydroxymethyl)-6-[(1-naphthyl)methyl]-1-thia-3a-aza-4-indanone (3R)-6-[(1-Naphthyl)methyl]-4-oxo-7-(2-thienyl)-1-thia-3a-aza-3-indancarboxylic acid 5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid 8-Benzyl-5-cyclopropyl-4-[(1-naphthyl)methyl]-2-oxo-7-thia-1-azabicyclo[4.3.0]nona-3,5,8-triene-9-carboxylic acid (3R)-7-Cyclopropyl-6-[(2,3-dichlorophenyl)methyl]-4-oxo-1-thia-3a-aza-3-indancarboxylic acid (3R)-7-Cyclopropyl-6-[(1-naphthyl)methyl]-4-oxo-1-thia-3a-aza-3-indancarboxamide {(3R)-7-Cyclopropyl-6-[(1-naphthyl)methyl]-4-oxo-1-thia-3a-aza-3-indanyl}(phenylsulfonylamino)formaldehyde (3R)-7-Isopropyl-6-[(1-naphthyl)methyl]-4-oxo-1-thia-3a-aza-3-indancarboxylic acid (3R)-7-Cyclopropyl-6-methyl-4-oxo-1-thia-3a-aza-3-indancarboxylic acid (3R)-6-[(p-Chlorophenyl)methyl]-7-cyclopropyl-4-oxo-1-thia-3a-aza-3-indancarboxylic acid {(3R)-7-Cyclopropyl-6-[(1-naphthyl)methyl]-4-oxo-1-thia-3a-aza-3-indanyl}(methylsulfonylamino)formaldehyde (3R)-7-Cyclopropyl-4-oxo-6-[(m-tolyl)methyl]-1-thia-3a-aza-3-indancarboxylic acid (3R)-7-Isopropyl-4-oxo-6-[2-(m-tolyl)ethyl]-1-thia-3a-aza-3-indancarboxylic acid 7-(1-Methyl-1H-indol-3-yl)-6-[(1-naphthyloxy)methyl]-4-oxo-1-thia-3a-aza-3-indancarboxylic acid (3R)-6-[(4-Bromo-1-naphthyl)methyl]-7-cyclopropyl-4-oxo-1-thia-3a-aza-3-indancarboxylic acid 7-Cyclopropyl-6-[(1-naphthyl)methyl]-1-thia-3a-aza-4-indanone (3R)-7-Cyclopropyl-5-(hydroxymethyl)-6-[(1-naphthyl)methyl]-4-oxo-1-thia-3a-aza-3-indancarboxylic acid (3S)-3-Amino-7-cyclopropyl-6-[(1-naphthyl)methyl]-1-thia-3a-aza-4-indanone (2R,3R)-7-Cyclopropyl-6-[(1-naphthyl)methyl]-4-oxo-2-phenyl-1-thia-3a-aza-3-indancarboxylic acid (2S,3R)-7-Cyclopropyl-2-methoxy-6-[(1-naphthyl)methyl]-4-oxo-1-thia-3a-aza-3-indancarboxylic acid or a pharmaceutically acceptable salt of any of the foregoing compounds.

In a further example, the combination described herein may comprise a compound of Formula II selected from at least one of:

(3R)-7-Cyclopropyl-6-[(1-naphthyl)methyl]-4-oxo-1-thia-3a-aza-3-indancarboxylic acid (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid (3R)-7-Cyclopropyl-6-[(4-fluoro-1-naphthyl)methyl]-4-oxo-1-thia-3a-aza-3-indancarboxylic acid (3R)-7-Cyclopropyl-6-[(4-methyl-1-naphthyl)methyl]-4-oxo-1-thia-3a-aza-3-indancarboxylic acid (3S)-7-Cyclopropyl-6-[(1-naphthyl)methyl]-4-oxo-1-thia-3a-aza-3-indancarboxylic acid 5-Cyclopropyl-4-[(1-naphthyl)methyl]-2-oxo-8-(3-thienyl)-7-thia-1-azabicyclo[4.3.0]nona-3,5,8-triene-9-carboxylic acid (3R)-7-Cyclopropyl-6-[(1-naphthyloxy)methyl]-4-oxo-1-thia-3a-aza-3-indancarboxylic acid (3R)-7-Cyclopropyl-6-[(2-fluoro-5-methyl-phenyl)methyl]-4-oxo-1-thia-3a-aza-3-indancarboxylic acid (3R)-7-Cyclopropyl-4-oxo-6-[(2,3-xylyl)methyl]-1-thia-3a-aza-3-indancarboxylic acid (3R)-7-Methyl-6-[(1-naphthyl)methyl]-4-oxo-1-thia-3a-aza-3-indancarboxylic acid (N-Methylmethoxyamino){(3R)-7-cyclopropyl-6-[(1-naphthyl)methyl]-4-oxo-1-thia-3a-aza-3-indanyl}formaldehyde (3R)-7-Cyclopropyl-6-[(1-naphthyl)methyl]-3-(1H-1,2,3,4-tetrazol-5-yl)-1-thia-3a-aza-4-indanone 5-Cyclopropyl-4-[(1-naphthyl)methyl]-2-oxo-8-phenyl-7-thia-1-azabicyclo[4.3.0]nona-3,5,8-triene-9-carboxylic acid 5-Cyclopropyl-4-[(1-naphthyl)methyl]-2-oxo-8-(m-tolyl)-7-thia-1-azabicyclo[4.3.0]nona-3,5,8-triene-9-carboxylic acid (3R)-7-Cyclopropyl-6-[(2-naphthyl)methyl]-4-oxo-1-thia-3a-aza-3-indancarboxylic acid (3R)-7-Cyclopropyl-3-(hydroxymethyl)-6-[(1-naphthyl)methyl]-1-thia-3a-aza-4-indanone (3R)-6-[(1-Naphthyl)methyl]-4-oxo-7-(2-thienyl)-1-thia-3a-aza-3-indancarboxylic acid 5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid 8-Benzyl-5-cyclopropyl-4-[(1-naphthyl)methyl]-2-oxo-7-thia-1-azabicyclo[4.3.0]nona-3,5,8-triene-9-carboxylic acid (3R)-7-Cyclopropyl-6-[(2,3-dichlorophenyl)methyl]-4-oxo-1-thia-3a-aza-3-indancarboxylic acid (3R)-7-Cyclopropyl-6-[(1-naphthyl)methyl]-4-oxo-1-thia-3a-aza-3-indancarboxamide {(3R)-7-Cyclopropyl-6-[(1-naphthyl)methyl]-4-oxo-1-thia-3a-aza-3-indanyl}(phenylsulfonylamino)formaldehyde (3R)-7-Isopropyl-6-[(1-naphthyl)methyl]-4-oxo-1-thia-3a-aza-3-indancarboxylic acid (3R)-7-Cyclopropyl-6-methyl-4-oxo-1-thia-3a-aza-3-indancarboxylic acid (3R)-6-[(p-Chlorophenyl)methyl]-7-cyclopropyl-4-oxo-1-thia-3a-aza-3-indancarboxylic acid {(3R)-7-Cyclopropyl-6-[(1-naphthyl)methyl]-4-oxo-1-thia-3a-aza-3-indanyl}(methylsulfonylamino)formaldehyde (3R)-7-Cyclopropyl-4-oxo-6-[(m-tolyl)methyl]-1-thia-3a-aza-3-indancarboxylic acid (3R)-7-Isopropyl-4-oxo-6-[2-(m-tolyl)ethyl]-1-thia-3a-aza-3-indancarboxylic acid 7-(1-Methyl-1H-indol-3-yl)-6-[(1-naphthyloxy)methyl]-4-oxo-1-thia-3a-aza-3-indancarboxylic acid (3R)-6-[(4-Bromo-1-naphthyl)methyl]-7-cyclopropyl-4-oxo-1-thia-3a-aza-3-indancarboxylic acid 7-Cyclopropyl-6-[(1-naphthyl)methyl]-1-thia-3a-aza-4-indanone (3R)-7-Cyclopropyl-5-(hydroxymethyl)-6-[(1-naphthyl)methyl]-4-oxo-1-thia-3a-aza-3-indancarboxylic acid (3S)-3-Amino-7-cyclopropyl-6-[(1-naphthyl)methyl]-1-thia-3a-aza-4-indanone (2R,3R)-7-Cyclopropyl-6-[(1-naphthyl)methyl]-4-oxo-2-phenyl-1-thia-3a-aza-3-indancarboxylic acid (2S,3R)-7-Cyclopropyl-2-methoxy-6-[(1-naphthyl)methyl]-4-oxo-1-thia-3a-aza-3-indancarboxylic acid or a pharmaceutically acceptable salt of any of the foregoing compounds.

In a further example, the present disclosure provides a compound of Formula II, which may be part of and/or used in the combination described herein, said compound being selected from at least one of:

7-Cyclopropyl-4-oxo-6-{[m-(trifluoromethyl)phenyl]methyl}-1-thia-3a-aza-3-indancarboxylic acid 2-{2-[1-(Hydroxymethyl)propylamino]ethylamino}butyl 7-cyclopropyl-6-[(1-naphthyl)methyl]-4-oxo-1-thia-3a-aza-3-indancarboxylate {7-Cyclopropyl-6-[(1-naphthyl)methyl]-4-oxo-1-thia-3a-aza-3-indanyl}(2-isonicotinoylhydrazino)formaldehyde 7-Cyclopropyl-6-[(4-methoxy-1-naphthyl)methyl]-4-oxo-1-thia-3a-aza-3-indancarboxylic acid (3R)-7-(Dimethylamino)-6-[(1-naphthyl)methyl]-4-oxo-1-thia-3a-aza-3-indancarboxylic acid (3R)-5-Bromo-7-cyclopropyl-6-[(1-naphthyl) methyl]-4-oxo-1-thia-3a-aza-3-indancarboxylic acid 7-Cyclopropyl-6-[(1-naphthyl)methyl]-1,1-dioxo-4-oxo-1-thia-3a-aza-3-indancarboxylic acid (3R)-7-Cyclopropyl-4-oxo-6-[(2,3-xylidino)methyl]-1-thia-3a-aza-3-indancarboxylic acid 7-Cyclopropyl-6-[(1-naphthyl)methyl]-1-oxo-4-oxo-1-thia-3a-aza-3-indancarboxylic acid (3R)-7-Ethoxy-6-[(1-naphthyl)methyl]-4-oxo-1-thia-3a-aza-3-indancarboxylic acid (3R)-6-[(1-Naphthyl)methyl]-4-oxo-7-(trifluoromethyl)-1-thia-3a-aza-3-indancarboxylic acid (3R)-7-Isobutoxy-6-[(1-naphthyl)methyl]-4-oxo-1-thia-3a-aza-3-indancarboxylic acid (3R)-7-Cyclopropyl-6-[(2-methoxy-1-naphthyl)methyl]-4-oxo-1-thia-3a-aza-3-indancarboxylic acid (3R)-7-(Cyclopropylmethoxy)-6-[(1-naphthyl)methyl]-4-oxo-1-thia-3a-aza-3-indancarboxylic acid 7-Cyclopropyl-6-[(2-methyl-1-aza-2-bora-1H-naphth-5-yl)methyl]-4-oxo-1-thia-3a-aza-3-indancarboxylic acid 7-Cyclopropyl-6-[(2-methyl-1-aza-2-bora-1H-naphth-5-yloxy)methyl]-4-oxo-1-thia-3a-aza-3-indancarboxylic acid 7-Cyclopropyl-6-[(2-methyl-1-aza-2-bora-1H-naphth-8-yl)methyl]-4-oxo-1-thia-3a-aza-3-indancarboxylic acid 7-Cyclopropyl-6-[(2-methyl-1-aza-2-bora-1H-naphth-8-yloxy)methyl]-4-oxo-1-thia-3a-aza-3-indancarboxylic acid or a pharmaceutically acceptable salt of any of the foregoing compounds. There is also provided a compound of Formula II as described in this paragraph as such.

In a further example, the combination described herein may comprise a compound of Formula II selected from at least one of:

(3R)-7-Cyclopropyl-6-[(1-naphthyl)methyl]-4-oxo-1-thia-3a-aza-3-indancarboxylic acid 7-Cyclopropyl-4-oxo-6-{[m-(trifluoromethyl)phenyl]methyl}-1-thia-3a-aza-3-indancarboxylic acid (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid (3R)-7-Cyclopropyl-6-[(4-fluoro-1-naphthyl)methyl]-4-oxo-1-thia-3a-aza-3-indancarboxylic acid (3R)-7-Cyclopropyl-6-[(4-methyl-1-naphthyl)methyl]-4-oxo-1-thia-3a-aza-3-indancarboxylic acid (3S)-7-Cyclopropyl-6-[(1-naphthyl)methyl]-4-oxo-1-thia-3a-aza-3-indancarboxylic acid (3R)-7-Cyclopropyl-4-oxo-6-[(m-tolyl)methyl]-1-thia-3a-aza-3-indancarboxylic acid 2-{2-[1-(Hydroxymethyl)propylamino]ethylamino}butyl 7-cyclopropyl-6-[(1-naphthyl)methyl]-4-oxo-1-thia-3a-aza-3-indancarboxylate {7-Cyclopropyl-6-[(1-naphthyl)methyl]-4-oxo-1-thia-3a-aza-3-indanyl}(2-isonicotinoylhydrazino)formaldehyde (3R)-7-Cyclopropyl-6-[(2-naphthyl)methyl]-4-oxo-1-thia-3a-aza-3-indancarboxylic acid (3R)-7-Cyclopropyl-6-[(2-fluoro-5-methyl-phenyl)methyl]-4-oxo-1-thia-3a-aza-3-indancarboxylic acid (3R)-7-Methyl-6-[(1-naphthyl)methyl]-4-oxo-1-thia-3a-aza-3-indancarboxylic acid (3R)-7-Cyclopropyl-6-[(2,3-dichlorophenyl)methyl]-4-oxo-1-thia-3a-aza-3-indancarboxylic acid or a pharmaceutically acceptable salt of any of the foregoing compounds.

In a further example, the combination described herein may comprise a compound of Formula II selected from at least one of:

(3R)-7-Cyclopropyl-6-[(1-naphthyl)methyl]-4-oxo-1-thia-3a-aza-3-indancarboxylic acid 7-Cyclopropyl-4-oxo-6-{[m-(trifluoromethyl)phenyl]methyl}-1-thia-3a-aza-3-indancarboxylic acid (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid (3R)-7-Cyclopropyl-6-[(4-fluoro-1-naphthyl)methyl]-4-oxo-1-thia-3a-aza-3-indancarboxylic acid (3R)-7-Cyclopropyl-6-[(4-methyl-1-naphthyl)methyl]-4-oxo-1-thia-3a-aza-3-indancarboxylic acid (3S)-7-Cyclopropyl-6-[(1-naphthyl)methyl]-4-oxo-1-thia-3a-aza-3-indancarboxylic acid (3R)-7-Cyclopropyl-4-oxo-6-[(m-tolyl)methyl]-1-thia-3a-aza-3-indancarboxylic acid 2-{2-[1-(Hydroxymethyl)propylamino]ethylamino}butyl 7-cyclopropyl-6-[(1-naphthyl)methyl]-4-oxo-1-thia-3a-aza-3-indancarboxylate {7-Cyclopropyl-6-[(1-naphthyl)methyl]-4-oxo-1-thia-3a-aza-3-indanyl}(2-isonicotinoylhydrazino)formaldehyde (3R)-7-Cyclopropyl-6-[(2-naphthyl)methyl]-4-oxo-1-thia-3a-aza-3-indancarboxylic acid 7-Cyclopropyl-6-[(4-methoxy-1-naphthyl)methyl]-4-oxo-1-thia-3a-aza-3-indancarboxylic acid 5-Cyclopropyl-4-[(1-naphthyl)methyl]-2-oxo-8-(3-thienyl)-7-thia-1-azabicyclo[4.3.0]nona-3,5,8-triene-9-carboxylic acid (3R)-7-Cyclopropyl-6-[(1-naphthyloxy)methyl]-4-oxo-1-thia-3a-aza-3-indancarboxylic acid (3R)-7-Cyclopropyl-6-[(2-fluoro-5-methyl-phenyl)methyl]-4-oxo-1-thia-3a-aza-3-indancarboxylic acid (3R)-7-Cyclopropyl-4-oxo-6-[(2,3-xylyl)methyl]-1-thia-3a-aza-3-indancarboxylic acid (3R)-7-Methyl-6-[(1-naphthyl)methyl]-4-oxo-1-thia-3a-aza-3-indancarboxylic acid (3R)-7-(Dimethylamino)-6-[(1-naphthyl)methyl]-4-oxo-1-thia-3a-aza-3-indancarboxylic acid 5-Cyclopropyl-4-[(1-naphthyl)methyl]-2-oxo-8-phenyl-7-thia-1-azabicyclo[4.3.0]nona-3,5,8-triene-9-carboxylic acid 5-Cyclopropyl-4-[(1-naphthyl)methyl]-2-oxo-8-(m-tolyl)-7-thia-1-azabicyclo[4.3.0]nona-3,5,8-triene-9-carboxylic acid (3R)-7-Cyclopropyl-6-[(2,3-dichlorophenyl)methyl]-4-oxo-1-thia-3a-aza-3-indancarboxylic acid (3R)-7-Cyclopropyl-6-[(1-naphthyl)methyl]-4-oxo-1-thia-3a-aza-3-indancarboxamide 7-Cyclopropyl-6-[(1-naphthyl)methyl]-1-oxo-4-oxo-1-thia-3a-aza-3-indancarboxylic acid or a pharmaceutically acceptable salt of any of the foregoing compounds.

The combination described herein may comprise a compound of Formula II selected from at least one of:

(3R)-7-Cyclopropyl-6-[(1-naphthyl)methyl]-4-oxo-1-thia-3a-aza-3-indancarboxylic acid 7-Cyclopropyl-4-oxo-6-{[m-(trifluoromethyl)phenyl]methyl}-1-thia-3a-aza-3-indancarboxylic acid, (3R)-7-Cyclopropyl-4-oxo-6-{(7-thiabicyclo[4.3.0]nona-1,3,5,8-tetraen-8-yl)methyl}-1-thia-3a-aza-3-indancarboxylic or a pharmaceutically acceptable salt of any of the foregoing compounds.

In an example, the combination described herein may comprise the compound (3R)-7-Cyclopropyl-6-[(1-naphthyl)methyl]-4-oxo-1-thia-3a-aza-3-indancarboxylic acid or a pharmaceutically acceptable salt thereof. In a further example, the combination described herein may comprise the compound 7-Cyclopropyl-4-oxo-6-{[m-(trifluoromethyl)phenyl]methyl}-1-thia-3a-aza-3-indancarboxylic acid or a pharmaceutically acceptable salt thereof. In still a further example, the combination described herein may comprise the compound (3R)-7-Cyclopropyl-4-oxo-6-{(7-thiabicyclo[4.3.0]nona-1,3,5,8-tetraen-8-yl)methyl}-1-thia-3a-aza-3-indancarboxylic or a pharmaceutically acceptable salt thereof.

There is also provided a combination as described herein for use as a medicament.

Further, there is provided a combination as described herein for use in the treatment and/or prevention of tuberculosis.

There is also provided the use of a combination as described herein for the manufacture of a medicament for the treatment and/or prevention of tuberculosis.

There is also provided a method for treatment and/or prevention of tuberculosis comprising administering to a mammal, such as a human or an animal, in need thereof an effective amount of a combination as described herein. In this document, a mammal may be a human and/or an animal.

The tuberculosis described in this document may involve *Mycobacterium tuberculosis* (Mtb). Additionally or alternatively, the tuberculosis may involve one or more tuberculosis causing bacteria selected from the group consisting of *M. bovis, M. africanum, M. canetti* and/or *M. microti*. The tuberculosis may be active, latent, drug-sensitive and/or drug-resistant tuberculosis. Further, the tuberculosis may be one or more selected from the group consisting of pulmonary tuberculosis, military tuberculosis, laryngeal tuberculosis, extrapulmonary tuberculosis, tuberculosis peritonitis, tuberculosis pericarditis, osteal tuberculosis, renal tuberculosis, adrenal tuberculosis and tuberculosis meningitis.

The treatment described herein, such as a treatment using the combination of the present disclosure, may be curative treatment involving tuberculosis eradication or substantial tuberculosis eradication. In this document, the term eradication intends complete removal of tuberculosis bacteria or clinical cure where the bacteria are no longer detectable and the patient no longer has symptoms. These measures of eradication or clinical cure may be determined by sputum sampling and sputum smear and culture.

The prevention described herein, such as prevention using a compound of Formula II described herein, may involve preventing tuberculosis bacteria from multiplying and/or growing. The prevention is believed to occur by inhibiting lipid synthesis (in particular, but not limited to, in response to environmental changes) and altering the redox state of the bacteria.

As used herein, drug-resistant tuberculosis is intended to mean reduction in the effectiveness of a drug such as an antibiotic in the treatment of tuberculosis. The tuberculosis bacteria will then no longer be affected and/or killed by the drug or affected to a very limited extent. The drug-resistant tuberculosis may be at least one of the following: isoniazid resistant tuberculosis, multi-drug resistant tuberculosis, extensively resistant tuberculosis, totally resistant tuberculosis. Isoniazid resistant tuberculosis involves tuberculosis bacteria that are resistant to treatment with isoniazid. Multi-drug resistant tuberculosis involves tuberculosis bacteria that are resistant to treatment with at least two first line anti-tuberculosis drugs such as isoniazid and rifampicin. Extensively resistant tuberculosis involves tuberculosis bacteria that are resistant to at least rifampicin and isoniazid, to any member of quinolone broad-spectrum antibiotics and/or second line anti-tuberculosis drugs such as kanamycin, capreomyucin, amikacin.

While not wishing to be bound by any specific theory, it is believed that the compounds of Formula II of the present disclosure affect the tuberculosis bacteria by inhibiting lipid synthesis (in particular, but not limited to, in response to environmental changes) and altering the redox state of the bacteria. These direct effects lead to inhibition of the bacteria's ability to tolerate drugs against tuberculosis such as INH, tolerate low pH, tolerate reactive nitrogen and oxygen species, and form biofilms. The compounds of Formula II also inhibit growth in some standard media conditions, inhibit the selection for INH resistant mutants due to katG mutation and, therefore, decrease and/or inhibit the rate of INH resistance. Further, the compounds of Formula II of the present disclosure appear to sensitize resistant tuberculosis bacteria to treatment with a drug against tuberculosis as described herein, such as INH.

Thus, there is provided a compound of Formula II as described herein for use as a tuberculosis bacteria tolerance inhibitor. There is also provided the use of a compound of Formula II for the manufacture of a medicament for tuberculosis bacteria tolerance inhibition. There is also provided a method for tuberculosis bacteria tolerance inhibition comprising administering to a mammal, such as a human or an animal, an effective amount of a compound of Formula II as described herein. There is also provided a use of a compound of Formula II as described herein as a tuberculosis bacteria tolerance inhibitor. The tuberculosis may be as described herein.

Thus, there is provided a compound of Formula II as described herein for use in sensitizing tuberculosis bacteria to treatment with a drug against tuberculosis. There is also provided the use of a compound of Formula II as described herein for the manufacture of a medicament for use in sensitizing tuberculosis bacteria to treatment with a drug against tuberculosis. There is also provided a method for sensitizing tuberculosis bacteria to treatment with a drug against tuberculosis comprising administering to a mammal, such as a human or an animal, an effective amount of a compound of Formula II as described herein. There is also provided a use of a compound of Formula II as described herein to sensitize tuberculosis bacteria to treatment with a drug against tuberculosis. The tuberculosis and/or the drug against tuberculosis may be as described herein.

Thus, there is provided a compound of Formula II as described herein to improve the efficacy of a drug against tuberculosis. There is also provided the use of a compound of Formula II as described herein for the manufacture of a medicament to improve the efficacy of a drug against tuberculosis. There is also provided a method for sensitizing tuberculosis bacteria to treatment with a drug against tuberculosis comprising administering to a mammal, such as a human or an animal, an effective amount of a compound of Formula II as described herein to improve the efficacy of a drug against tuberculosis. There is also provided a use of a compound of Formula II as described herein to improve the efficacy of a drug against tuberculosis. The tuberculosis and/or the drug against tuberculosis may be as described herein.

A compound of Formula II as described herein is considered to have biofilm inhibition activity if the biofilm inhibition affects the formation of biofilm to an extent of at least 25%, such as 50%, 75% or 100% when used at a molar concentration within the range of from about 25 micromolar to about 100 micromolar such as about 25 micromolar, 50 micromolar or 100 micromolar. Additionally or alternatively, the compounds Formula II are considered to have biofilm inhibitory activity if they exhibit full biofilm inhibition as shown in Table 2 herein.

The present disclosure provides a compound of Formula II as described herein for use in the treatment and/or prevention of tuberculosis. There is also provided a use of a compound of Formula II as described herein for the manufacture of a medicament for the treatment and/or prevention of tuberculosis. Further, there is provided a method for treatment and/or prevention of tuberculosis comprising administering to a mammal, such as a human or an animal, an affective amount of a compound of Formula II as described herein.

There is also provided a compound of Formula IIIa and/or Formula IIIb as described herein for use as a medicament in therapy.

There is also provided a compound of Formula IV as described herein for use as a medicament in therapy. The compound of Formula IV may be a compound of Formula IVa, IVb, IVa1, IVa2, IVa3 or IVa4 as described herein.

The present disclosure provides a compound of Formula IIIa and/or Formula IIIb as described herein for use in the treatment and/or prevention of tuberculosis. There is also provided a use of a compound of Formula IIIa and/or Formula IIIb a as described herein for the manufacture of a medicament for the treatment and/or prevention of tuberculosis. Further, there is provided a method for treatment and/or prevention of tuberculosis comprising administering to a mammal, such as a human or an animal, an affective amount of a compound of Formula IIIa and/or Formula IIIb as described herein.

The present disclosure provides a compound of Formula IV as described herein for use in the treatment and/or prevention of tuberculosis. There is also provided a use of a compound of Formula IV as described herein for the manufacture of a medicament for the treatment and/or prevention of tuberculosis. Further, there is provided a method for treatment and/or prevention of tuberculosis comprising administering to a mammal, such as a human or an animal, an affective amount of a compound of Formula IV as described herein.

Salts

The compounds of the present disclosure may be provided as a pharmaceutically acceptable salt. A suitable pharmaceutically acceptable salt of a compound of the present disclosure may be, for example, a base-addition salt of a compound of the present disclosure which is sufficiently acidic, for example, a metal salt, for example, lithium, sodium, potassium, calcium, magnesium, zinc or aluminum, an ammonium salt, a salt with an organic base which affords a physiologically acceptable cation, which includes quartenery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (IR,2S)-2-hydroxyinden-I-amine, morpholine, N-methylpiperidine, N-ethylpiperidine, imidazole, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine. In an example, there is provided an imidazole salt of the compounds of the present disclosure.

Solvates or Hydrates

Certain compounds of the present disclosure may exist as solvates or hydrates. It is to be understood that the present disclosure encompasses all such solvates or hydrates. Compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

Co-Crystals

In a salt, proton transfer may occur between the active pharmaceutical ingredient and the counter ion of the salt. However, in some cases there is no or only partial proton transfer and the solid is therefore not a true salt. It is accepted that the proton transfer is in fact a continuum, and can change with temperature, and therefore the point at which a salt is better described as a "co-crystal" may be subjective. The term "co-crystal" as used herein refers to multicomponent system in which there exists a host molecule or molecules (active pharmaceutical ingredient) and a guest (or co-former) molecule or molecules. The guest or co-former molecule is defined as existing as a solid at room temperature in order to distinguish the co-crystal from solvates. However, a co-crystal may itself form solvates. In a co-crystal there is generally predominance for interaction through non-ionic forces, such as hydrogen bonding.

Polymorphs

Compounds of the present disclosure may exist in a continuum of solid states ranging from fully amorphous to fully crystalline. Thus, it is to be understood that all polymorphs, such as mixtures of different polymorphs, are included within the scope of the claimed compounds.

Prodrugs

In addition, compounds of the present disclosure may be administered in the form of a prodrug. A prodrug is a compound which may have little or no pharmacological activity itself, but when such compound is administered into or onto the body of a patient, it is converted into a compound of Formula II.

Methods of Preparation

Compounds of the present disclosure may be prepared as described in WO 2014/185833. The compounds may also be prepared as described for structurally related compounds. The reactions may be carried out as in standard procedures or as described in the experimental section of this document. The sulfide of the compounds of Formula II may be oxidized with the aid of meta-chloroperoxybenzoic acid (mCPBA) to sulphoxide and sulphone, respectively. Additionally or alternatively, the compounds may be prepared as depicted in Schemes 1 to 10 as depicted below.

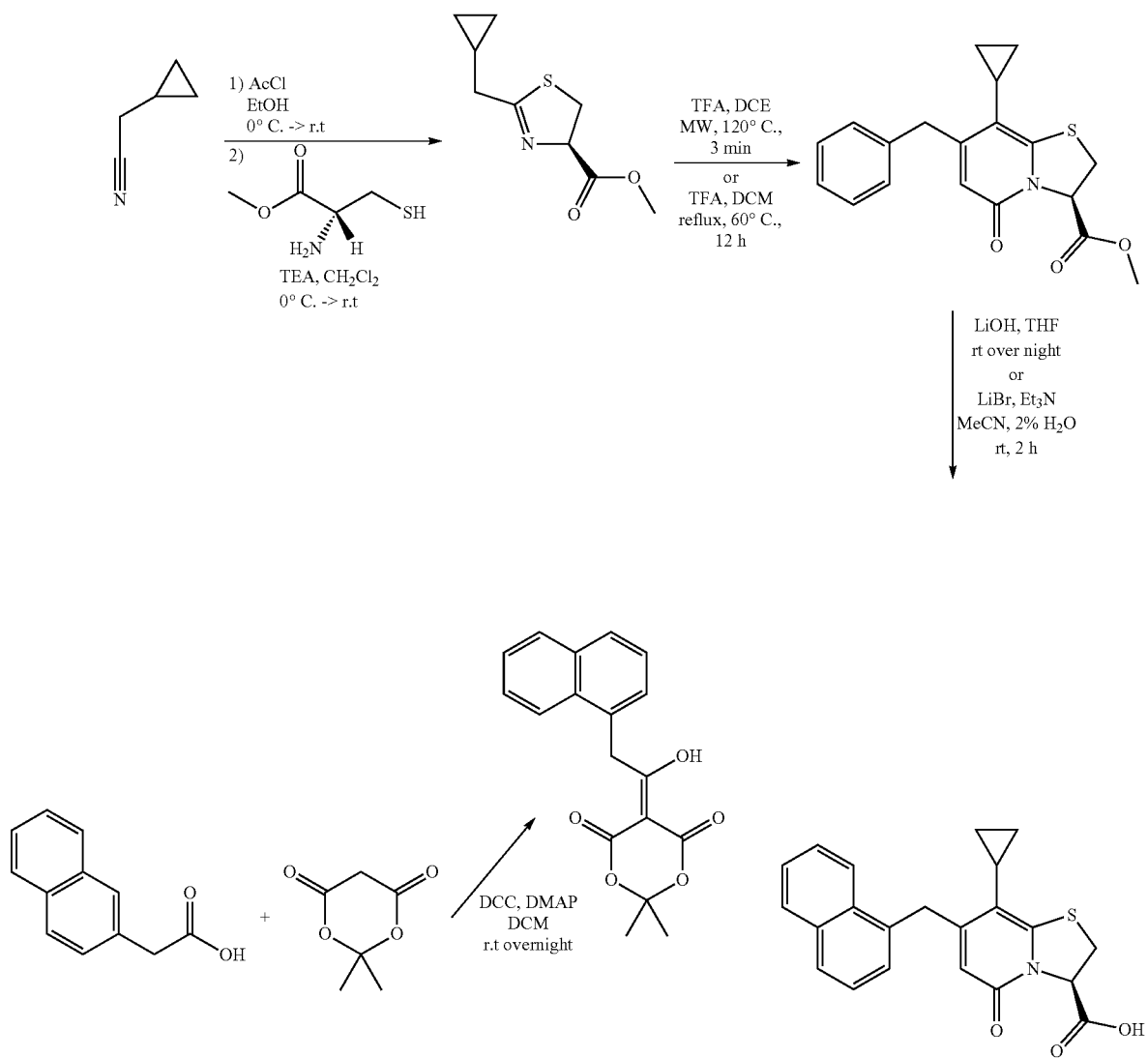

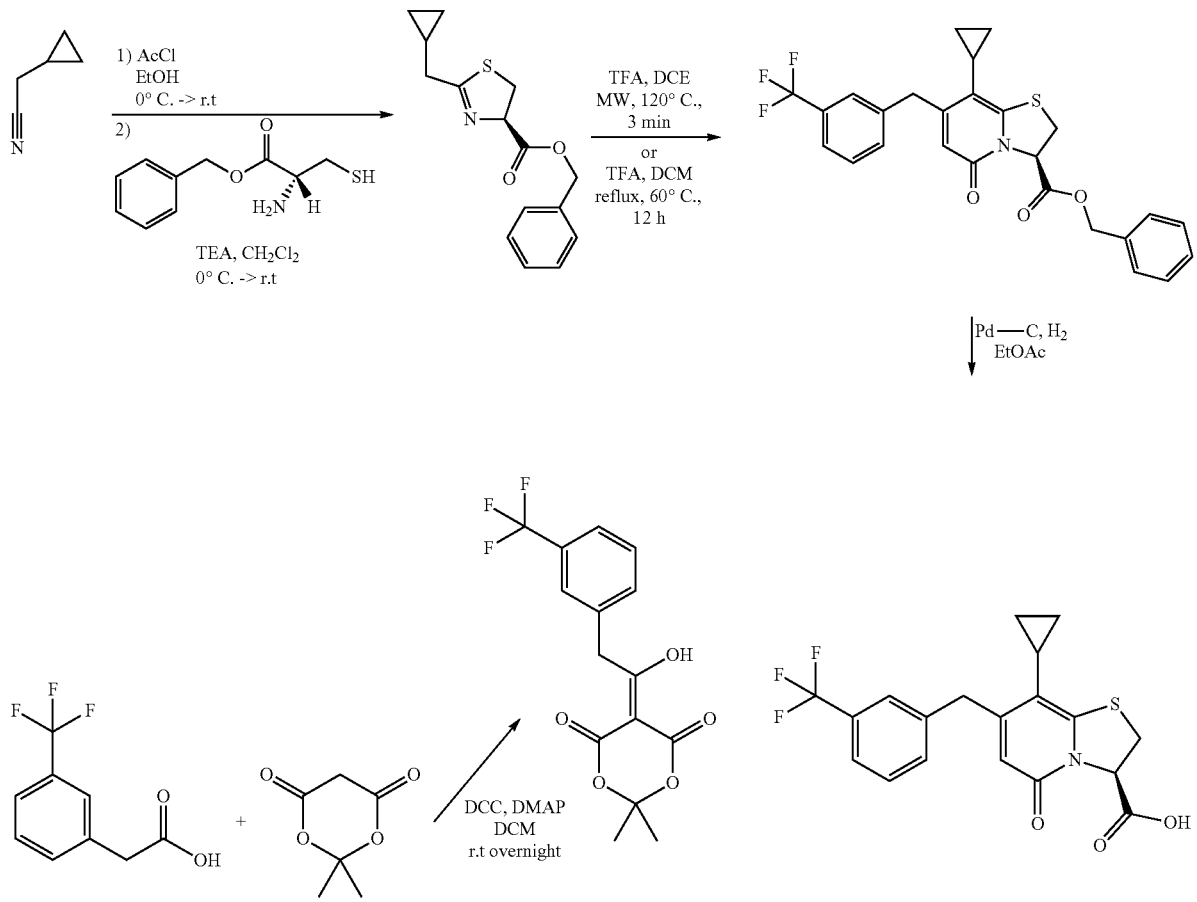
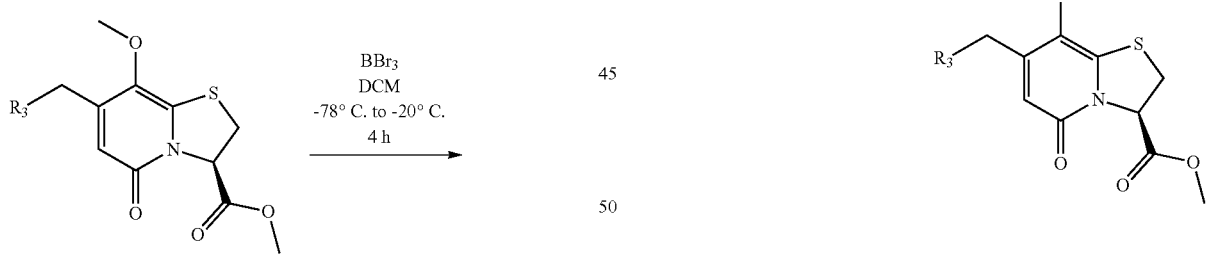
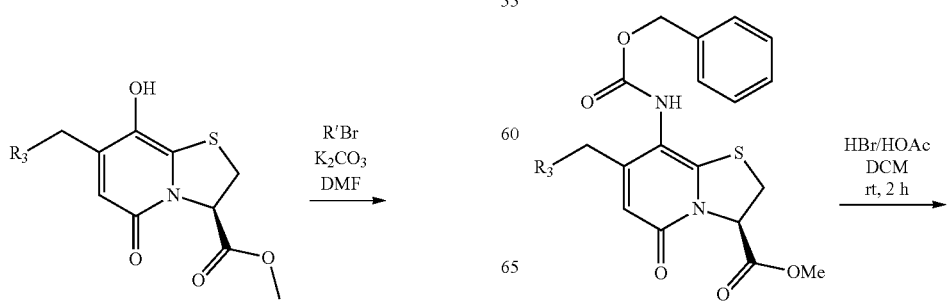

-continued
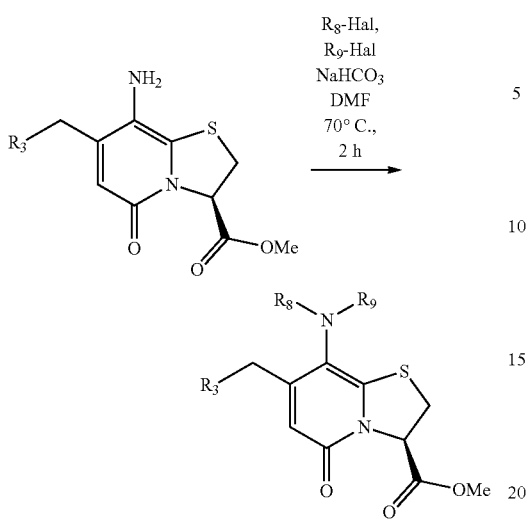
Scheme 6
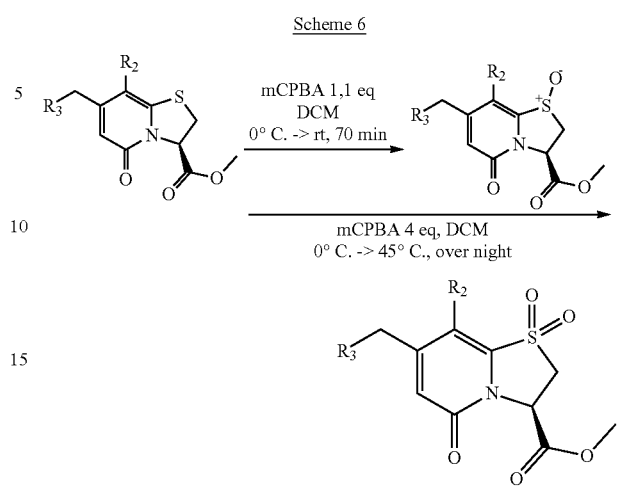
Scheme 4
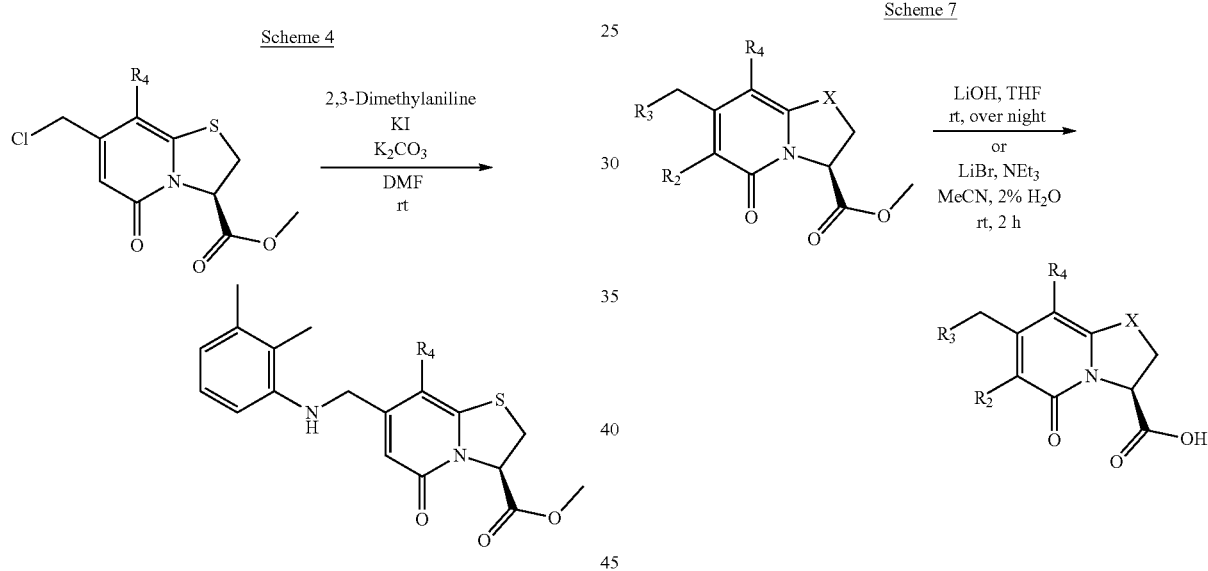
Scheme 7
Scheme 5
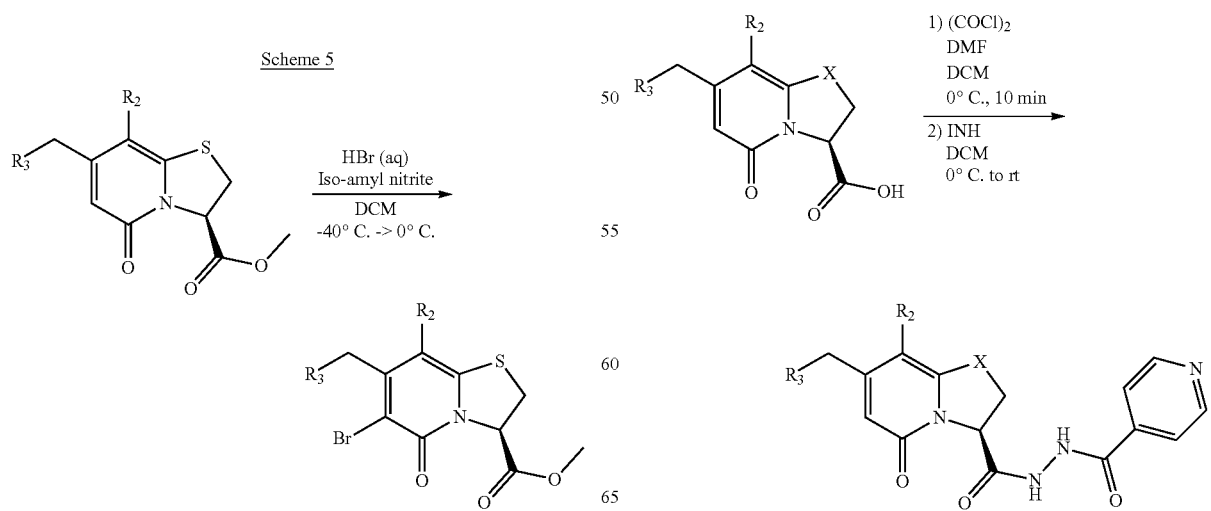
Scheme 8

Scheme 9
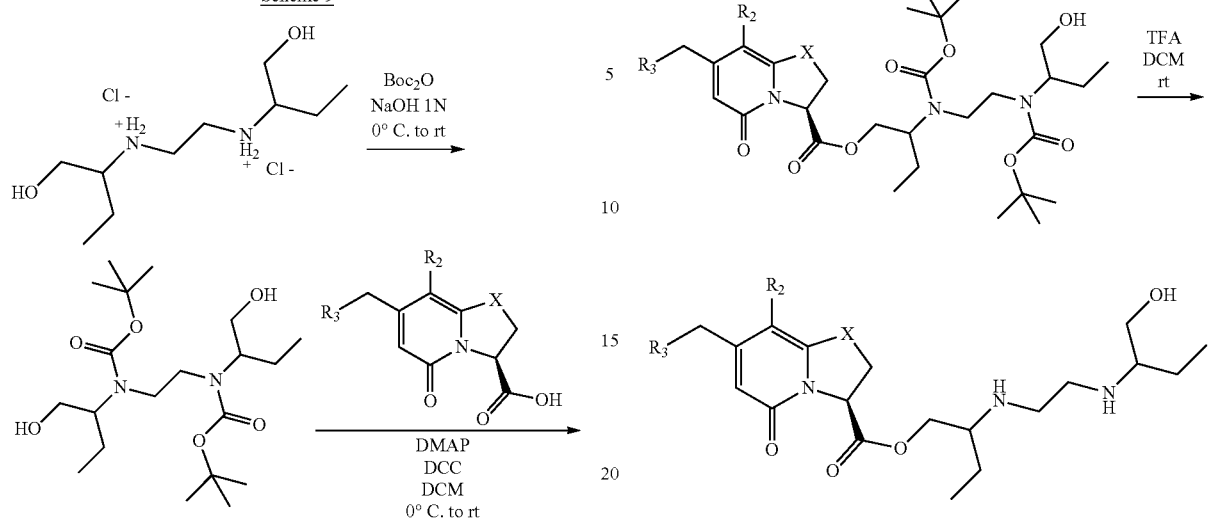
Scheme 10
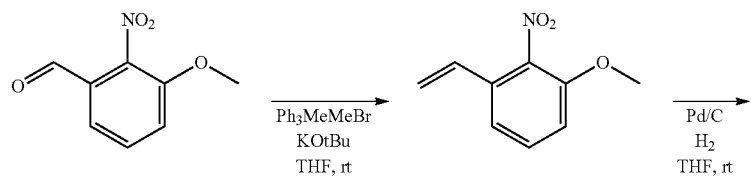
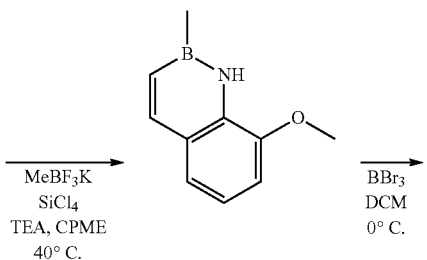
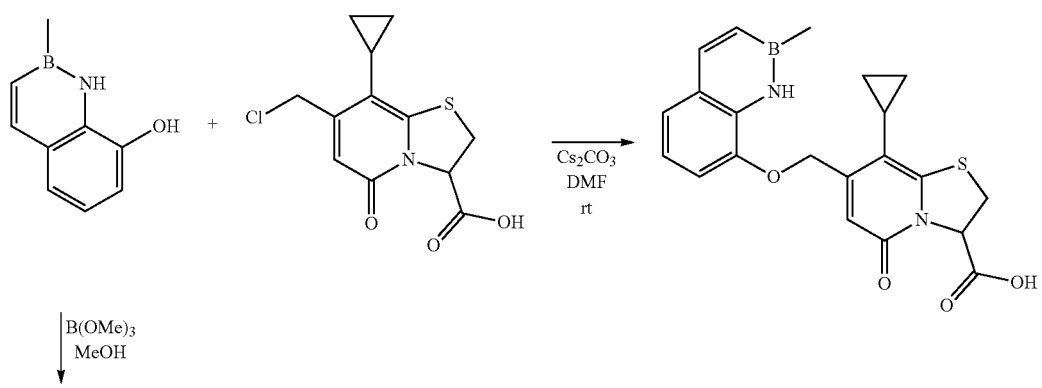

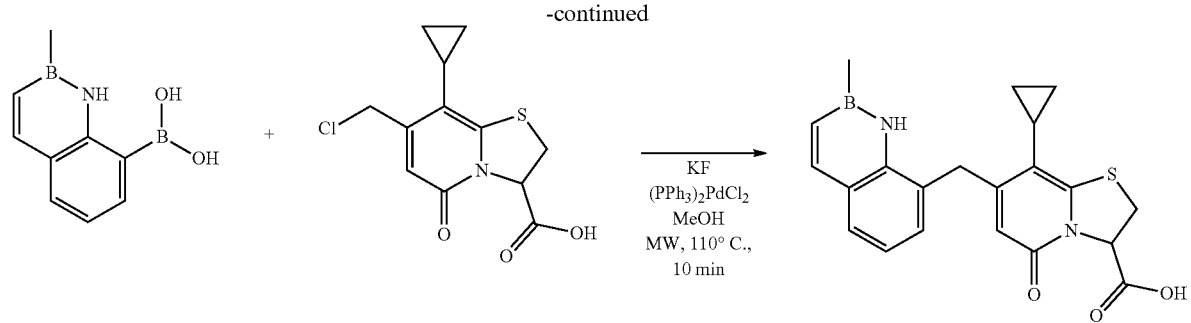
-continued
Scheme 11
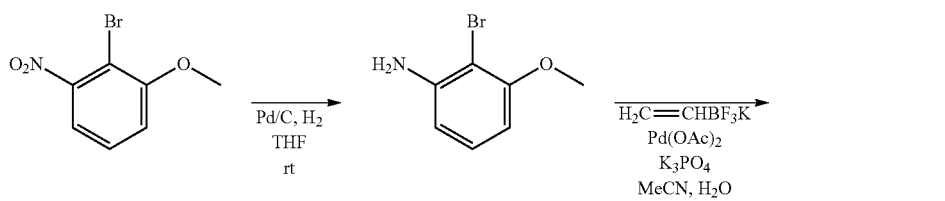
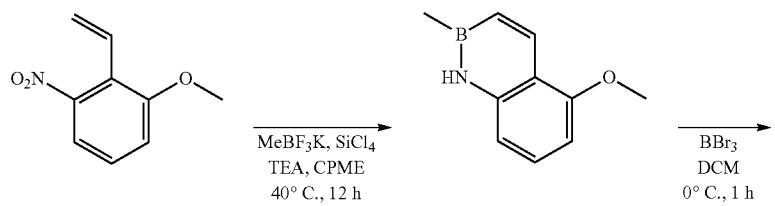
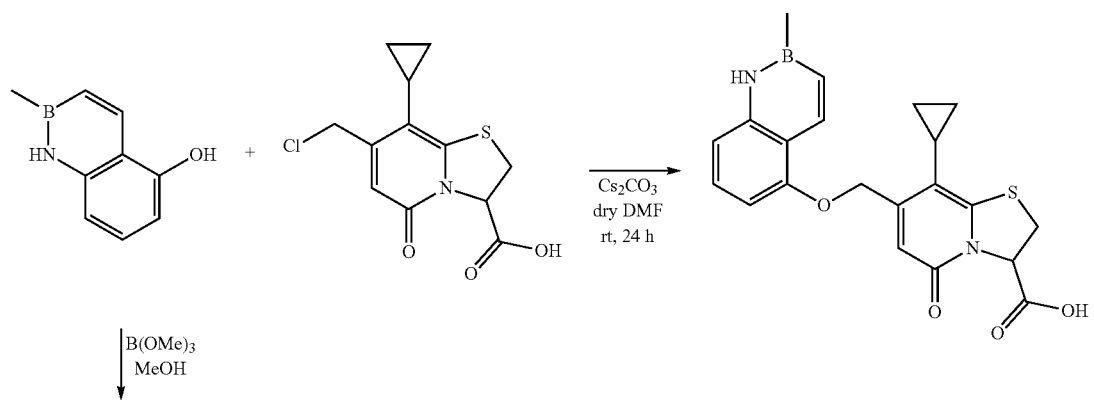
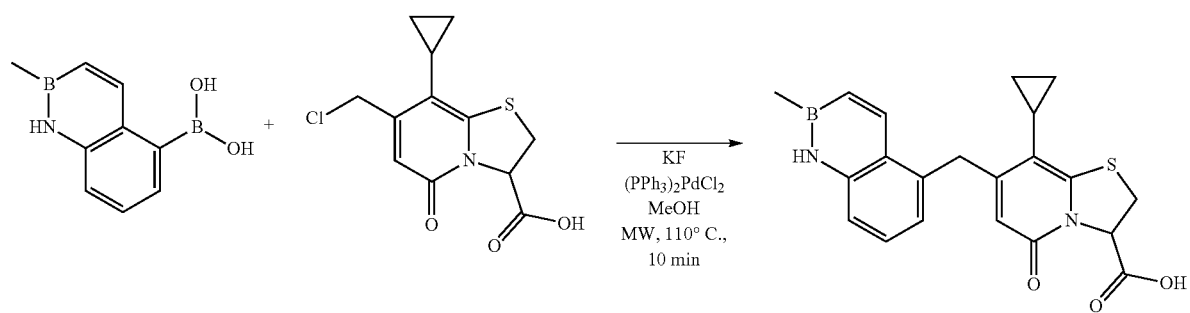

Intermediates

The present disclosure provides compounds which may be used as intermediates in the synthesis of compounds of Formula II described herein. For instance, the intermediates may be at least one of the following compound:

Benzyl (4R)-2-(cyclopropylmethyl)Δ²-1,3-thiazoline-4-carboxylate, 5-{1-Hydroxy-2-[m-(trifluoromethyl)phenyl]ethylidene}-2,2-dimethyl-1,3-dioxane-4,6-dione, Benzyl (3R)-7-cyclopropyl-4-oxo-6-{[m-(trifluoromethyl)phenyl]methyl}-1-thia-3a-aza-3-indancarboxylate, Methyl (3R)-7-cyclopropyl-4-oxo-6-{[m-(trifluoromethyl)phenyl]methyl}-1-thia-3a-aza-3-indancarboxylate. These intermediates may be used in the synthesis of compounds of Formula II wherein $R_3$ is meta-trifluoromethyl, i.e. compounds having the following chemical structure:

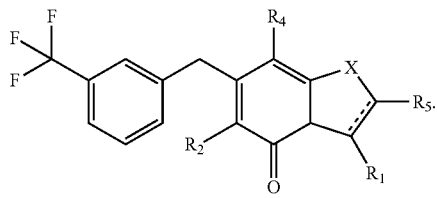

Derivatives of 4-Aminosalicylic Acid 4-aminosalicylic acid, commonly known as PAS, is an antibiotic used to treat tuberculosis. The present disclosure provides a combination comprising:

(i) 4-aminosalicylic acid, i.e.

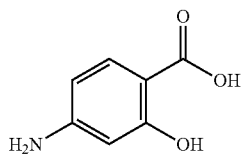 [SMILES: Nc1ccc(C(=O)O)c(O)c1]

or a pharmaceutically acceptable salt thereof, and (ii) a compound of Formula II as described herein, wherein $R_1$, $R_2$, $R_3$, $R_4$, $R_5$ and X may have values as described in this document, or a pharmaceutically acceptable salt thereof.

4-aminosalicylic acid may form a covalent bond with the $R_1$ group of the compounds of Formula II disclosed herein resulting in a compound of Formula V:

Formula V

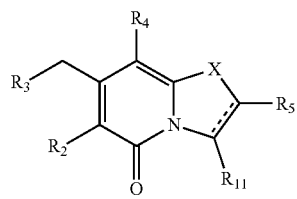

wherein
$R_{11}$ is selected from:

a)

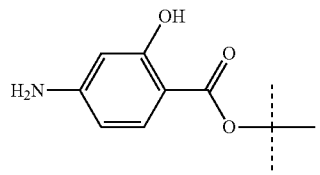

b)

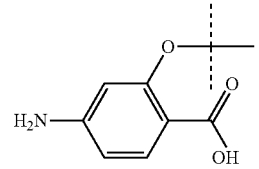

c)

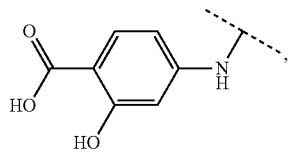

and
$R_2$, $R_3$, $R_4$, $R_5$ and X may have values as described in this document,
or a pharmaceutically acceptable salt thereof.

The compound of Formula V may exist as a compound of Formula Va and Formula Vb, respectively:

Formula Va

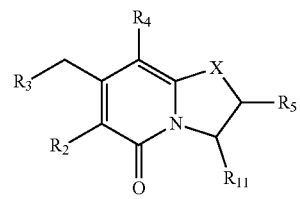

Formula Vb

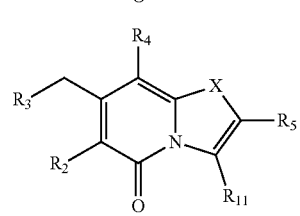

wherein $R_2$, $R_3$, $R_4$, $R_5$, $R_{11}$ and X may have values as described in this document, or a pharmaceutically acceptable salt thereof.

The compound of Formula Va may exist as cis and trans stereoisomers. The present disclosure encompasses all these compounds which are denominated compounds of Formula Va1, Va2, Va3 and Va4, the chemical structures of which are shown in FIG. 8.

Further, there is provided a compound of Formula V as described herein for use as a medicament in therapy.

There is also provided a compound of Formula V as described herein for use in the treatment and/or prevention of tuberculosis. There is also provided the use of a compound of Formula V as described herein for the manufacture of a medicament for the treatment and/or prevention of tuberculosis. There is also provided a method for the treatment and/or prevention of tuberculosis comprising administering to a mammal, such as a human or an animal, an effective amount of a compound of Formula V as described herein. The tuberculosis may be as described in this document.

REFERENCES

1. Org. Biomol. Chem., 2005, 3, 3886-3892, Aberg, Veronica et al.
2. Bioorganic & Medicinal Chemistry Letters (2008), 18(12), 3536-3540, Aberg, Veronica et al.
3. Journal of Medicinal Chemistry (2010), 53(15), 5690-5695, Chorell, Erik et al
4. Tetrahedron Letters (2007), 48(26), 4543-4546, Pemberton, Nils et al
5. Bioorganic & Medicinal Chemistry (2012), 20(9), 3128-3142, Chorell, Erik et al.
6. Organic & Biomolecular Chemistry (2005), 3(15), 2817-2823, Aaberg, Veronica et al
7. WO2014/185853 A1.
8. Journal of Organic Chemistry (2007), 72(13), 4917-4924, Chorell, Erik et al.
9. Comb. Chem. 2002, 4, 630-639, Emtenas, Hans et al.
10. J. Med. Chem. 2016, 59, 2094-2108, James A. D. Good et al.
11. Cell Chemical Biology 23, 404-414, James A. D. Good et al.
12. PCT/EP2015/076578

The disclosure is further illustrated by the following non-limitative Examples

EXAMPLES

In this document, unless otherwise stated, the naming and the drawing of the chemical compounds and radicals have been made using the program Chem Doodle version 7.0.1 or version 7.0.2. If the name and drawing are inconsistent, the chemical structure shall be considered to be correct.

Abbreviations

ANOVA Analysis of variance
aq aqueous
BOC tert-butyloxycarbonyl
BSA Bovine Serum Albumine
CFU Colony Forming Unit
CPME Cyclopentyl methyl ether
DCC Dicyclohexyl carbodiimide
DMAP Dimethyl aminopyridine
DMF Dimethyl formamide
DCM Dichloromethane
EMB Ethambutol
FAB Fast Atom Bombardment
HRMS High Resolution Mass Spectrosopy
INH Isoniazide or isonicotinylhydrazide
IUPAC International Union of Pure and Applied Chemistry
OADC Middlebrook Oleic Albumin Dextrose Catalase Growth Supplement
KatG catalase-peroxidase
MeCN Acetonitrile
MIC minimum inhibitory concentration
MicroM micromolar
µM micromolar
Mtb *Mycobacterium tuberculosis*
MW Microwave heating
MS Mass Spectroscopy
NMR Nuclear Magnetic Resonance
ND none detected
nm nanometer
OD optical density
λ wavelength
ODo optical density at 600 nm
PBS Phosphate-Buffered Saline buffer
PZA Pyrazinamide
RIF Rifampicin or Rifampin
RT room temperature
rt room temperature
sat saturated
TB tuberculosis
TEA Triethylamine
TFA Trifluoroacetic acid
THF Tetrahydrofuran
TWEEN 80 Polyoxyethylenesorbitan monooleate
WT Wild Type Chemistry General $^1$H NMR spectra were recorded on a 400 or 600 MHz spectrometer at 298 K and calibrated by using the residual peak of the solvent as the internal standard (CDCl$_3$: $\delta_H$7.26 ppm; $\delta_C$=77.16 ppm; DMSO-d$_6$: $\delta_H$=2.50 ppm; $\delta_C$=39.52 ppm). The purity of all final compounds was ≥95% by LC-MS.

Examples 1-54

The compounds of Examples 1-54 were prepared in accordance with or in analogy with references 1-11 as described herein or as described in this document. $^1$H NMR data are provided for new compounds 36-50. Additionally, NMR data are provided for examples 1, 15 and 27. Table 1 shows data for Examples 1-54.

By way of example, the compound of Example 1 was prepared as follows.

Example 1

(3R)-7-Cyclopropyl-6-[(1-naphthyl)methyl]-4-oxo-1-thia-3a-aza-3-indancarboxylic acid Cyclopropylacetonitrile was reacted with ethanol and acetyl chloride to generate 2-cyclopropyl-1-ethoxy-1-ethanimine that was reacted with (R)-cysteine methyl ester hydrochloride and Et$_3$N in CH$_2$Cl$_2$ without any workup to form Methyl 2-(cyclopropylmethyl)Δ$^2$-1,3-thiazoline-4-carboxylate. (1-Naphthyl)acetic acid activated with DCC and DMAP was reacted with 2,2-Dimethyl-1,3-dioxane-4,6-dione in DCM to give 5-[1-Hydroxy-2-(1-naphthyl)ethylidene]-2,2-dimethyl-1,3-dioxane-4,6-dione. These two building blocks were allowed to react with TFA at elevated temperature to give Benzyl (3R)-7-cyclopropyl-4-oxo-6-{[m-(trifluoromethyl)phenyl]methyl}-1-thia-3a-aza-3-indancarboxylate. Hydrolysis with LiOH in THF or LiBr and Et3N in wet (2%) acetonitrile gave (3R)-7-Cyclopropyl-6-[(1-naphthyl)methyl]-4-oxo-1-thia-3a-aza-3-indancarboxylic acid (Scheme 1). NMR and MS data are provided in Table 1.

TABLE 1

| Example Number | Chemical Structure<br>¹H-NMR and and HRMS data | IUPAC name |
|---|---|---|
| 1 | 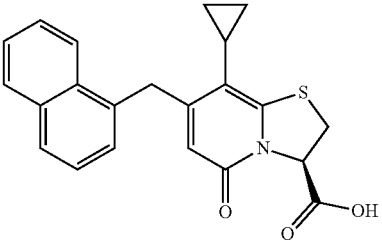 [SMILES: O=C(O)[C@@H]1CSc2c(C3CC3)c(Cc3cccc4ccccc34)cc(=O)n21] | (3R)-7-Cyclopropyl-6-[(1-naphthyl)methyl]-4-oxo-1-thia-3a-aza-3-indancarboxylic acid |
| | ¹H NMR: δ 7.93-7.99 (m, 1H), 7.83-7.92 (m, 2H), 7.46-7.56 (m, 3H), 7.36 (d, J 6.95 Hz, 1H), 5.16 (s, 1H), 4.92-4.97 (m, 1H), 4.45 (d, J 17.29 Hz, 1H), 4.34 (d, J 17.29 Hz, 1H), 3.47-3.56 (m, 2H), 1.62-1.69 (m, 1H), 0.78-0.96 (m, 2H), 0.56-0.73 (m, 2H). HRMS (FAB+) calcd for (M + 1) $C_{22}H_{20}NO_3S$: 378.1164. Observed: 378.1163. | |
| 2 | 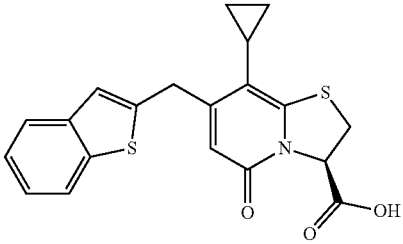 [SMILES: O=C(O)[C@@H]1CSc2c(C3CC3)c(Cc3cc4ccccc4s3)cc(=O)n21] | (3R)-7-Cyclopropyl-4-oxo-6-{(7-thiabicyclo-[4.3.0]nona-1,3,5,8-tetraen-8-yl)methyl}-1-thia-3a-aza-3-indancarboxylic acid |
| | ¹H NMR (400 MHz, DMSO-d6): δ = d 0.53-0.73 (m, 2H), 0.81-0.97 (m, 2H), 1.56-1.67 (m, 1H), 3.50 (dd J1 = 1.81 Hz, J2 = 11.93 Hz, 1H), 3.78 (dd J = 9.12 Hz, J2 = 11.91 Hz, 1H), 4.15- 4.30 (m, 2H), 5.37 (dd J1 = 1.78 Hz, J2 = 9.10 Hz, 1H), 5.61 (s, 1H), 7.35-7.43 (m, 2H), 7.47 (s, 1H), 7.71-7.77 (m, 1H), 7.97-8.04 (m, 1H). HRMS (electrospray ionization) calcd for [M + Li] $C_{20}H_{16}NO_3S_2$ 382.0572. Observed 382.0578 | |
| 3 | 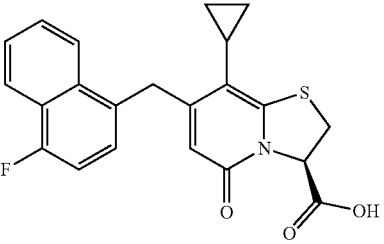 [SMILES: O=C(O)[C@@H]1CSc2c(C3CC3)c(Cc3ccc(F)c4ccccc34)cc(=O)n21] | (3R)-7-Cyclopropyl-6-[(4-fluoro-1-naphthyl)methyl]-4-oxo-1-thia-3a-aza-3-indan-carboxylic acid |
| 4 | 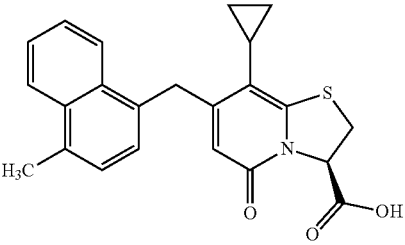 [SMILES: Cc1ccc(Cc2cc(=O)n3c(c2C2CC2)SC[C@H]3C(=O)O)c2ccccc12] | (3R)-7-Cyclopropyl-6-[(4-methyl-1-naphthyl)methyl]-4-oxo-1-thia-3a-aza-3-indancarboxylic acid |
| 5 | 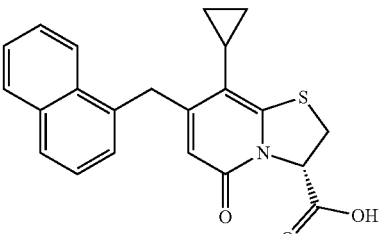 | (3S)-7-Cyclopropyl-6-[(1-naphthyl)-methyl]-4-oxo-1-thia-3a-aza-3-indan-carboxylic acid |

TABLE 1-continued

| Example Number | Chemical Structure ¹H-NMR and and HRMS data | IUPAC name |
|---|---|---|
| 6 | | 5-Cyclopropyl-4-[(1-naphthyl)-methyl]-2-oxo-8-(3-thienyl)-7-thia-1-azabicyclo[4.3.0]-nona-3,5,8-triene-9-carboxylic acid |
| 7 | | (3R)-7-Cyclopropyl-6-[(1-naphthyloxy)-methyl]-4-oxo-1-thia-3a-aza-3-indan-carboxylic acid |
| 8 | | (3R)-7-Cyclopropyl-6-[(2-fluoro-5-methylphenyl)-methyl]-4-oxo-1-thia-3a-aza-3-indan-carboxylic acid |
| 9 | | (3R)-7-Cyclopropyl-4-oxo-6-[(2,3-xylyl)-methyl]-1-thia-3a-aza-3-indan-carboxylic acid |
| 10 | | (3R)-7-Methyl-6-[(1-naphthyl)methyl]-4-oxo-1-thia-3a-aza-3-indancarboxylic acid |
| 11 | | (N-Methylmethoxy-amino){(3R)-7-cyclopropyl-6-[(1-naphthyl)methyl]-4-oxo-1-thia-3a-aza-3-indanyl}formaldehyde |

TABLE 1-continued

| Example Number | Chemical Structure <br> ¹H-NMR and and HRMS data | IUPAC name |
|---|---|---|
| 12 | | (3R)-7-Cyclopropyl-6-[(1-naphthyl)methyl]-3-(1H-1,2,3,4-tetrazol-5-yl)-1-thia-3a-aza-4-indanone |
| 13 | | 5-Cyclopropyl-4-[(1-naphthyl)methyl]-2-oxo-8-phenyl-7-thia-1-azabicyclo[4.3.0]-nona-3,5,8-triene-9-carboxylic acid |
| 14 | | 5-Cyclopropyl-4-[(1-naphthyl)methyl]-2-oxo-8-(m-tolyl)-7-thia-1-azabicyclo[4.3.0]-nona-3,5,8-triene-9-carboxylic acid |
| 15 | | (3R)-7-Cyclopropyl-6-[(2-naphthyl)methyl]-4-oxo-1-thia-3a-aza-3-indancarboxylic acid |

¹H NMR (DMSO, 400 MHz) d = 8.13-8.10 (m, 1H), 7.95-7.92 (m, 1H), 7.67-7.64 (m, 2H), 7.54 (s, 1H), 7.37-7.31 (m, 2H), 5.25 (d, 1H, J = 8.8 Hz), 5.23 (s, 1H), 4.46 (d, 1H, J = 17.6 Hz), 4.37 (d, 1H, J = 17.6 Hz), 3.72 (dd, 1H, J = 9.2, 11.6 Hz), 3.51 (d, 1H, J = 11.6 Hz), 1.74-1.67 (m, 1H), 0.93-0.86 (m, 2H), 0.66-0.60 (m, 2H) ppm.

| 16 | | (3R)-7-Cyclopropyl-3-(hydroxymethyl)-6-[(1-naphthyl)methyl]-1-thia-3a-aza-4-indanone |

TABLE 1-continued

| Example Number | Chemical Structure <br> ¹H-NMR and and HRMS data | IUPAC name |
| --- | --- | --- |
| 17 | | (3R)-6-[(1-Naphthyl)-methyl]-4-oxo-7-(2-thienyl)-1-thia-3a-aza-3-indancarboxylic acid |
| 18 | | 5-Cyclopropyl-4-[(1-naphthyl)methyl]-2-oxo-8-(1H-1,2,3-triazol-4-yl)-7-thia-1-azabicyclo[4.3.0]-nona-3,5,8-triene-9-carboxylic acid |
| 19 | | 8-Benzyl-5-cyclopropyl-4-[(1-naphthyl)methyl]-2-oxo-7-thia-1-azabicyclo-[4.3.0]-nona-3,5,8-triene-9-carboxylic acid |
| 20 | | (3R)-7-Cyclopropyl-6-[(2,3-dichlorophenyl)-methyl]-4-oxo-1-thia-3a-aza-3-indan-carboxylic acid |
| 21 | | (3R)-7-Cyclopropyl-6-[(1-naphthyl)methyl]-4-oxo-1-thia-3a-aza-3-indancarboxamide |
| 22 | | {(3R)-7-Cyclopropyl-6-[(1-naphthyl)-methyl]-4-oxo-1-thia-3a-aza-3-indanyl}-(phenylsulfonylamino)-formaldehyde |

TABLE 1-continued

| Example Number | Chemical Structure <br> ¹H-NMR and and HRMS data | IUPAC name |
|---|---|---|
| 23 | | (3R)-7-Isopropyl-6-[(1-naphthyl)methyl]-4-oxo-1-thia-3a-aza-3-indancarboxylic acid |
| 24 | | (3R)-7-Cyclopropyl-6-methyl-4-oxo-1-thia-3a-aza-3-indancarboxylic acid |
| 25 | | (3R)-6-[(p-Chlorophenyl)methyl]-7-cyclopropyl-4-oxo-1-thia-3a-aza-3-indancarboxylic acid |
| 26 | | {(3R)-7-Cyclopropyl-6-[(1-naphthyl)methyl]-4-oxo-1-thia-3a-aza-3-indanyl}-(methylsulfonylamino)formaldehyde |
| 27 | | (3R)-7-Cyclopropyl-4-oxo-6-[(m-tolyl)methyl]-1-thia-3a-aza-3-indancarboxylic acid |

¹H NMR (400 MHz, DMSO-d6): δ = 7.23-7.19 (m, 1H), 7.06-7.00 (m, 3H), 5.73 (s, 1H), 5.36 (dd, 1H, J = 1.6, 9.2 Hz), 3.93 (ABq, 2H, J = 18.2 Hz), 3.77 (dd, 1H, J = 9.2 Hz, 12 Hz), 3.50 (dd, 1H, J = 1.6 Hz, 11.6 Hz), 2.28 (s, 3H), 1.46-1.39 (m, 1H), 0.95-0.82 (m, 2H), 0.65-0.60 (m, 1H), 0.59-0.49 (m, 1H) ppm.

| 28 | | (3R)-7-Isopropyl-4-oxo-6-[2-(m-tolyl)-ethyl]-1-thia-3a-aza-3-indancarboxylic acid |

TABLE 1-continued

| Example Number | Chemical Structure <br> ¹H-NMR and and HRMS data | IUPAC name |
|---|---|---|
| 29 | | 7-(1-Methyl-1H-indol-3-yl)-6-[(1-naphthyloxy)methyl]-4-oxo-1-thia-3a-aza-3-indancarboxylic acid |
| 30 | | (3R)-6-[(4-Bromo-1-naphthyl)methyl]-7-cyclopropyl-4-oxo-1-thia-3a-aza-3-indancarboxylic acid |
| 31 | | 7-Cyclopropyl-6-[(1-naphthyl)methyl]-1-thia-3a-aza-4-indanone |
| 32 | | (3R)-7-Cyclopropyl-5-(hydroxymethyl)-6-[(1-naphthyl)methyl]-4-oxo-1-thia-3a-aza-3-indancarboxylic acid |
| 33 | | (3S)-3-Amino-7-cyclopropyl-6-[(1-naphthyl)methyl]-1-thia-3a-aza-4-indanone |
| 34 | | (2R,3R)-7-Cyclopropyl-6-[(1-naphthyl)methyl]-4-oxo-2-phenyl-1-thia-3a-aza-3-indancarboxylic acid |

TABLE 1-continued

| Example Number | Chemical Structure ¹H-NMR and and HRMS data | IUPAC name |
|---|---|---|
| 35 | | (2S,3R)-7-Cyclopropyl-2-methoxy-6-[(1-naphthyl)methyl]-4-oxo-1-thia-3a-aza-3-indancarboxylic acid |
| 36 | | 7-Cyclopropyl-4-oxo-6-{[m-(trifluoromethyl)phenyl]methyl}-1-thia-3a-aza-3-indancarboxylic acid |

¹H NMR (400 MHz, DMSO-d6): δ = 13.37(br s, 1H), 7.65-7.52 (m, 4H), 5.71 (s, 1H), 5.39 (dd, J = 1.8, 9.1 Hz, 1H), 4.16-4.04 (m, 2H), 3.78 (dd, J = 9.2 11.9 Hz, 1H), 3.50 (dd, J = 1.8, 11.9 Hz, 1H), 1.45-1.36 (m, 1H), 0.95-0.83 (m, 2H), 0.68-0.59 (m, 1H), 0.57-0.48 (m, 1H) ppm. HRMS (ESI+) (m/z): [M + H]⁺ calcd. for C19H17F3NO3S, 396.0876; found, 396.0869

| 37 | | 2-{2-[1-(Hydroxymethyl)propylamino]ethylamino}butyl 7-cyclopropyl-6-[(1-naphthyl)methyl]-4-oxo-1-thia-3a-aza-3-indancarboxylate |

¹H NMR (400 MHz, DMSO-d6): δ = 7.78 (d, J = 8.0 Hz, 1H), 7.74-7.64 (m, 2H), 7.60-7.53 (m, 1H), 7.41-7.33 (m, 2H), 7.24-7.18 (m, 1H), 6.09 (s, 1H), 5.52 (d, J = 8.4 Hz, 1H), 4.35-4.11 (m, 4H), 3.62 (d, J = 11.2 Hz, 1H), 3.48 (dd, J = 8.4 Hz, 1H), 3.39-3.13 (m, 3H), 2.95-2.70 (m, 5H), 1.66-1.50 (m, 4H), 1.37-1.06 (m, 7H), 0.77-0.56 (m, 4H) ppm.

| 38 | | {7-Cyclopropyl-6-[(1-naphthyl)methyl]-4-oxo-1-thia-3a-aza-3-indanyl}(2-isonicotinoylhydrazino)formaldehyde |

¹H NMR (400 MHz, CDCl3): δ = 8.48 (br s, 2H), 7.87-7.85 (m, 1H), 7.81-7.71 (m, 4H), 7.66-7.59 (m, 2H), 7.45-7.38 (m, 4H), 6.14 (s, 1H), 5.60 (d, J = 8.8 Hz, 1H), 4.13 (dd, J = 15.6, 49.2 Hz, 2H), 3.69 (d, J = 11.6 Hz, 1H), 3.55 (dd, J = 8.8, 11.6 Hz, 1H), 1.44-1.35 (m, 1H), 0.94-0.85 (m, 2H), 0.70-0.63 (m, 2H) ppm.

| 39 | | 7-Cyclopropyl-6-[(4-methoxy-1-naphthyl)methyl]-4-oxo-1-thia-3a-aza-3-indancarboxylic acid |

TABLE 1-continued

| Example Number | Chemical Structure<br>¹H-NMR and and HRMS data | IUPAC name |
| --- | --- | --- |

¹H NMR (400 MHz, DMSO-d6): δ = 13.35 (bs, 1H), 8.21 (d, 1H, J = 2 Hz), 7.79 (d, 1H, J = 1.2 Hz), 7.56-7.49 (m, 2H), 7.30 (d, 1H, J = 8.0 Hz), 6.97 (d, 1H, J = 8.0 Hz), 5.32 (dd, 1H, J = 1.6, 9.2 Hz), 5.23 (s, 1H), 4.34.39 (d, 1H, J = 17.2 Hz), 4.30 (d, 1H, J = 17.6 Hz), 3.98 (s, 3H), 3.79 (dd, 1H, J = 2.8, 9.0 Hz), 3.50 (dd, 1H), J = 1.6, 12 Hz), 1.76-1.70 (m, 1H), 0.98-0.86 (m, 2), 0.78-0.74 (m, 1H), 0.66-0.60 (m, 1H) ppm. HRMS (ESI+) (m/z): [M + Na]+ calcd. for C23H21NNaO4S, 430.1089; found, 430.1071

40 — (3R)-7-(Dimethyl-amino)-6-[(1-naphthyl)methyl]-4-oxo-1-thia-3a-aza-3-indancarboxylic acid ¹H NMR (400 MHz, Methanol-d4) δ 7.96-7.87 (m, 2H), 7.84 (d, J = 8.2 Hz, 1H), 7.57-7.46 (m, 3H), 7.40 (d, J = 6.9 Hz, 1H), 5.69 (s, 1H), 5.60 (d, J = 8.7 Hz, 1H), 4.45 (s, 2H), 3.92 (dd, J = 12.0, 8.8 Hz, 1H), 3.69 (d, J = 12.0 Hz, 1H), 2.70 (s, 6H).

41 — (3R)-5-Bromo-7-cyclopropyl-6-[(1-naphthyl)methyl]-4-oxo-1-thia-3a-aza-3-indancarboxylic acid ¹H NMR (400 MHz, DMSO-d6) δ = 13.65 (br s, 1H), 8.28 (d, J = 8.4 Hz, 1H), 7.99-7.95 (m, 1H), 7.81 (d, J = 8.2 Hz, 1H), 7.68-7.56 (m, 2H), 7.39 (t, J = 7.6 Hz, 1H), 6.77 (d, J = 7.1 Hz, 1H), 5.58 (dd, J = 1.4, 9.2 Hz, 1H), 4.74 (dd, J = 16.1, 51.0 Hz, 2H), 3.89 (dd, J = 9.2, 12.0 Hz, 1H), 3.59 (dd, J = 1.7, 12.0 Hz, 1H), 1.46-1.37 (m, 1H), 0.69-0.58 (m, 2H), 0.53-0.38 (m, 2H) ppm.

42 — 7-Cyclopropyl-6-[(1-naphthyl)methyl]-1,1-dioxo-4-oxo-1-thia-3a-aza-3-indan-carboxylic acid ¹H NMR (400 MHz, CDCl3): δ = 13.82 (br s, 1H), 8.00-7.97 (m, 1H), 7.93-7.89 (m, 2H), 7.57-7.51 (m, 3H), 7.41 (d, J = 6.4 Hz, 1H), 5.73 (s, 1H), 5.33 (dd, J = 1.6, 8.8 Hz, 1H), 4.59 (ABq, 2H, J = 35 Hz), 4.16-4.04 (m, 2H), 1.89-1.82 (m, 1H), 1.24-1.19 (m, 1H), 1.04-0.94 (m, 2H), 0.82-0.73 (m, 1H) ppm. HRMS calc: [M + H+]: 410.1056; found: 410.1079

43 — (3R)-7-Cyclopropyl-4-oxo-6-[(2,3-xylidino)methyl]-1-thia-3a-aza-3-indancarboxylic acid TABLE 1-continued

| Example Number | Chemical Structure<br>¹H-NMR and and HRMS data | IUPAC name |
|---|---|---|

¹H NMR (600 MHz, MeOH-d4): δ = 6.82 (t, 1H, J = 7.8 Hz), 6.47 (d, 1H, J = 7.2 Hz), 6.23 (s, 1H), 6.7 (d, 1H, J = 8.4 Hz), 5.54 (d, 1H, J = 7.8), 4.48 (ABq, 2H, J = 13.1 Hz), 3.81 (dd, 1H, J = 9, 12 Hz), 3.59 (dd, 1H, J = 1.2, 12 Hz), 2.24 (s, 3H), 2.13 (s, 3H), 1.75-1.71 (m, 1H), 1.04-1.00 (m, 1H), 0.97-0.93 (m, 1H), 0.73-0.68 (m, 2H) ppm. HRMS calc. M + H+: 371.1424; found; 317.1390

44 — 7-Cyclopropyl-6-[(1-naphthyl)methyl]-1-oxo-4-oxo-1-thia-3a-aza-3-indancarboxylic acid ¹H NMR (400 MHz, MeOH-d4): δ = 7.93-7.83 (m, 3H), 7.52-7.46 (m, 3H), 7.39 (d, 1H, J = 6.4 Hz), 5.95 (s, 1H), 5.49 (bs, 1H), 4.69 (d, 1H, J = 18 Hz), 4.60 (d, 1H, J = 18 Hz), 3.91 (dd, 1H, J = 5.2, 13.6 Hz), 3.79 (dd, 1H, J = 7.6, 13.6Hz), 2.03-1.96 (m, 1H), 1.22-1.17 (m, 2H), 1.12-1.08 (m, 1H), 0.96-0.95 (m, 1H) ppm. MS calc: [M + H+]: 394.1, found: 394.2

45 — (3R)-7-Ethoxy-6-[(1-naphthyl)methyl]-4-oxo-1-thia-3a-aza-3-indancarboxylic acid ¹H NMR, 400 MHz, (DMSO) δ 1.27 (t, J = 7.0 Hz, 3H), 3.58 (dd, J = 1.8, 11.9 Hz, 1H), 3.82-4.0 (m, 3H), 4.29 (dd, J = 16.8, 25.7 Hz, 2H), 5.34 (dd, J = 1.7, 8.9 Hz, 1H), 5.36 (s, 1H), 7.43 (dd, J = 1.1, 7.0 Hz, 1H), 7.47-7.57 (m, 3H), 7.85-7.99 (m, 3H).

46 — (3R)-7-Cyclopropyl-2,2-dimethyl-6-[(1-naphthyl)methyl]-4-oxo-1-thia-3a-aza-3-indancarboxylic acid ¹H NMR (400 MHz, CDCl3): δ = 13.50 (br s, 1H), 7.98-7.96 (m, 1H), 7.92-7.87 (m, 2H), 7.55-7.48 (m, 3H), 7.38 (d, J = 6.8 Hz, 1H), 5.22 (s, 1H), 4.80 (s, 1H), 4.49-4.40 (m, 2H), 1.73-1.67 (m, 1H), 1.58 (s, 3H), 1.53 (s, 3H), 0.96-0.82 (m, 2H), 0.73-0.60 (m, 2H) ppm. HRMS calc: [M + H+]: 406.1470; found: 406.1510

47 — (3R)-6-[(1-Naphthyl)-methyl]-4-oxo-7-(trifluoromethyl)-1-thia-3a-aza-3-indancarboxylic acid TABLE 1-continued

| Example Number | Chemical Structure ¹H-NMR and and HRMS data | IUPAC name |
|---|---|---|
| | ¹H NMR, 400 MHz, (DMSO) δ 3.62 (dd, J = 1.2, 11.9 Hz, 1H), 3.88 (dd, J = 9.2, 11.9 Hz, 1H), 4.38 (s, 2H), 5.40 (s, 1H), 5.46 (d, J = 9.2 Hz, 1H), 7.39-7.42 (m, 1H), 7.49-7.58 (m, 3H), 7.74-7.80 (m, 1H), 7.89-7.94 (m, 1H), 7.96-8.01 (m, 1H). | |
| 48 | | (3R)-7-Isobutoxy-6-[(1-naphthyl)methyl]-4-oxo-1-thia-3a-aza-3-indancarboxylic acid |
| | ¹H NMR, 400 MHz, (DMSO) δ 0.92-0.96 (m, 6H), 1.88-1.99 (m, 1H), 3.52-3.61 (m, 2H), 3.68 (dd, J = 6.4, 8.6 Hz, 1H), 3.87 (dd, J = 8.9, 11.9 Hz, 1H), 4.29 (dd, J = 16.9, 23.5 Hz, 2H), 5.33 (dd, J = 1.5, 8.9 Hz, 1H), 5.36 (s, 1H), 7.41-7.44 (m, 1H), 7.48-7.57 (m, 3H), 7.86-7.98 (m, 3H). | |
| 49 | | (3R)-7-Cyclopropyl-6-[(2-methoxy-1-naphthyl)methyl]-4-oxo-1-thia-3a-aza-3-indancarboxylic acid |
| | ¹H NMR, 400 MHz, (DMSO-d6, 400 MHz): δ = 13.33 (bs, 1H), 7.97 (d, 1H, J = 8.8 Hz), 7.92 (dd, 1H, J = 1.2, 8.4 Hz), 7.69 (d, 1H, J = 8.4 Hz), 7.53 (d, 1H, J = 9.2 Hz), 7.47 (ddd, 1H, J = 1.2, 6.8, 8.5 Hz), 7.39-7.34 (m, 1H), 5.29 (dd, 1H, J = 1.6, 9.2 Hz), 4.94 (s, 1H), 4.42 (d, 1H, J = 18 Hz), 4.33 (d, 1H, J = 18 Hz), 3.91 (s, 3H), 3.79 (dd, 1H, J = 2.8, 9.2 Hz), 3.49 (dd, 1H, J = 1.6, 11.6 Hz), 1.91-1.85 (m, 1H), 1.09-0.97 (m, 2H), 0.83-0.78 (m, 1H), 0.73-0.67 (m, 1H) ppm. | |
| 50 | | (3R)-7-(Cyclopropyl-methoxy)-6-[(1-naphthyl)methyl]-4-oxo-1-thia-3a-aza-3-indancarboxylic acid |
| | ¹H NMR, 400 MHz, (DMSO) δ 0.24-0.30 (m, 2H), 0.51-0.57 (m, 2H), 1.11-1.24 (m, 1H), 3.57 (dd, J = 1.7, 11.9 Hz, 1H), 3.71 (dABq, J = 7.2, 14.5 Hz, 2H), 3.87 (dd, J = 8.9, 11.9 Hz, 1H), 4.31 (dd, J = 16.6, 28.4 Hz, 2H), 5.31-5.35 (m, 2H), 7.41-7.45 (m, 1H), 7.47-7.57 (m, 3H), 7.85-7.99 (m, 3H). | |
| 51 | | 7-Cyclopropyl-6-[(2-methyl-1-aza-2-bora-1H-naphth-5-yl)-methyl]-4-oxo-1-thia-3a-aza-3-indan-carboxylic acid |

TABLE 1-continued

| Example Number | Chemical Structure<br>¹H-NMR and and HRMS data | IUPAC name |
|---|---|---|
| 52 | | 7-Cyclopropyl-6-[(2-methyl-1-aza-2-bora-1H-naphth-5-yloxy)methyl]-4-oxo-1-thia-3a-aza-3-indancarboxylic acid |
| 53 | | 7-Cyclopropyl-6-[(2-methyl-1-aza-2-bora-1H-naphth-8-yl)methyl]-4-oxo-1-thia-3a-aza-3-indancarboxylic acid |
| 54 | | 7-Cyclopropyl-6-[(2-methyl-1-aza-2-bora-1H-naphth-8-yloxy)methyl]-4-oxo-1-thia-3a-aza-3-indancarboxylic acid |

Intermediates

Benzyl (4R)-2-(cyclopropylmethyl)Δ²-1,3-thiazoline-4-carboxylate

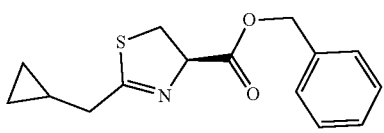 [SMILES: O=C(OCc1ccccc1)[C@@H]1CSC(CC2CC2)=N1]

Et₃N (0.28 mL, 206 mg, 2.0 mmol) was added, at RT, to a solution of (R)-Cysteine benzyl ester hydrochloride (506 mg, 2.0 mmol) and 2-cyclopropyl-1-ethoxy-1-ethanimine hydrochloride (368 mg, 2.2 mmol) in dry CH₂Cl₂ (20 mL). Precipitation started within minutes after addition of Et₃N. The reaction mixture was stirred at RT for 18 h and diluted with CH₂Cl₂. NaHCO₃ (sat aq, 10 mL) was added and the phases were separated. The aqueous phase was extracted with CH₂Cl₂ and the combined organic phases were dried (Na₂SO₄), filtered and concentrated in vacuo to afford 587 mg pale yellow oil. Purification by column chromatography (Biotage 50 g, 10-30% EtOAc in heptane) afforded 324 mg (58%) of the product as a pale yellow oil. ¹H NMR (600 MHz, CHCl₃): δ 7.35 (m, 5H), 5.24 (dd, J=12.6, 22.8 Hz, 2H), 5.10 (m, 1H), 3.53 (m, 2H), 2.46 (m, 2H), 0.98 (m, 1H), 0.57 (m, 2H), 0.22 (m, 2H).

5-{1-Hydroxy-2-[m-(trifluoromethyl)phenyl]ethylidene}-2,2-dimethyl-1,3-dioxane-4,6-dione

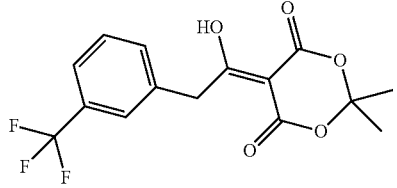 [SMILES: CC1(C)OC(=O)C(=C(O)Cc2cccc(C(F)(F)F)c2)C(=O)O1]

3-(Trifluoromethyl)phenylacetic acid (1.22 g, 6.0 mmol), Meldrum's acid (908 mg, 6.3 mmol) and DMAP (770 mg, 6.3 mmol) was dissolved in CH₂Cl₂ (20 mL) and cooled to 0° C. DCC (1 M in CH₂Cl₂, 7.8 mL, 7.8 mmol) was added drop-wise to the cooled solution that was stirred at 0° C. for 2 h and then over night at RT. KHSO₄ (6% aq. 12 mL) was added and the resulting precipitate was filtered off. The filtrate was washed with KHSO$_4$ (6% aq. 5×20 mL), H$_2$O (20 mL), brine (20 mL), dried (Na$_2$SO$_4$) and concentrated in vacuo. The afforded pink solid as suspended in CH$_2$Cl$_2$, the suspension as filtered and concentrated in vacuo to afford 2.03 g of a dark purple solid. This was the titled product, although not 100% pure. However, the purity was good enough to continue with.

$^1$H NMR (400 MHz, CHCl$_3$): δ15.37 (br s, 1H), 7.67-7.62 (m, 1H), 7.61-7.53 (m, 2H), 7.48-7.42 (m, 1H), 4.48 (s, 2H), 1.73 (s, 6H)

Benzyl (3R)-7-cyclopropyl-4-oxo-6-{[m-(trifluoromethyl)phenyl]methyl}-1-thia-3a-aza-3-indancarboxylate

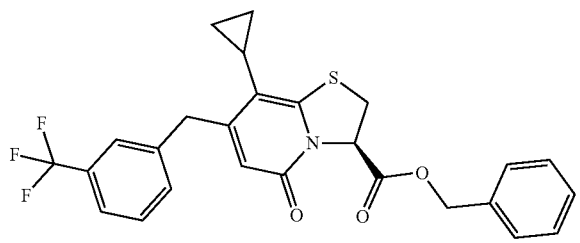 [SMILES: O=C(OCc1ccccc1)[C@@H]1CSc2c(C3CC3)c(Cc3cccc(C(F)(F)F)c3)cc(=O)n21]

TFA (84 µL, 0.11 mmol) was added to a solution of Benzyl (4R)-2-(cyclopropylmethyl)Δ$^2$-1,3-thiazoline-4-carboxylate (151 mg, 0.55 mmol) and 5-{1-Hydroxy-2-[m-(trifluoromethyl)phenyl]ethylidene}-2,2-dimethyl-1,3-dioxane-4,6-dione (543 mg, 1.65 mmol) in DCE (15 mL). Heated by MW at 120° C. for 2 min 30 sec. The reaction mixture was cooled to RT, diluted with CH$_2$Cl$_2$ (40 mL) and NaHCO$_3$ (sat aq, 5 mL) and H$_2$O (5 mL) were added. The phases were separated and the aqueous phase extracted with CH$_2$Cl$_2$ (3×15 mL). The combined organic phases were dried (Na$_2$SO$_4$) and concentrated in vacuo to afford 586 mg brown oil. Two consecutive purifications by column chromatography (first Biotage 50 g, 30-85% EtOAc in heptane and then 10 g Biotage) gave 69 mg (26%) of the product as pale yellow amorphous solid. $^1$H NMR (600 MHz, CHCl$_3$): δ 7.49 (m, 1H), 7.45 (m, 1H), 7.40 (m, 1H), 7.34-7.29 (m, 6H), 5.99 (s, 1H), 5.64 (dd, 1.8, 8.4 Hz, 1H), 5.22 (dd, 12, 19 Hz, 2H), 4.07 (d, 15.6 Hz, 1H), 3.98 (d, 16 Hz, 1H), 3.63 (dd, 9.0, 12.0 Hz, 1H), 3.47 (dd, 2, 12 Hz, 1H), 1.36 (m, 1H), 0.92 (m, 1H), 0.85 (m, 1H), 0.62 (m, 2H) ppm.

Methyl (3R)-7-cyclopropyl-4-oxo-6-{[m-(trifluoromethyl)phenyl]methyl}-1-thia-3a-aza-3-indancarboxylate

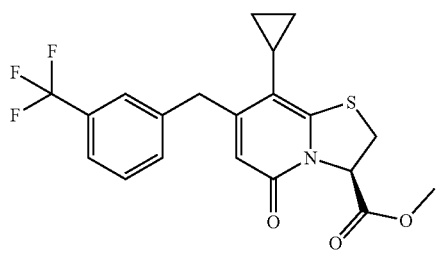 [SMILES: COC(=O)[C@@H]1CSc2c(C3CC3)c(Cc3cccc(C(F)(F)F)c3)cc(=O)n21]

$^1$H NMR (400 MHz, CHCl$_3$): δ 7.48-7.52 (m, 1H), 7.35-7.46 (m, 3H), 5.99-6.01 (m, 1H), 5.61 (dd, J=2.3, 8.6 Hz, 1H), 4.09 (d, J=16.0 Hz, 1H), 3.99 (d, J=16.0 Hz, 1H), 3.80 (s, 3H), 3.66 (dd, J=8.6, 11.6 Hz, 1H), 3.50 (dd, J=2.3, 11.6 Hz, 1H), 1.33-1.42 (m, 1H), 0.83-0.97 (m, 2H), 0.60-0.70 (m, 2H).

Biology

Biofilm inhibition of *Mycobacterium tuberculosis*

The compounds of Examples 1-50 were dissolved in DMSO and tested for biofilm inhibition of *Mycobacterium tuberculosis*, as described below at concentrations of 10 microM, 25 microM, 50 microM and/or 100 microM. The measurement of biofilm inhibition was made by ocular inspection of the tested tuberculosis bacteria. For each concentration, three or more measurements were made and then an average value was calculated. For each measurement, the biofilm inhibition was considered to be complete, partial or not taking place. Complete or full biofilm inhibition means that none of the tested tuberculosis bacteria exhibit biofilm, i.e. the inhibition is 100%. Partial biofilm inhibition means the tuberculosis bacteria exhibit a disrupted and/or limited biofilm. For simplicity of calculation, an inhibition value of 50% was set when partial biofilm inhibition was observed. Biofilm inhibition was considered not to take place if all tested tuberculosis bacteria exhibited biofilm, i.e. biofilm inhibition was 0%.

Some of the compounds of Examples 1-54 were also tested to find a concentration at which full biofilm inhibition took place. The result is shown in Table 2 below, and all compounds tested in this way were found to have satisfactory biofilm inhibition, i.e. as shown in the column "Full Biofilm inhibition at μM" in Table 2.

The measurement of biofilm inhibition of *Mycobacterium tuberculosis* took place as follows. Bacterial biofilms were inoculated with stationary phase planktonic cultures of *Mycobacterium tuberculosis* Erdman into Sauton's media (available from HiMedia laboratories) at a 1:100 dilution and incubated at 37° C. in 5% $CO_2$. Culture vessels were closed tightly to restrict oxygen for 3 weeks, and then vented. When a compound of Examples 1-50 was included, it was added to biofilm cultures at the time of inoculation. In all assays performed with a compound of Examples 1-50, control samples were treated with DMSO vehicle. It was checked that at the concentrations used, there was no effect of DMSO itself on biofilm formation or Mtb physiology.

Crystal Violet Staining.

Biofilms were cultured as just described in 96-well plates in the presence and absence of Example 1-50, media was aspirated, and plates were gently washed with water 3 times. Plates were stained with 0.5% crystal violet for 15 minutes, washed 3 times in water, and air dried. To quantify staining, 45% acetic acid was used to destain each well, diluted 1:10 in formalin, and read at $OD\lambda_{600}$.

Stress and Tolerance Assays in Biofilm Conditions.

Mtb was grown in biofilm-forming conditions in Sauton's medium in the presence and absence of Example 1-50. After 3 weeks, seals on the vessels were opened, and concentrated solutions of antibiotics or $H_2O_2$ were pipetted underneath the surface of the culture. After 2 weeks of exposure to the indicated stress, bacteria were harvested from each well, centrifuged to pellet, and resuspended in 1% Tween 80 in phosphate-buffered saline (PBS). Glass beads were added to each tube and tubes were shaken overnight at room temperature to disassociate bacteria. Serial dilutions were plated to enumerate CFUs.

Stress and Tolerance Assays in Aerated, Planktonic Conditions.

For aerated growth curves, Mtb was inoculated into Sauton's medium containing 0.05% Tween 20 at an optical density of 0.08. DMSO (control), 25 µM of the compound of Example 1, or 0.25 µg/ml INH were added as indicated. Changes in $OD\lambda_{600}$ were monitored. After ten days of planktonic growth, cultures were plated on 7H11 agar plates to enumerate bacterial CFUs. The 7H11 agar plates (available from SigmaAldrich). For pH and nitrosative stress assays, Mtb was grown in Sauton's medium containing 0.05% Tween 80 in the presence and absence of MTIs and at the indicated pH and NaNO concentrations at 37° C. At the indicated times, cultures were pipetted to mix and a small sample was removed to plate for CFUs.

The results of the biofilm inhibition measurements are shown in Table 2.

TABLE 2

| Example Number | Average % Inhibition at | | | | Full Biofilm inhibition at µM |
|---|---|---|---|---|---|
| | 10 µM | 25 µM | 50 µM | 100 µM | |
| 1 | 100 | 100 | | | 2.5 µM, 7.5 µM, 2.5 µM, 10 µM |
| 2 | 63 | 100 | 75 | | 25 µM, 25 µM |
| 3 | 100 | 100 | 100 | | 50 µM |
| 4 | 100 | 100 | 100 | | 25 µM, 25 µM, 25 µM |
| 5 | 100 | 100 | 100 | | 5 µM, 5 µM |
| 6 | 50 | 88 | 100 | 100 | 30 µM, 30 µM, 30 µM |
| 7 | 50 | 100 | 100 | | 25 µM, 25 µM, 25 µM |
| 8 | 75 | 63 | 75 | | 25 µM, 25 µM |
| 9 | 50 | 87 | 87 | | 25 µM, 25 µM |
| 10 | 69 | 100 | 100 | | |
| 11 | 75 | 38 | 88 | | |
| 12 | 12 | 50 | 87 | | |
| 13 | 62 | 75 | 100 | | 50 µM, 50 µM |
| 14 | 0 | 88 | 100 | | |
| 15 | 87 | 100 | 100 | | 50 µM |
| 16 | 25 | 62 | 100 | | |
| 17 | 25 | 38 | 100 | | 50 µM, 50 µM |
| 18 | 12 | 12 | 38 | | |
| 19 | 0 | 0 | 88 | 100 | |
| 20 | 75 | 100 | 100 | | 25 µM, 25 µM, |
| 21 | 12 | 100 | 100 | | |
| 22 | | 38 | 25 | | |
| 23 | | 12 | 50 | | |
| 24 | | 12 | 62 | | |
| 25 | | 12 | 50 | | |
| 26 | | | | | 50 µM |
| 27 | 75 | 88 | 100 | | 25 uM, 25 µM, 25 µM |
| 28 | | | | | 50 µM, 50 µM |
| 29 | | | | | 50 µM, 50 µM |
| 30 | | | | | 50 uM |
| 31 | | | 100 | | |
| 32 | | | | | 50 µM, 50 µM |
| 33 | | | | | 25 µM, 25 µM, 25 µM |
| 34 | | | 25 | | 30 µM, 30 µM, 30 µM |
| 35 | | 25 | | 75 | 50 µM, 50 µM |
| 36 | 100 | 100 | 100 | | |
| 37 | 100 | 100 | 100 | | |
| 38 | 100 | 100 | 100 | | 25 µM, 25 µM, 25 µM |
| 39 | 50 | 100 | 100 | | |
| 40 | 50 | 100 | 50 | | |
| 41 | 25 | 62 | 88 | 100 | |
| 42 | 50 | 12 | 12 | | |
| 43 | | 50 | 100 | | |
| 44 | 25 | 75 | 100 | | |
| 45 | | 50 | 25 | | |
| 46 | | 62 | 38 | | |
| 47 | | | 100 | | >50 µM |
| 48 | | 50 | | | |
| 49 | | | | | 25 µM, 25 µM, 25 µM |
| 50 | | 25 | | | |

Treatment of *Mycobacterium tuberculosis* Bacteria with Isoniazid in the Absence or Presence of the Compound (3R)-7-Cyclopropyl-6-[(1-naphthyl)methyl]-4-oxo-1-thia-3a-aza-3-indancarboxylic Acid, i.e. the Compound of Example 1

FIG. 5*a* shows an agar plate containing 0.05% DMSO and inoculated with $1.959\times10^8$ CFU of *Mycobacterium tuberculosis* and a disk spotted with 5 μl of water placed onto the plate at the time of inoculation. Photo was taken after 4 weeks of incubation at 37° C. in 5% $CO_2$.

FIG. 5*b* shows an agar plate containing 0.05% DMSO and inoculated with $1.959\times10^8$ CFU of *Mycobacterium tuberculosis* and a disk spotted with 5 μl of 0.5 mg/ml INH placed onto the plate at the time of inoculation. Photo was taken after 4 weeks of incubation at 37° C. in 5% $CO_2$.

FIG. 5*c* shows an agar plate containing a DMSO solution of 25 μM (3R)-7-Cyclopropyl-6-[(1-naphthyl)methyl]-4-oxo-1-thia-3a-aza-3-indancarboxylic acid and inoculated with $1.959\times10^8$ CFU of *Mycobacterium tuberculosis* and a disk spotted with 5 μl of water placed onto the plate at the time of inoculation. Photo was taken after 4 weeks of incubation at 37° C. in 5% $CO_2$.

FIG. 5*d* shows an agar plate containing a DMSO solution of 25 μM (3R)-7-Cyclopropyl-6-[(1-naphthyl)methyl]-4-oxo-1-thia-3a-aza-3-indancarboxylic acid and inoculated with $1.959\times10^8$ CFU of *Mycobacterium tuberculosis* and a disk spotted with 5 μl of 0.5 mg/ml INH placed onto the plate at the time of inoculation. Photo was taken after 4 weeks of incubation at 37° C. in 5% $CO_2$.

For FIG. 6, Mtb was innoculated into Sauton's medium in the presence of the compound of Example 1 and the compound of Example 19, 25 μM respectively, and in the absence of the compound of Example 1 and the compound of Example 19, respectively, and sealed to restrict oxygen. After 3 weeks, seals on the vessels were opened, and INH at the indicated concentration was pipetted underneath the surface of the culture. After 2 weeks of exposure to the INH, bacteria were harvested from each well, centrifuged to pellet, and resuspended in 1% Tween 80 in phosphate-buffered saline (PBS). Glass beads were added to each tube and tubes were shaken overnight at room temperature to disassociate bacteria. Serial dilutions were plated to enumerate colony forming units. FIG. 6 shows the ratio of colony forming units of treated and untreated tuberculosis bacteria as a function of the concentration of added isoniazid, added combination of isoniazid and the compound of Example 1 and added combination of isoniazid and the compound of Example 19, respectively. In the graph "Control" means that only isoniazid and DMSO were added, "Example 1" means that a combination of isoniazid and the compound of Example 1 was added, and "Example 19" means that a combination of isoniazid and the compound of Example 19 was added. In the graph, the concentration refers to the concentration of isoniazid. The concentration of the compound of Example 1 and Example 19, respectively, was 50 microM and 25 microM, respectively. It can be seen that tuberculosis bacteria remained when treatment was performed with isoniazid alone (control). However, no tuberculosis bacteria could be detected when isoniazid was used in combination with the compound of Example 1 or in combination with the compound of Example 19. In this document, ND stands for none detected, i.e. tuberculosis bacteria could not be detected.

The following conclusions can be drawn from the above experiments.

Isoniazid alone, i.e. in the absence of (3R)-7-Cyclopropyl-6-[(1-naphthyl)methyl]-4-oxo-1-thia-3a-aza-3-indancarboxylic acid and the compound of Example 19, did not eradicate *Mycobacterium tuberculosis*.

(3R)-7-Cyclopropyl-6-[(1-naphthyl)methyl]-4-oxo-1-thia-3a-aza-3-indancarboxylic acid alone, i.e. in the absence of isoniazid, did not eradicate *Mycobacterium tuberculosis*.

A combination of isoniazid and the compound of example 1 (i.e. (3R)-7-Cyclopropyl-6-[(1-naphthyl)methyl]-4-oxo-1-thia-3a-aza-3-indancarboxylic acid) eradicated *Mycobacterium tuberculosis*.

A combination of isoniazid and the compound of Example 19 (i.e. 8-Benzyl-5-cyclopropyl-4-[(1-naphthyl)methyl]-2-oxo-7-thia-1-azabicyclo[4.3.0]nona-3,5,8-triene-9-carboxylic acid) eradicated *Mycobacterium tuberculosis*.

Comparison of Treatment of Wild-Type *Mycobacterium tuberculosis* Bacteria with Treatment of *Mycobacterium tuberculosis* Bacteria Characterized by Mutations in the Catalase katG Treatment of Erdman Wild-Type *Mycobacterium tuberculosis* Bacteria The effect of (3R)-7-Cyclopropyl-6-[(1-naphthyl)methyl]-4-oxo-1-thia-3a-aza-3-indancarboxylic acid (Example 1) on INH sensitivity was demonstrated by incubating planktonic, aerated Mtb cultures containing 25 μM Example 1 and/or 0.25 μg/ml INH, which is approximately ten times the MIC of INH (0.02-0.06 μg/ml), and monitoring growth as changes in OD$\lambda_{600}$ over time. A comparison was made with a control, which contained no compound of Example 1 and no INH.

FIG. 8a shows that under these conditions, Example 1 alone slowed the growth of Mtb, increasing the doubling time from 29 hours to 52 hours, demonstrating that Example 1 has a relatively minor but significant impact on Mtb growth. Treatment with INH or the INH+Example 1 combination completely inhibited Mtb growth, as measured by OD$\lambda_{600}$.

FIG. 8b shows the determination of effects on Mtb viability. Samples were harvested from each growth curve culture 240 hours post inoculation and plated to enumerate colony forming units (CFU). Treatment with Example 1 resulted in 7.6 fold less Mtb in the culture as compared to controls, supporting that this compound alone has some growth inhibitory properties. Although treatment with INH alone or the combination INH+Example 1 inhibited growth as measured by OD$\lambda_{600}$, only the combination of INH+Example 1 eliminated all of the culturable bacteria. In contrast, several thousand CFU/ml remained viable in the cultures treated with INH alone for 10 days, which reflects the bacteriostatic nature of this antibiotic.

FIGS. 8c-8f show a lawn of the WT strain plated on agar. FIG. 8c shows the experiment run as a control, i.e. no compound of example 1 and no INH were present. FIG. 8d shows the experiment run in the presence of INH. FIG. 8e shows the experiment run in the presence of Example 1. FIG. 8f shows the experiment run in the presence of the combination of Example 1 and INH. It was observed that only the combination of the compound of Example 1 and INH eradicated the WT Mtb.

The results shown in FIGS. 8a and 8b demonstrate that INH+Example 1 synergize with each other to result in a bactericidal outcome. The conclusion is that this combination can shorten the treatment time.

Treatment of *Mycobacterium tuberculosis* INH-Resistant Bacteria with a Mutation in the Catalase katG This experiment was performed in analogy with the experiment above in which WT Mtb was used, but Mtb with a mutation in the catalase katG was used instead of WT Mtb. The INH-resistant strain was derived by playing the Erdman WT strain onto plates containing isoniazid and selecting for resistant colonies of bacteria. Before use the katG gene was sequenced to determine the mutation.

Mtb resistance to INH generally occurs by mutations in the catalase katG. When an Mtb isolate with a frameshift at amino acid 6 in katG (katGFSAA6) was grown in planktonic cultures in the presence or absence of 25 μM of the compound of Example 1, 0.25 μg/ml of INH, or a combination of INH and the compound of Example 1. A comparison was made with a control, which contained no compound of Example 1 and no INH.

Figure 9A:
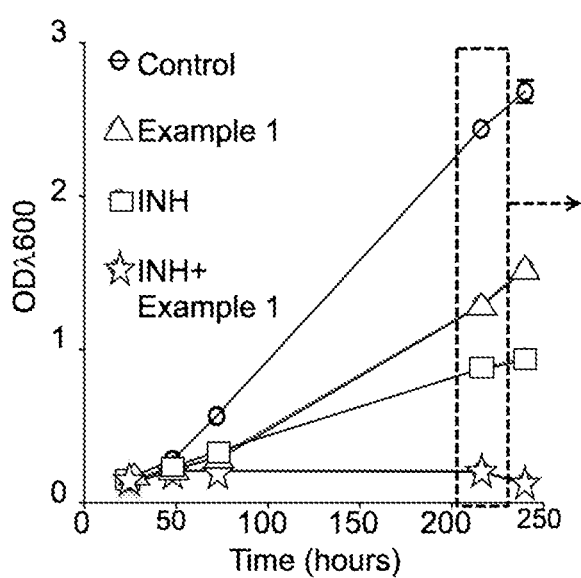
FIG. 9a shows katGFASAA6 Mtb growth in planktonic, aerated cultures.

FIG. 9a shows that the compound of Example 1 alone reduced the doubling time of the katGFSAA6 strain from 23 to 48 hours. This is similar to what was observed in the WT Mtb (FIG. 8a). The katGFSAA6 strain was significantly more resistant to INH alone and was able to grow in the presence of INH with a doubling time of 55 hours, whereas WT Mtb growth was undetectable in planktonic cultures the presence of INH (FIG. 8a).

Figure 9B:
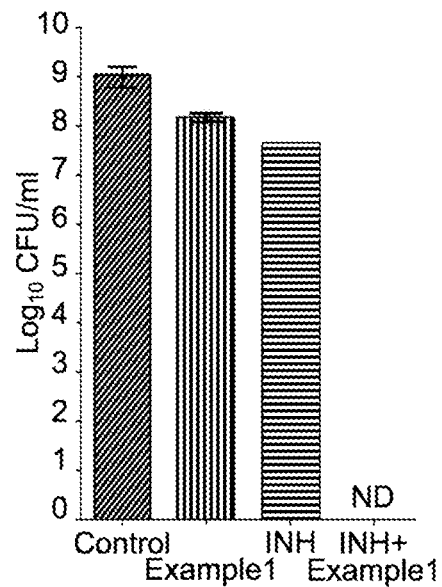
FIG. 9b shows katGFASAA6 Mtb plated for CFUs to determine live Mtb.

FIG. 9b, however, shows that in the presence of the combination INH+Example 1, the katGFSAA6 strain was unable to replicate based on OD$\lambda_{600}$ and when we plated bacteria from these planktonic cultures after 10 days, no culturable CFU remained.

Figure 9C:
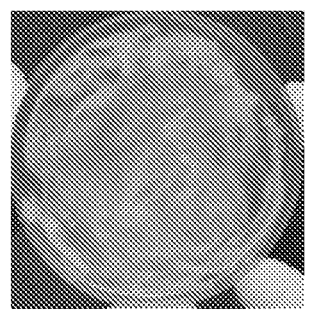
FIG. 9c a photograph of shows growth of plated katGFASAA6 Mtb on an agar plate when INH and the compound of Example 1 were absent.
Figure 9D:
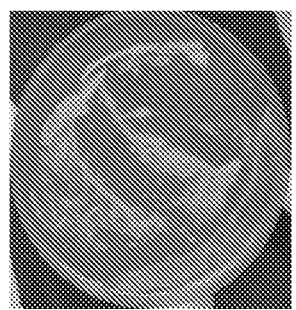
FIG. 9d shows a photograph of growth of plated katGFASAA6 Mtb on an agar plate for INH.
Figure 9E:
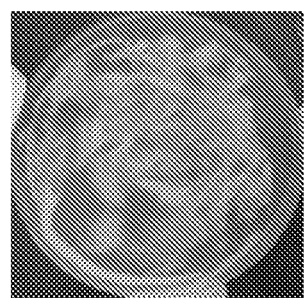
FIG. 9e shows a photograph of growth of plated katGFASAA6 Mtb on an agar plate for the compound of Example 1.
Figure 9F:
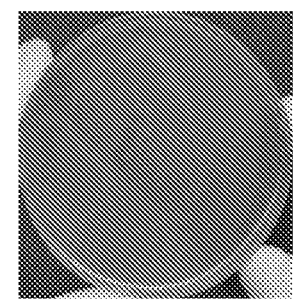
FIG. 9f shows a photograph of growth of plated katGFASAA6 Mtb on an agar plate for a combination of INH and the compound of Example 1.

FIGS. 9c-9f show a lawn of the katGFSAA6 strain plated on agar. FIG. 9c shows an experiment run as a control, i.e. no compound of example 1 and no INH were present. FIG. 9d shows the experiment run in the presence of INH. FIG. 9e shows the experiment run in the presence of the compound of Example 1. FIG. 9f shows the experiment run in the presence of the combination of the compound of Example 1 and INH. It was observed that for experiments containing Example 1 or INH alone, the mutant was able to grow (FIGS. 9d and 9e). In contrast, as shown in FIG. 9f, the katGFSAA6 strain did not grow on agar in the presence of INH+Example 1, demonstrating that these bacteria are sensitive to this combination. The inability to isolate colonies on plates containing INH+Example 1 indicates that the combination is toxic for all katG mutants that normally grow in the presence of INH.

Together these data show that the combination of INH+Example 1 blocks the growth and survival of INH-resistant katG mutants, thus restoring the sensitivity of katG mutants to INH treatment.

Further Comments Regarding the Results Shown in FIG. 8 and FIG. 9, Respectively.

FIGS. 8a-8b show the results for WT Mtb and FIG. 9a-9b katGFSAA6 Mtb, respectively, grown in planktonic conditions in the presence of 0.25 μg/ml INH, 25 μM Example 1 or a combination. Culture absorbance was measured over time and CFUs were plated at 10 days post inoculation. Error bars represent the range of two samples. Significance of the differences was determined by calculating P values by ANOVA. * $P<0.05$.  $P<0.01$. * $P<0.001$. **** $P<0.0001$. (B, E) ND=Not detected; Limit of Detection=1 CFU/ml. (c) The WT or (f) katGFSAA6 Mtb strain was plated onto Sautons agar plates containing INH, Example 1, or a combination of INH+Example 1. It was concluded that a combination of INH and the compound of Example 1 eradicated WT Mtb and also eradicated Mtb with a mutation in katGFSAA6.

The invention claimed is:

1. A method for treatment of tuberculosis comprising administering to a mammal in need of treatment thereof an effective amount of a drug against tuberculosis, or a pharmaceutically acceptable salt thereof; and an effective amount of a compound of Formula II

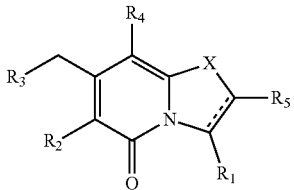

or a pharmaceutically acceptable salt thereof, wherein
$R_1$ is selected from the group consisting of:
a) C(O)OH,
b) tetrazolyl,
c) $CH_2OH$,
d) $C(O)NR_{6a}R_{6b}$,
e) $C(O)NHSO_2R_7$,
f) $C(O)OR_8$,
g) $NH_2$,
h) H,
i)

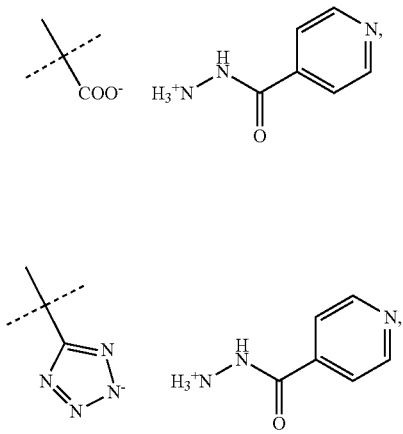

j)

and
k)

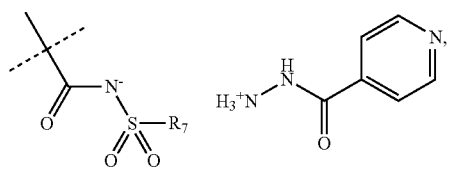

$R_2$ is selected from the group consisting of:
a) H
b) Cl, F, Br or I,
c) $CH_2OH$,
d) $C_1$-$C_4$alkyl, and
e) $NY_1Y_2$, $R_3$ is selected from the group consisting of:
a) 1-naphtyl, 2-naphtyl, and 1-naphtyloxy, each independently substituted with 0, 1, 2 or 3 substituents selected from the group consisting of methyl, fluoro, chloro, bromo, cyano, and methoxy,
b) phenyl substituted with 0,1, 2 or 3 substituents independently selected from the group consisting of methyl, fluoro, chloro, cyano, and trifluoromethyl,
c) aminophenyl substituted with 0,1, 2 or 3 substituents independently selected from the group consisting of methyl, fluoro, chloro, and trifluoromethyl,
d) 2-(3-methyl)phenylmethylene,
e) benzothiophen-2-yl,
f) H or $C_{1-C4}$-alkyl,
g) 2-methyl-1-aza-2-bora-1H-naphth-5-yloxy, and
h) 2-methyl-1-aza-2-bora-1H-naphth-5-yl, $R_4$ is selected from the group consisting of:
a) $C_{1-C4}$alkyl substituted by 0, 1, 2, 3 or 4 fluoro;
b) $C_3$-$C_6$cycloalkyl,
c) $C_1$-$C_4$alkoxy substituted by 0, 1, 2, 3 or 4 fluoro,
d) $C_3$-$C_6$cycloalkoxy,
e) a 3-, 4-, 5-or 6-membered heterocycle,
f) N-methyl 3-indolyl, and
g) $NR_9R_{10}$, $R_5$ is selected from the group consisting of:
a) H
b) phenyl substituted with 0, 1, 2 or 3 methyl group(s),
c) benzyl,
d) thienyl,
e) $C_1$-$C_4$alkoxy, and
f) 3-, 4-, 5-or 6-membered heterocycle, and in the above definitions:

$R_{6a}$ is selected from the group consisting of H and $C_1$-$C_4$alkyl,
$R_{6b}$ is selected from the group consisting of H, $C_1$-$C_4$alkoxy, and isonicotinoylamino;
$R_7$ is $C_1$-$C_4$alkyl or phenyl,
$R_8$ represents 2-{2-[1-(hydroxymethyl)propylamino] ethylamino}butyl),
$R_{9a}$ represents $C_1$-$C_4$ alkyl,
$R_{9b}$ represents $C_1$-$C_4$alkyl,
$R_{10}$ represents $C_1$-$C_4$alkyl, or
$R_9$ and $R_{10}$ together form $CH_2(CH_2)_m CH_2$,
$Y_1$ and $Y_2$ each independently represents hydrogen, methyl, $CH_3S(O)_2$ or $C(O)CH_3$, or
$Y_1$ and $Y_2$ together form $CH_2CH_2CH_2CH_2$ or $CH_2CH_2CH_2CH_2CH_2$,
m is 1, 2 or 3, and
X is S, SO or $SO_2$, thereby treating tuberculosis.

2. The method according to claim 1, wherein the compound of Formula II is a compound of Formula IIa or Formula IIb:

Formula IIa

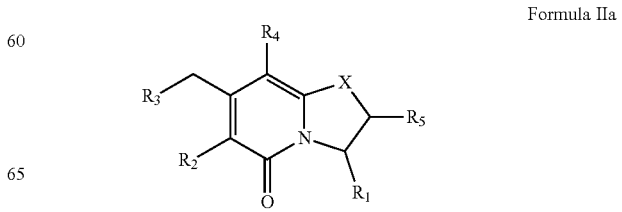

-continued

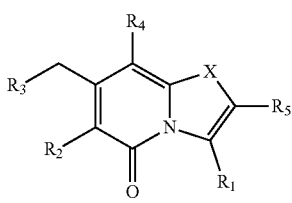

Formula IIb wherein $R_1$, $R_2$, $R_3$, $R_4$, $R_5$ and X are as defined in claim 1, or a pharmaceutically acceptable salt thereof.

3. The method according to claim 1, wherein the compound of Formula II is a compound of Formula IIa51:

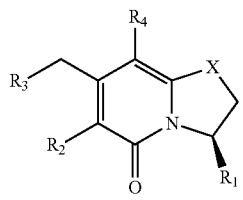

Formula IIa51 wherein
$R_1$, $R_2$, $R_3$, $R_4$ and X are as defined in claim 1,
or a pharmaceutically acceptable salt thereof.

4. The method according to claim 1, wherein X is S or SO.

5. The method according to claim 1, wherein $R_1$ is C(O)OH, tetrazolyl, or C(O)NHSO$_2$R$_7$.

6. The method according to claim 1, wherein $R_2$ is H.

7. The method according to claim 1, wherein $R_3$ is selected from the group consisting of:
   a) 1-naphtyl, 2-naphtyl, and 1-naphtyloxy, each independently substituted with 0, 1, 2 or 3 substituents selected from the group consisting of methyl, fluoro, chloro, cyano, and methoxy, and
   b) phenyl substituted with 0, 1, 2 or 3 substituents independently selected from the group consisting of methyl, fluoro, chloro, cyano, and trifluoromethyl.

8. The method according to claim 1, wherein $R_4$ is cyclopropyl.

9. The method according to claim 1, wherein $R_5$ is H or phenyl substituted with 0, 1, 2 or 3 methyl group(s).

10. The method according to claim 1, wherein the compound of Formula II is selected from the group consisting of:
   (3R)-7-Cyclopropyl-6-[(1-naphthyl)methyl]-4-oxo-1-thia-3a-aza-3-indancarboxylic acid,
   (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid,
   (3R)-7-Cyclopropyl-6-[(4-fluoro-1-naphthyl)methyl]-4-oxo-1-thia-3a-aza-3-indancarboxylic acid,
   (3R)-7-Cyclopropyl-6-[(4-methyl-1-naphthyl)methyl]-4-oxo-1-thia-3a-aza-3-indancarboxylic acid,
   (3S)-7-Cyclopropyl-6-[(1-naphthyl)methyl]-4-oxo-1-thia-3a-aza-3-indancarboxylic acid,
   5-Cyclopropyl-4-[(1-naphthyl)methyl]-2-oxo-8-(3-thienyl)-7-thia-1-azabicyclo[4.3.0]nona-3,5,8-triene-9-carboxylic acid,
   (3R)-7-Cyclopropyl-6-[(1-naphthyloxy)methyl]-4-oxo-1-thia-3a-aza-3-indancarboxylic acid,
   (3R)-7-Cyclopropyl-6-[(2-fluoro-5-methyl-phenyl)methyl]-4-oxo-1-thia-3a-aza-3-indancarboxylic acid,
   (3R)-7-Cyclopropyl-4-oxo-6-[(2,3-xylyl)methyl]-1-thia-3a-aza-3-indancarboxylic acid,
   (3R)-7-Methyl-6-[(1-naphthyl)methyl]-4-oxo-1-thia-aza-3-indancarboxylic acid, (N-Methylmethoxyamino){(3R)-7-cyclopropyl-6-[(1-naphthyl)methyl]-4-oxo-1-thia-3a-aza-3-indanyl}formaldehyde,
   (3R)-7-Cyclopropyl-6-[(1-naphthyl)methyl]-3-(1H-1,2,3,4-tetrazol-5-yl)-1-thia-3a-aza-4-indanone,
   5-Cyclopropyl-4-[(1-naphthyl)methyl]-2-oxo-8-phenyl-7-thia-1-azabicyclo[4.3.0]nona-3,5,8-triene-9-carboxylic acid,
   5-Cyclopropyl-4-[(1-naphthyl)methyl]-2-oxo-8-(m-tolyl)-7-thia-1-azabicyclo[4.3.0]nona-3,5,8-triene-9-carboxylic acid,
   (3R)-7-Cyclopropyl-6-[(2-naphthyl)methyl]-4-oxo-1-thia-3a-aza-3-indancarboxylic acid,
   (3R)-7-Cyclopropyl-3-(hydroxymethyl)-6-[(1-naphthyl)methyl]-1-thia-3a-aza-4-indanone,
   (3R)-6-[(1-Naphthyl)methyl]-4-oxo-7-(2-thienyl)-1-thia-3a-aza-3-indancarboxylic acid,
   5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid,
   8-Benzyl-5-cyclopropyl-4-[(1-naphthyl)methyl]-2-oxo-7-thia-1-azabicyclo[4.3.0]nona-3,5,8-triene-9-carboxylic acid,
   (3R)-7-Cyclopropyl-6-[(2,3-dichlorophenyl)methyl]-4-oxo-1-thia-3a-aza-3-indancarboxylic acid,
   (3R)-7-Cyclopropyl-6-[(1-naphthyl)methyl]-4-oxo-1-thia-3a-aza-3-indancarboxamide,
   {(3R)-7-Cyclopropyl-6-[(1-naphthyl)methyl]-4-oxo-1-thia-3a-aza-3-indanyl}(phenylsulfonylamino)formaldehyde,
   (3R)-7-Isopropyl-6-[(1-naphthyl)methyl]-4-oxo-1-thia-3a-aza-3-indancarboxylic acid,
   (3R)-7-Cyclopropyl-6-methyl-4-oxo-1-thia-3a-aza-3-indancarboxylic acid,
   (3R)-6-[(p-Chlorophenyl)methyl]-7-cyclopropyl-4-oxo-1-thia-3a-aza-3-indancarboxylic acid,
   {(3R)-7-Cyclopropyl-6-[(1-naphthyl)methyl]-4-oxo-1-thia-3a-aza-3-indanyl}(methylsulfonylamino)formaldehyde,
   (3R)-7-Cyclopropyl-4-oxo-6-[(m-tolyl)methyl]-1-thia-3a-aza-3-indancarboxylic acid,
   (3R)-7-Isopropyl-4-oxo-6-[2-(m-tolyl)ethyl]-1-thia-3a-aza-3-indancarboxylic acid,
   7-(1-Methyl-1H-indol-3-yl)-6-[(1-naphthyloxy)methyl]-4-oxo-1-thia-3a-aza-3-indancarboxylic acid,
   (3R)-6-[(4-Bromo-1-naphthyl)methyl]-7-cyclopropyl-4-oxo-1-thia-3a-aza-3-indancarboxylic acid,
   7-Cyclopropyl-6-[(1-naphthyl)methyl]-1-thia-3a-aza-4-indanone,
   (3R)-7-Cyclopropyl-5-(hydroxymethyl)-6-[(1-naphthyl)methyl]-4-oxo-1-thia-3a-aza-3-indancarboxylic acid,
   (3S)-3-Amino-7-cyclopropyl-6-[(1-naphthyl)methyl]-1-thia-3a-aza-4-indanone,
   (2R,3R)-7-Cyclopropyl-6-[(1-naphthyl)methyl]-4-oxo-2-phenyl-1-thia-3a-aza-3-indancarboxylic acid,
   (2S,3R)-7-Cyclopropyl-2-methoxy-6-[(1-naphthyl)methyl]-4-oxo-1-thia-3a-aza-3-indancarboxylic acid,
   7-Cyclopropyl-4-oxo-6-{[m-(trifluoromethyl)phenyl]methyl}-1-thia-3a-aza-3-indancarboxylic acid,
   2-{2-[1-(Hydroxymethyl)propylamino]ethylamino}butyl 7-cyclopropyl-6-[(1-naphthyl)methyl]-4-oxo-1-thia-3a-aza-3-indancarboxylate, {7-Cyclopropyl-6-[(1-naphthyl)methyl]-4-oxo-1-thia-3a-aza-3-indanyl}(2-isonicotinoylhydrazino)formaldehyde, 7-Cyclopropyl-6-[(4-methoxy-1-naphthyl)methyl]-4-oxo-1-thia-3a-aza-3-indancarboxylic acid, (3R)-7-(Dimethylamino)-6-[(1-naphthyl)methyl]-4-oxo-1-thia-3a-aza-3-indancarboxylic acid, (3R)-5-Bromo-7-cyclopropyl-6-[(1-naphthyl)methyl]-4-oxo-1-thia-3a-aza-3-indancarboxylic acid, 7-Cyclopropyl-6-[(1-naphthyl)methyl]-1,1-dioxo-4-oxo-1-thia-3a-aza-3-indancarboxylic acid, (3R)-7-Cyclopropyl-4-oxo-6-[(2,3-xylidino)methyl]-1-thia-3a-aza-3-indancarboxylic acid, 7-Cyclopropyl-6-[(1-naphthyl)methyl]-1-oxo-4-oxo-1-thia-3a-aza-3-indancarboxylic acid, (3R)-7-Ethoxy-6-[(1-naphthyl)methyl]-4-oxo-1-thia-3a-aza-3-indancarboxylic acid, (3R)-6-[(1-Naphthyl)methyl]-4-oxo-7-(trifluoromethyl)-1-thia-3a-aza-3-indancarboxylic acid, (3R)-7-Isobutoxy-6-[(1-naphthyl)methyl]-4-oxo-1-thia-3a-aza-3-indancarboxylic acid (3R)-7-Cyclopropyl-6-[(2-methoxy-1-naphthyl)methyl]-4-oxo-1-thia-3a-aza-3-indancarboxylic acid, (3R)-7-(Cyclopropylmethoxy)-6-[(1-naphthyl)methyl]-4-oxo-1-thia-3a-aza-3-indancarboxylic acid, 7-Cyclopropyl-6-[(2-methyl-1-aza-2-bora-1H-naphth-5-yl)methyl]-4-oxo-1-thia-3a-aza-3-indancarboxylic acid, 7-Cyclopropyl-6-[(2-methyl-1-aza-2-bora-1H-naphth-5-yloxy)methyl]-4-oxo-1-thia-3a-aza-3-indancarboxylic acid, 7-Cyclopropyl-6-[(2-methyl-1-aza-2-bora-1H-naphth-8-yl)methyl]-4-oxo-1-thia-3a-aza-3-indancarboxylic acid, 7-Cyclopropyl-6-[(2-methyl-1-aza-2-bora-1H-naphth-8-yloxy)methyl]-4-oxo-1-thia-3a-aza-3-indancarboxylic acid, or a pharmaceutically acceptable salt of any of the foregoing compounds.

11. The method according to claim 1, wherein the compound of Formula II is selected from the group consisting of:

(3R)-7-Cyclopropyl-6-[(1-naphthyl)methyl]-4-oxo-1-thia-3a-aza-3-indancarboxylic acid, 7-Cyclopropyl-4-oxo-6-{[m-(trifluoromethyl)phenyl]methyl}-1-thia-3a-aza-3-indancarboxylic acid, and (3R)-7-Cyclopropyl-4-oxo-6-{(7-thiabicyclo[4.3.0]nona-1,3,5,8-tetraen-8-yl)methyl}-1-thia-3a-aza-3-indancarboxylic, or a pharmaceutically acceptable salt of any of the foregoing compounds.

12. The method according to claim 1, wherein the effective amount of the drug against tuberculosis or the pharmaceutically acceptable salt thereof and the effective amount of a compound of Formula II or the pharmaceutically acceptable salt thereof are provided in separate compositions.

13. The method according to claim 1, wherein the effective amount of the drug against tuberculosis or the pharmaceutically acceptable salt thereof and the effective amount of a compound of Formula II or the pharmaceutically acceptable salt thereof are provided in a single composition.

14. The method according to claim 1, wherein the drug against tuberculosis is at least one of the following: isonicotinylhydrazide, bedaquiline, ethionamide, pretomanid, 4-aminosalisalicylic acid, rifampicin, pyrazinamide, or ethambutol.

15. A method for sensitizing tuberculosis bacteria to treatment with a drug against tuberculosis comprising administering to a mammal in need thereof an effective amount of a compound of Formula II of claim 1, thereby sensitizing tuberculosis bacteria to treatment with a drug against tuberculosis.

16. The method according to claim 15, wherein the method further comprises, after the step of sensitizing tuberculosis bacteria to treatment with a drug against tuberculosis, administering to the mammal in need thereof an effective amount of a drug against tuberculosis, thereby treating tuberculosis.

17. The method according to Claim 1, wherein the administration of the effective amount of the drug against tuberculosis or the pharmaceutically acceptable salt thereof; and the effective amount of a compound of Formula II or the pharmaceutically acceptable salt thereof comprises administering the effective amount of a compound of Formula II or the pharmaceutically acceptable salt thereof is performed in one step, and administering the effective amount of the drug against tuberculosis or the pharmaceutically acceptable salt thereof is performed in a step separate from the step of administering the effective amount of a compound of Formula II or the pharmaceutically acceptable salt thereof.

18. A method for sensitizing tuberculosis bacteria to treatment with a drug against tuberculosis comprising administering to a mammal in need thereof an effective amount of a compound of Formula II of claim 1, thereby sensitizing tuberculosis bacteria to treatment with a drug against tuberculosis.

19. The method according to claim 15, wherein the method further comprises contacting the tuberculosis bacteria with an effective amount of the drug against tuberculosis, thereby eradicating the tuberculosis bacteria.

20. The method according to claim 1, wherein $R_2$ is selected from the group consisting of:
a) H,
b) Cl, F, Br, I,
c) $CH_2OH$, and
d) $C_1$-$C_4$ alkyl.

* * * * *